(12) United States Patent
Fox et al.

(10) Patent No.: US 8,101,728 B2
(45) Date of Patent: Jan. 24, 2012

(54) TAB MOLECULES

(75) Inventors: Judith A. Fox, San Francisco, CA (US); M. Harunur Rashid, Sunnyvale, CA (US); Martin Roberge, Blainville (CA); Volker Schellenberger, Palo Alto, CA (US)

(73) Assignee: Danisco US Inc., Palo Alto, CA (US)

( * ) Notice: Subject to any disclaimer, the term of this patent is extended or adjusted under 35 U.S.C. 154(b) by 326 days.

(21) Appl. No.: 11/885,492

(22) PCT Filed: Apr. 21, 2006

(86) PCT No.: PCT/US2006/015082
§ 371 (c)(1),
(2), (4) Date: Oct. 7, 2008

(87) PCT Pub. No.: WO2006/116076
PCT Pub. Date: Nov. 2, 2006

(65) Prior Publication Data
US 2009/0203104 A1    Aug. 13, 2009

Related U.S. Application Data

(60) Provisional application No. 60/675,728, filed on Apr. 28, 2005.

(51) Int. Cl.
*C07K 16/00* (2006.01)
(52) U.S. Cl. .................................. 530/391.7; 530/391.1
(58) Field of Classification Search .......................... None
See application file for complete search history.

(56) References Cited

U.S. PATENT DOCUMENTS

| | | | |
|---|---|---|---|
| 4,458,066 A | 7/1984 | Caruthers et al. | 536/27 |
| 4,522,811 A | 6/1985 | Eppstein et al. | 514/2 |
| 4,675,187 A | 6/1987 | Konishi et al. | 424/117 |
| 4,711,845 A | 12/1987 | Gelfand et al. | 435/68 |
| 4,975,278 A | 12/1990 | Senter et al. | 424/94.3 |
| 5,711,944 A | 1/1998 | Gilbert et al. | 424/85.7 |
| 5,766,883 A | 6/1998 | Ballance et al. | 435/69.7 |
| 5,773,435 A | 6/1998 | Kadow et al. | 540/222 |
| 5,843,440 A | 12/1998 | Pouletty et al. | 424/133.1 |
| 6,216,375 B1 | 4/2001 | Griffin | 40/618 |
| 6,495,137 B1 * | 12/2002 | Mezes et al. | 424/133.1 |
| 6,537,988 B2 | 3/2003 | Lee | 514/221 |
| 2003/0049689 A1 | 3/2003 | Chen et al. | 435/6 |
| 2003/0100467 A1 | 5/2003 | Aehle et al. | 510/392 |
| 2003/0104591 A1 | 6/2003 | Murray | 435/183 |
| 2003/0147874 A1 | 8/2003 | Schellenberger et al. | 424/94.1 |

FOREIGN PATENT DOCUMENTS

| | | | |
|---|---|---|---|
| EP | 0 196 864 | | 10/1996 |
| WO | WO99/19362 | * | 4/1999 |
| WO | WO 99/19362 | | 4/1999 |
| WO | WO99/43816 | * | 9/1999 |
| WO | WO 99/43816 | | 9/1999 |
| WO | WO 00/24782 | | 5/2000 |
| WO | WO 03/105757 A2 | | 12/2003 |
| WO | WO 03/107009 | | 12/2003 |
| WO | WO2004/003155 | * | 1/2004 |
| WO | WO 2004/003155 | | 1/2004 |
| WO | WO 2005/040344 | | 9/2004 |
| WO | WO2005/021594 | * | 3/2005 |

OTHER PUBLICATIONS

Meyer Bioconjugate Chem. vol. 6 p. 440 (1995).*
Skolnick et al. (Trends in Biotech., 18(1):34-39, 2000).*
Alderson et al., "Characterization of CC49-Based Single-Chain Frangment-beta-Lactamase Fusion Protein for Antibody-Directed Enayme Prodrug Therapy (ADEPT)", *Bioconjugate Chem.*, 17, 410-418, 2006.
Altschul et al., "Basic Local Alignment Search Tool," *J. of Molecular Biology*, vol. 215, pp. 403-410, 1990.
Altschul et al.,"Gapped BLAST and PSI-BLAST: a new generation of protein database search programs," *Nucleic Acids Res.*, vol. 25, No. 17, pp. 3389-3402, 1997.
Amin, N. et al., "Construction of stabilized proteins by combinatorial consensus mutagenesis", *Protein Engineering, Design and Selection* 17: 787-793, 2004.
Bagshawe et al., "Developments with targeted enzymes in cancer therapy," *Current Opinion in Immunology*, vol. 11, pp. 579-583, 1999.
Beaucage et al., "Deoxynucleoside Phosphoramidites-A new Class of Key Intermediates for Deoxypolynucleotide Synthesis," *Tetrahedron Lett.*, vol. 22, pp. 1859-1862, 1981.
Benito et al, "Insertion of a 27 amino acid viral peptide in different zones of *Escherichia coli* β-galactosidase: Effect on the enzyme activity," *FEMS Microbiology Letters*, vol. 123, pp. 107-112, 1994.
Bolivar et al., "Construction and Characterization of New Cloning Vehicles," *Gene*, vol. 2, pp. 95-113, 1977.
Broach, J.R., "Construction of High Copy Yeast Vectors using 2-μm Circle Sequences," *Meth. In Enzymology*, vol. 101, pp. 307-324, 1983.
Brown et al., "Chemical Synthesis and Cloning of a Tyrosine tRNA Gene," *Meth. Enzymol.*, vol. 68, pp. 109-151, 1979.
Cao, Y. et al. "Thomsen-Friedenreich-related carbohydrate antigens in normal adult human tissues: a systematic and comparative study." *Histochemistry and Cell Biology* 106(2): 197-207, 1996.
Chang et al., "Phenotypic Expression in *E. coli* of a DNA Sequence Coding for Mouse Dihydrofolate Reductase," *Nature* 275, pp. 617-624 1978.
Christofidou-Solomidou et al., "Immunotargeting of glucosooxidase to endothelium in vivo causes oxidative vascular injury in the lungs," *Am. J. Physiol. Lung Cell. Mol. Physiol.*, vol. 278, pp. L794-L805, 2000.
Clarke et al., "Selection Procedure for isolation of Centromere DNAs from *Saccharomyces cerevisiae,*" *Meth.In. Enz.*, vol. 101, pp. 300-307, 1983.
Clewell et al., "Supercoiled Circular DNA-Protein Complex in *Escherichia coli*: Purification and Induced Conversion to an Open Circular DNA Form," *Proc. Natl. Acad. Sci. USA*, vol. 62, pp. 1159-1166, 1969.
Clewell, J., "Nature of Col E₁ Plasmid Replication in *Escherichia coli* in the Presence of Chloramphenicol," *Bacteriol.*, vol. 110, pp. 667-675, 1972.
Cohen et al., "Nonchromosomal Antibiotic Resistance in Bacteria: Genetic Transformation of *Escherichia coil* by R-Factor DNA," *Proc. Natl. Acad. Sci. USA*, vol. 69, pp. 2110-2114, 1972.

(Continued)

*Primary Examiner* — Sheela J Huff

(57) ABSTRACT

The present invention relates to TAB molecules, ADEPT constructs directed against TAG-72, and their use in therapy.

6 Claims, 29 Drawing Sheets

OTHER PUBLICATIONS

Dani, V.S. et al. "MODIP revisited: re-evaluation and refinement of an automated procedure for modeling of disulfide bonds in proteins." *Protein Engineering* 16(3): 187-193, Mar. 2003.

Denny, "Prodrug strategies in Cancer Therapy", *Eur. J. Med. Chem.*, 36:577-95 (2001).

Depicker et al., "Nopaline synthase: Transcript Mapping and DNA Sequence," *J. Mol. Appl. Gen.*, vol. 1, pp. 561-573, 1982.

Fiers et al., "Complete nucleotide sequence of SV40 DNA, " *Nature*, vol. 273, pp. 113-120, 1978.

Galleni, M. et al. "Sequence and comparative analysis of three Enterobacter cloacae ampC fl-lactamase genes and their products." *Biochem. J* 250: 753-760, 1988.

Goeddel et al., "Synthesis of human fibroblast interferon by *E. coli*," *Nuc. Acids Res.*, vol. 8, pp. 4057-4075, 1980.

Goodchild,J., "Conjugates of Oligonucleotides and Modified Oligonucleotides: A Review of Their Synthesis and Properties," *Bioconjugate Chemistry*, vol. 1, No. 3, pp. 165-187, 1990.

Graham et al., "A New Technique for the Assay of Infectivity of Human Adenovirus 5 DNA," *Virology* 52:456-467 (1973).

Hess et al., "Cooperation of Glycolytic Enzymes," *J. Adv. Enzyme Reg.*, vol. 7, pp. 149-167, 1968.

Hitzeman et al., "Isolation and Characterization of the Yeast 3-Phosphoglycerokinase Gene (PGK) by an Immunological Screening Technique," *J. Biol. Chem.*, 255:2073 (1980).

Holland et al., The Primary Structures of Two Yeast Enolase Genes, *J. Biol. Chem.*, vol. 256, No. 3, pp. 1385-1395, 1981.

Holland et al., "Isolation and Identification of Yeast Messenger Ribonucleic Acids Coding for Enolase, Glyceraldehyde-3-phosphate Dehydrogenase, and Phosphoglycerate Kinase," *Biochemistry*, vol. 17, pp. 4900-4907, 1978.

Hsiao et al., "High-Frequency transformation of yeast by plasmids containing the cloned yeast ARG4gene," *Proc. Natl. Acad. Sci. USA*, vol. 76, No. 8,pp. 3829-3833, 1979.

International Search Report for PCT/US2006/015082 dated Oct. 23, 2006.

Kerr et al., "Development and Activitires of a New Melphalan Prodrug Designed for Tumor-Selective Activation", *Bioconjugate Chem.*, 9:255-259 (1998).

Long-McGie, J. et al. "Rapid in vivo evolution of a β-lactamase using phagemids." *Biotechnology and Bioengineering* 68(1): 121-125, 2000.

Margolin et al., "Substrate Specificity of Penicillin Smidase From *E. coli*," *Biochim. Biophys. Acta.*, vol. 616, pp. 283-289, 1980.

Maxam et al., Sequencing End-Labeled DNA with Base-Specific Chemical Cleavages, *Methods in Enzymology*, vol. 65, pp. 499-560, 1980.

McDonagh et al., Improved Yield and Stability of L49-sFv-beta-Lactamase a Single-Chain Antibody Fusion Protein for Anticancer Prodrug Activation, by Protein Engineering, *Bioconjugate Chem.*, 14, 860-869, 2003.

Messing et al., "A system for shotgun DNA sequencing," *Nuc. Acids Res.*, vol. 9, pp. 309-321, 1981.

Meyer, D.L. et al. "Site-specific Prodrug Activation by Antibody-β-Lactamase Conjugates: Regression and Long-Term Growth Inhibition of Human Colon Carcinoma Xenograft Models." *Cancer Res* 53(17): 3956-3963, Sep. 1, 1993.

Miller et al., "An Insect Baculovirus Host-Vector System for High-Level Expression of Foreign Genes," *Genetic Engineering*, 1986, Setlow et al., Eds., Plenum Publishing, vol. 8, pp. 277-298.

Napolitano et al., "Glubodies: randomized libraries of glutathione transferase enzymes," *Chem. Biol.*, vol. 3, pp. 359-367, 1996.

Narang et al., "Improved Phosphotriester Method for the Synthesis of Gene Fragments," *Meth. In Enzymol.*, vol. 68, pp. 90-99, 1979.

Niculescu-Duvaz et al., "Prodrugs for antibody- and gene-directed enzyme prodrug therapies (ADEPT and GDEPT)," *Anticancer Drug Des.*, vol. 14, pp. 517-538, 1999.

O'Boyle, KP. et al. "Specificity analysis of murine monoclonal antibodies reactive with Tn, sialylated Tn, T and monosialylated (2-6) T antigens," *Hybridoma* 15: 401-408, 1996.

Papot, S. et al. "Design of Selectively Activated Anticancer Prodrugs: Elimination and Cyclization Strategies." *Current Medicinal Chemistry-Anti-Cancer Agents* 2(2): 155-185, Mar. 2002.

Roberge et al., Construction and optimization of a CC49-Based scFv-beta-lactamase fusion protein for ADEPT, *Protein Engineering, Design & Selection*, V.19:4, pp. 141-145, 2006.

Sambrook et al, Eds. *Molecular Cloning: A Laboratory Manual*, 2d Ed., Cold Spring Harbor Laboratory Press, pp. 9.47-57, and Chapter 15.51, 1989.

Sanger et al., "DNA sequencing with chain-terminating inhibitors," *Proc. Natl. Acad. Sci. USA*, vol. 74, No. 12, pp. 5463-5467, 1977.

Senter, P.D. et al. "Selective activation of anticancer prodrugs by monoclonal antibody-enzyme conjugates." *Advanced Drug Delivery Reviews* 53(3): 247-264, Dec. 31, 2001.

Shaw et al., "A general method for the transfer of cloned genes to plant cells," *Gene*, vol. 23, pp. 315-330, 1983.

Shimatake et al., Purified λ regulatory protein cII positively activates promoters for lysogenic development, *Nature*, vol. 292, pp. 128-132 1981.

Sirot, D. "Extended-spectrum plasmid-mediated beta-lactamases." *J. Antimicrob. Chemother* 36 Suppl A: 19-34, Jul. 1995.

Smith et al., "Protein Loop Grafting to Construct a Variant of Tissue-type Plasminogen Activator that Binds Platelet Integrin alpha IIb beta3 ", *J. Biol. Chem.*, 270:30486 (1995).

Solingen et al., "Fusion of Yeast Spheroplasts", *J. Bact.*, 130:2, pp. 946-947 (1977).

Stella et al., "Prodrugs: A Chemical Approach to Targeted Drug Delivery," *Directed Drug Delivery*, R. Borchardt et al, Eds., pp. 247-267, Humana Press, 1985.

Stickler, M. et al., "Human Population-based Identification of CD4[+] T-Cell Peptide Epitope Determinants," *Journal of Immunological Methods*, 281:95-108 (2003).

Stinchcomb et al., "Isolation and characterization of a yeat chromosomal replicator," *Nature*, vol. 282, pp. 39-43, 1979.

Thomson et al., "Version 2000 : the new beta-lactamases of Gram-negative bacteria at the dawn of the new millenium", *Microbes and Infection*, 2:1225-1235 (2000).

Trouet et al., "A covalent linkage between daunorubicin and proteins that is stable in serum and reversible by lysosomal hydrolases, as required for a lysosomotropic drug-carrier conjugate: In vitro and in vivo studies," *Proc. Natl. Acad. Sci. USA*, vol. 79, pp. 626-629, 1982.

Tschumper et al., Sequence of a yeast DNA fragment containing a chromosomal replicator and the TRP1 gene, *Gene*, vol. 10, 157-166, 1980.

Umemoto et al., "Preparation and invitro cytotoxicity of a methotrexate-anit-MM46 monoclonal antibody conjugate via an oligopeptide spacer,", *Int. J. Cancer*, 43:677 (1989).

Vrudhula, V.M. et al. "Cephalosporin Derivatives of Doxorubicin as Prodrugs for Activation by Monoclonal Antibody-β-Lactamase Conjugates." *J. Med. Chem.* 38(8): 1380-1385, Apr. 14, 1995.

Vrudhula, V.M. et al. "Cephalosporin prodrugs of paclitaxel for immunologically specific activation by L-49-sFv-β-Lactamase fusion protein." *Bioorganic & Medicinal Chemistry Letters* 13(3): 539-542, Feb. 10, 2003.

Vrudhula, V.M. et al. "Prodrugs of doxorubicin and melphalan and their activation by a monoclonal antibody-penicillin-G amidase conjugate." *J. Med. Chem.* 36(7): 919-923, Apr. 2, 1993.

Wang, W. & Malcolm, B.A., "Two-stage PCR protocol allowing introduction of multiple mutations, deletions and insertions using QuikChange site-directed mutagenesis", *BioTechniques* 26:680-682 (1999).

Wilman, "Prodrugs in Cancer Chemotherapy," *biochemical society Transactions*, 14:375-382 (615th Meeting Belfast 1986).

Wu, T.T. et al. "An analysis of the sequences of the variable regions of Bence Jones proteins and myeloma light chains and their implications for antibody complementarity." *J. Exp. Med* 132(2): 211-50, Aug. 1, 1970.

Xu et al., "Strategies for Enzyme/Prodrug Cancer Therapy", *Clinical. Cancer Res.*, 7:3314-3324 (2001).

\* cited by examiner

```
  1  QVQLQQSDAE LVKPGASVKI SCKASGYTFT DHAIHWVKQN PEQGLEWIGY
 51  FSPGNDDFKY NERFKGKATL TADKSSSTAY VQLNSLTSED SAVYFCTRSL
101  NMAYWGQGTS VTVSSGGGGS GGGGSGGGGS GGGGSGGGGS GGGGSDIVMS
151  QSPSSLPVSV GEKVTLSCKS SQSLLYSGNQ KNYLAWYQQK PGQSPKLLIY
201  WASARESGVP DRFTGSGSGT DFTLSISSVK TEDLAVYYCQ QYYSYPLTFG
251  AGTKLVLKTP VSEKQLAEVV ANTITPLMKA QSVPGMAVAV IYQGKPHYYT
301  FGKADIAANK PVTPQTLFEL GSISKTFTGV LGGDAIARGE ISLDDAVTRY
351  WPQLTGKQWQ GIRMLDLATY TAGGLPLQVP DEVTDNASLL RFYQNWQPQW
401  KPGTTRLYAN ASIGLFGALA VKPSGMPYEQ AMTTRVLKPL KLDHTWINVP
451  KAEEAHYAWG YRDGKAVRVS PGMLDAQAYG VKTNVQDMAN WVMANMAPEN
501  VADASLKQGI ALAQSRYWRI GSMYQGLGWE MLNWPVEANT VVETSFGNVA
551  LAPLPVAEVN PPAPPVKASW VHKTGSTGGF GSYVAFIPEK QIGIVMLANT
601  SYPNPARVEA AYHILEALQ
```

Amino acid sequence of TAB2.4 protein (619-aa). The vH and vL sequences are underlined, the linker between vH and vL is in bold.

FIG. 1A

CC49 scFv Protein Sequence qvqlqqsdaelvkpgasvkisckasgytftdhaihwvkqnpeqglewigyfspgnddfkynerf
kgkatltadkssstayvqlnsltsedsavyfctrslnmaywgqgtsvtvssggggsggggsggg
gsdivmsqspsslpvsvgekvtlscksсqsllysgnqknylawyqqkpgqspklliywasares
gvpdrftgsgsgtdftlsissvktedlavyycqqyysypltfgagtklvlk

FIG. 1B

Protein Sequence of TEM4 BLA from TAB2.6 tpvhpetlvkvkdaedqlgarvgyieldlnsgkilesfrpeerfpmmstfkvllcgavlsrvda
gqeqlgrrihysqndlvkyspvtekhltdgmtvrelcsaaitmsdntaanllittiggpkelta
flhnmgdhvtrldrwepelneaipnderdttmpvamattlrklltgelltlasrqqlidwmead
kvagpllrsalpagwfiadksgagergsrgiiaalgpdgkpsrivviyttgsqatmdernrqia
eigaslikhw*

FIG. 1C

TAB2.1 Protein Sequence qvqlqqsdaelvkpgasvkisckasgytftdhaihwvkqnpeqglewigyfspgnddfkynerf
kgkatltadkssstayvqlnsltsedsavyfctrslnmaywgqgtsvtvssggggsggggsggg
gsdivmsqspsslpvsvgekvtlscksсqsllysgnqknylawyqqkpgqspklliywasares
gvpdrftgsgsgtdftlsissvktedlavyycqqyysypltfgagtklvlktpvsekqlaevva
ntitplmkaqsvpgmavaviyqgkphyytfgkadiaankpvtpqtlfelgsisktftgvlggda
iargeislddavtrywpqltgkqwqgirmldlatytagglplqvpdevtdnasllrfyqnwqpq
wkpgttrlyanasiglfgalavkpsgmpyeqamttrvlkplkldhtwinvpkaeeahyawgyrd
gkavrvspgmldaqaygvktnvqdmanwvmanmapenvadaslkqgialaqsrywrigsmyqgl
gwemlnwpveantvvetsfgnvalaplpvaevnppappvkaswvhktgstggfgsyvafipekq
igivmlantsypnparveaayhilealq*

FIG. 1D

TAB2.1 DNA Sequence

```
caggtgcagttacagcagtcagatgcggagttggtgaaaccgggcgcgagcgtaaagatttctt
gtaaagcatccggctacacctttaccgaccatgccattcactgggtaaaacagaacccggaaca
gggcctggagtggattgggtatttcagcccgggtaatgatgactttaagtataacgaacgcttt
aaaggtaaagccaccctgacggcggacaaatcgtcgtccactgcttacgtccagctgaacagtc
tcacgtcagaagatagcgcggtgtatttctgtacgcgtagccttaacatggcgtattggggtca
agggaccagcgtgaccgttagcagcggggcggcggttccggtggaggtggaagtggcggcggt
ggatctgatattgtcatgagtcaatctccgtcatcactgcccgtgagtgttggagaaaaggtga
cgctgagttgcaaaagctcccaaagcctgctatacagcggcaatcagaagaattatctggcatg
gtatcagcagaaaccaggccagtctcctaaattgctgatctattgggcctctgcacgtgaatcc
ggtgttccagatcgtttcaccggcagtggttcgggcactgatttacactgtccatttcgtctg
tgaaaacagaagacctggctgtctactattgccaacaatactactcatatccgcttacctttgg
ggcgggtactaaattagttctcaaaacaccggtgtcagaaaaacagctggcggaggtggtcgcg
aatacgattaccccgctgatgaaagcccagtctgttccaggcatggcggtggccgttatttatc
agggaaaaccgcactattacacatttggcaaggccgatatcgcggcgaataaacccgttacgcc
tcagaccctgttcgagctggttctataagtaaaaccttcaccggcgttttaggtggggatgcc
attgctcgcggtgaaatttcgctggacgatgcggtgaccagatactggccacagctgacgggca
agcagtggcagggtattcgtatgctggatctcgccacctacaccgctggcggcctgccgctaca
ggtaccggatgaggtcacggataacgcctcctgctgcgcttttatcaaaactggcagccgcag
tggaagcctggcacaacgcgtctttacgccaacgccagcatcggtcttttggtgcgctggcgg
tcaaaccttctggcatgccctatgagcaggccatgacgacgcgggtccttaagccgctcaagct
ggaccatacctggattaacgtgccgaaagcggaagaggcgcattacgcctggggctatcgtgac
ggtaaagcggtgcgcgtttcgccgggtatgctggatgcacaagcctatggcgtgaaaaccaacg
tgcaggatatggcgaactgggtcatggcaaacatggcgccggagaacgttgctgatgcctcact
taagcagggcatcgcgctggcgcagtcgcgctactggcgtatcgggtcaatgtatcagggtctg
ggctgggagatgctcaactggcccgtggaggccaacacggtggtcgagacgagttttggtaatg
tagcactggcgccgttgcccgtggcagaagtgaatccaccggctcccccggtcaaagcgtcctg
ggtccataaaacgggctctactggcgggtttggcagctacgtggcctttattcctgaaaagcag
atcggtattgtgatgctcgcgaatacaagctatccgaacccggcacgcgttgaggcggcatacc
atatcctcgaggcgctacagtag
```

FIG. 1E

TAB2.4 Protein Sequence

```
qvqlqqsdaelvkpgasvkisckasgytftdhaihwvkqnpeqglewigyfspgnddfkynerf
kgkatltadkssstayvqlnsltsedsavyfctrslnmaywgqgtsvtvssggggsggggsggg
gsggggsggggsggggsdivmsqspsslpvsvgekvtlsckssqsllysgnqknylawyqqkpg
qspklliywasaresgvpdrftgsgsgtdftlsissvktedlavyycqqyysypltfgagtklv
lktpvsekqlaevyantitplmkaqsvpgmavaviyqgkphyytfgkadiaankpvtpqtlfel
gsisktftgvlggdaiargeislddavtrywpqltgkqwqgirmldlatytagglplqvpdevt
dnasllrfyqnwqpqwkpgttrlyanasiglfgalavkpsgmpyeqamttrvlkplkldhtwin
vpkaeeahyawgyrdgkavrvspgmldaqaygvktnvqdmanwvmanmapenvadaslkqgial
aqsrywrigsmyqglgwemlnwpveantvvetsfgnvalaplpvaevnppappvkaswvhktgs
tggfgsyvafipekqigivmlantsypnparveaayhilealq*
```

FIG. 1F

TAB2.4 DNA Sequence

```
caggtgcagttacagcagtcagatgcggagttggtgaaaccgggcgcgagcgtaaagatttcttg
taaagcatccggctacacctttaccgaccatgccattcactgggtaaaacagaacccggaacagg
gcctggagtggattgggtatttcagcccgggtaatgatgactttaagtataacgaacgctttaaa
ggtaaagccaccctgacggcggacaaatcgtcgtccactgcttacgtccagctgaacagtctcac
gtcagaagatagcgcggtgtatttctgtacgcgtagccttaacatggcgtattggggtcaaggga
ccagcgtgaccgttagcagcggtggtggcggttcgggtggcggaggcagcggtggagggggctct
gggggcggcggttccggtggaggtggaagtggcggcggtggatctgatattgtcatgagtcaatc
tccgtcatcactgccgtgagtgttggagaaaaggtgacgctgagttgcaaaagctcccaaagcc
tgctatacagcggcaatcagaagaattatctggcatggtatcagcagaaaccaggccagtctcct
aaattgctgatctattgggcctctgcacgtgaatccggtgttccagatcgtttcaccggcagtgg
ttcgggcactgattttacactgtccatttcgtctgtgaaaacagaagacctggctgtctactatt
gccaacaatactactcatatccgcttacctttggggcgggtactaaattagttctcaaaacaccg
gtgtcagaaaaacagctggcggaggtggtcgcgaatagattaccccgctgatgaaagcccagtc
tgttccaggcatggcggtggccgttatttatcagggaaaaccgcactattacacatttggcaagg
ccgatatcgcggcgaataaacccgttacgcctcagaccctgttcgagctgggttctataagtaaa
accttcaccggcgttttaggtggggatgccattgctcgcggtgaaatttcgctggacgatgcggt
gaccagatactggccacagctgacgggcaagcagtggcagggtattcgtatgctggatctcgcca
cctacaccgctggcggcctgccgctacaggtaccggatgaggtcacggataacgcctccctgctg
cgcttttatcaaaactggcagccgcagtggaagcctggcacaacgcgtctttacgccaacgccag
catcggtcttttggtgcgctggcggtcaaaccttctggcatgccctatgagcaggccatgacga
cgcgggtccttaagccgctcaagctggaccatacctggattaacgtgccgaaagcggaagaggcg
cattacgcctggggctatcgtgacggtaaagcggtgcgcgtttcgccgggtatgctggatgcaca
agcctatggcgtgaaaaccaacgtgcaggatatggcgaactgggtcatggcaaacatggcgccgg
agaacgttgctgatgcctcacttaagcagggcatcgcgctggcgcagtcgcgctactggcgtatc
gggtcaatgtatcagggtctgggctgggagatgctcaactggcccgtggaggccaacacggtggt
cgagacgagttttggtaatgtagcactggcgccgttgcccgtggcagaagtgaatccaccggctc
ccccggtcaaagcgtcctgggtccataaaacgggctctactggcgggtttggcagctacgtggcc
tttattcctgaaaagcagatcggtattgtgatgctcgcgaatacaagctatccgaacccggcacg
cgttgaggcggcataccatatcctcgaggcgctacagtag
```

FIG. 1G

TAB2.5 Protein Sequence

```
qvqlqqsdaelvkpgasvkisckasgytftdhaihwvkqnpeqglewigyfspgnddfkynerfk
gkatltadkssstaylqlnsltsedsavyfctrslnmaywgqgtsvtvssggggsggggsggggs
ggggsggggsggggsdivmtqspsslpvsvgekvtlscskssqsllysgnqknylawyqqkpgqsp
klliywastresgvpdrftgsgsgtdftlsissvetedlavyycqqyysypltfgagtklvlktp
vsekqlaevvantitplmkaqsvpgmavaviyqgkphyytfgkadiaankpvtpqtlfelgsisk
tftgvlggdaiargeislddavtrywpqltgkqwqgirmldlatytagglplqvpdevtdnasll
rfyqnwqpqwkpgttrlyanasiglfgalavkpsgmpyeqamttrvlkplkldhtwinvpkaeea
hyawgyrdgkavrvspgmldaqaygvktnvqdmanwvmanmapenvadaslkqgialaqsrywri
gsmyqglgwemlnwpveantvvetsfgnvalaplpvaevnppappvkaswvhktgstggfgsyva
fipekqigivmlantsypnparveaayhilealq*
```

FIG. 1H

TAB2.5 DNA Sequence

```
caggtgcagttacagcagtcagatgcggagttggtgaaaccgggcgcgagcgtaaagatttcttg
taaagcatccggctacacctttaccgaccatgccattcactgggtaaaacagaacccggaacagg
gcctggagtggattgggtatttcagcccgggtaatgatgactttaagtataacgaacgctttaaa
ggtaaagccaccctgacggcggacaaatcgtcgtccactgcttacctgcagctgaacagtctcac
gtcagaagatagcgcggtgtatttctgtacgcgtagccttaacatggcgtattggggtcaaggga
ccagcgtgaccgttagcagcggtggtggcggttcgggtggcggaggcagcggtggaggggggctct
ggggcggcggttccggtggaggtggaagtggcggcggtggatctgatattgtcatgacccaatc
tccgtcatcactgcccgtgagtgttggagaaaggtgacgctgagttgcaaaagctcccaaagcc
tgctatacagcggcaatcagaagaattatctggcatggtatcagcagaaaccaggccagtctcct
aaattgctgatctattgggcctctacccgtgaatccggtgttccagatcgtttcaccggcagtgg
ttcgggcactgattttacactgtccatttcgtctgtggaaacagaagacctggctgtctactatt
gccaacaatactactcatatccgcttaccttggggcaggtactaaattagttctcaaaacgccg
gtgtcagaaaaacagctggcggaggtggtcgcgaatacgattaccccgctgatgaaagcccagtc
tgttccaggcatggcggtggccgttatttatcagggaaaaccgcactattacacatttggcaagg
ccgatatcgcggcgaataaacccgttacgcctcagaccctgttcgagctgggttctataagtaaa
accttcaccggcgttttaggtggggatgccattgctcgcggtgaaatttcgctggacgatgcggt
gaccagatactggccacagctgacgggcaagcagtggcagggtattcgtatgctggatctcgcca
cctacaccgctggcggcctgccgctacaggtaccggatgaggtcacggataacgcctccctgctg
cgcttttatcaaaactggcagccgcagtggaagcctggcacaacgcgtctttacgccaacgccag
catcggtcttttggtgcgctggcggtcaaaccttctggcatgccctatgagcaggccatgacga
cgcgggtccttaagccgctcaagctggaccatacctggattaacgtgccgaaagcggaagaggcg
cattacgcctggggctatcgtgacggtaaagcggtgcgcgtttcgccgggtatgctggatgcaca
agcctatggcgtgaaaaccaacgtgcaggatatggcgaactgggtcatggcaaacatggcgccgg
agaacgttgctgatgcctcacttaagcagggcatcgcgctggcgcagtcgcgctactggcgtatc
gggtcaatgtatcagggtctgggctgggagatgctcaactggcccgtggaggccaacacggtggt
cgagacgagttttggtaatgtagcactggcgccgttgcccgtggcagaagtgaatccaccggctc
ccccggtcaaagcgtcctgggtccataaaacgggctctactggcgggtttggcagctacgtggcc
tttattcctgaaaagcagatcggtattgtgatgctcgcgaatacaagctatccgaacccggcacg
cgttgaggcggcataccatatcctcgaggcgctacagtag
```

*FIG. 1I*

TAB2.6 Protein Sequence

```
qvqlqqsdaelvkpgasvkisckasgytftdhaihwvkqnpeqglewigyfspgnddfkynerf
kgkatltadkssstaylqlnsltsedsavyfctrslnmaywgqgtsvtvssggggsggggsggg
gsggggsggggsggggsdivmtqspsslpvsvgekvtlsckssqsllysgnqknylawyqqkpg
qspklliywastresgvpdrftgsgsgtdftlsissvetedlavyycqqyysypltfgagtklv
lktpvhpetlvkvkdaedqlgarvgyieldlnsgkilesfrpeerfpmmstfkvllcgavlsrv
dagqeqlgrrihysqndlvkyspvtekhltdgmtvrelcsaaitmsdntaanllltiggpkel
taflhnmgdhvtrldrwepelneaipnderdttmpvamattlrklltgelltlasrqqlidwme
adkvagpllrsalpagwfiadksgagergsrgiiaalgpdgkpsrivviyttgsqatmdernrq
iaeigaslikhw*
```

*FIG. 1J*

TAB2.6 DNA Sequence caggtgcagttacagcagtcagatgcggagttggtgaaaccgggcgcgagcgtaaagatttctt
gtaaagcatccggctacacctttaccgaccatgccattcactgggtaaaacagaacccggaaca
gggcctggagtggattgggtatttcagcccgggtaatgatgactttaagtataacgaacgcttt
aaaggtaaagccaccctgacggcggacaaatcgtcgtccactgcttacctgcagctgaacagtc
tcacgtcagaagatagcgcggtgtatttctgtacgcgtagccttaacatggcgtattggggtca
agggaccagcgtgaccgttagcagcggtggtggcggttcgggtggcggaggcagcggtggaggg
ggctctggggggcggcggttccggtggaggtggaagtggcggcggtggatctgatattgtcatga
cccaatctccgtcatcactgcccgtgagtgttggagaaaaggtgacgctgagttgcaaaagctc
ccaaagcctgctatacagcggcaatcagaagaattatctggcatggtatcagcagaaaccaggc
cagtctcctaaattgctgatctattgggcctctacccgtgaatccggtgttccagatcgtttca
ccggcagtggttcgggcactgatttacactgtccatttcgtctgtggaaacagaagacctggc
tgtctactattgccaacaatactactcatatccgcttacctttggggcgggtactaaaatagtt
ctcaaaacaccggtgcacccagaaacgctggtgaaagtaaaagatgctgaagatcagttgggtg
cacgagtgggttacatcgaactggatctcaacagcggtaagatccttgagagttttcgccccga
agaacgtttcccaatgatgagcacttttaaagttctgctatgtggcgcggtattatcccgtgtt
gacgccgggcaagagcaactcggtcgccgcatacactattctcagaatgacttggttaagtact
caccagtcacagaaaagcatcttacggatggcatgacagtaagagaattatgcagtgctgccat
aaccatgagtgataacactgcggccaacttacttctgacaacgatcggaggaccgaaggagcta
accgcttttttgcacaacatggggatcatgtaactcgccttgatcgttgggaaccggagctga
atgaagccataccaaacgacgagcgtgacaccacgatgcctgtagcaatggcaacaacgttgcg
caaactattaactggcgaactacttactctagcttcccggcaacaattaatagactggatggag
gcggataaagttgcaggaccacttctgcgctcggcccttccggctggctggtttattgctgata
aatctggagccggtgagcgtgggtctcgcggtatcattgcagcactggggccagatggtaagcc
ctcccgtatcgtagttatctacacgacggggagtcaggcaactatgatgaacgaaatagacag
atcgctgagataggtgcctcactgattaagcattggtaa

FIG. 1K

TAB2.7 Protein Sequence qvqlqqsdaelvkpgasvkiscka sgytftdhaihwvkqnpeqglewigyfspgnddfkynerf
kgkatltadkssstaylqlnsltsedsavyfctrslnmaywgqgtsvtvssggggsggggsggg
gsggggsggggsggggsdivmtqspsslpvsvgekvtlsckssqsllysgnqknylawyqqkpg
qspklliywastresgvpdrftgsgsgtdftlsissvetedlavyycqqyysypltfgagtklv
lktpvsekqlaevvantitplmkaqsipgmavaviyqgkphyytfgkadiaankpvtpqtlfel
gsisktftgvlggdaiargeislddavtkywpeltgkqwqgirmldlatytagglplqvpdevt
dnasllrfyqnwqpqwkpgttrlyanssiglfgalavkpsgmpyeqamttrvlkplkldhtwin
vpkaeeahyawgyrdgkavrvspgmldaqaygvktnvqdmarwvmanmapenvadaslkqgial
aqsrywrvgsmyqglgwemlnwpveantviegsdskvalaplpvaevnppappvkaswvhktgs
tggfgsyvafipekqlgivmlantsypnparveaayhilealq*

FIG. 1L

TAB2.7 DNA Sequence caggtgcagttacagcagtcagatgcggagttggtgaaaccgggcgcgagcgtaaagatttcttg
taaagcatccggctacacctttaccgaccatgccattcactgggtaaaacagaacccggaacagg
gcctggagtggattgggtatttcagcccgggtaatgatgactttaagtataacgaacgctttaaa
ggtaaagccaccctgacggcggacaaatcgtcgtccactgcttacctgcagctgaacagtctcac
gtcagaagatagcgcggtgtatttctgtacgcgtagccttaacatggcgtattggggtcaaggga
ccagcgtgaccgttagcagcggtggtggcggttcgggtggcggaggcagcggtggaggggggctct
gggggcggcggttccggtggaggtggaagtggcggcggtggatctgatattgtcatgacccaatc
tccgtcatcactgcccgtgagtgttggagaaaaggtgacgctgagttgcaaaagctcccaaagcc
tgctatacagcggcaatcagaagaattatctggcatggtatcagcagaaaccaggccagtctcct
aaattgctgatctattgggcctctacccgtgaatccggtgttccagatcgtttcaccggcagtgg
ttcgggcactgattttacactgtccatttcgtctgtggaaacagaagacctggctgtctactatt
gccaacaatactactcatatccgcttacctttggggcgggtactaaattagttctcaaaacacc
gtgtcagaaaaacagctggcggaggtggtcgcgaatacgattacccgctgatgaaagcacagag
tattccaggcatggcggtggccgttatttatcagggaaaaccgcactattacacatttggcaagg
ccgatatcgcggcgaataaacccgttacgcctcagaccctgttcgagctgggttctataagtaaa
accttcaccggcgttttaggtggggatgccattgctcgcggtgaaatttcgctggacgatgcggt
gaccaaatactggccagagctgacgggcaagcagtggcagggtattcgtatgctggatctcgcca
cctacaccgctggcggcctgccgctacaggtaccggatgaggtcacggataacgcctccctgctg
cgcttttatcaaaactggcagccgcagtggaagcctggcacaacgcgtctttacgccaactccag
catcggtcttttggtgcgctggcggtcaaaccttctggcatgccctatgagcaggccatgacga
cgcgggtccttaagccgctcaagctggaccatacctggattaacgtgccgaaagcggaagaggcg
cattacgcctggggctatcgtgacggtaaagcggtgcgcgtttcgccgggtatgctggatgcaca
agcctatggcgtgaaaaccaacgtgcaggatatggcgcgctgggtcatggccaacatggccccgg
agaacgttgctgatgcctcacttaagcagggcatcgcgctggcgcagtcgcgctactggcgtgtc
gggtcaatgtatcagggtctcggctgggagatgctcaactggcccgtggaggcaaacacggtgat
cgagggcagcgacagtaaggtagcgctagcgccgttgcccgtggcagaagtgaatccaccggctc
ccccggtcaaagcgtcctgggtccataaaactggctctactggcgggtttggatcctacgtggcc
tttattcctgaaaagcagctcggtattgtgatgctcgcgaatacaagctatccgaacccggctcg
agttgaggcggcataccatatcctagaggcgctacagtaa

FIG. 1M pME403.3 Protein Sequence qvqlqqsdaelvkpgasvkiscka sgytftdhaihwvkqnpeqglewigyfspgnddfkynerf
kgkatltadkssstaylqlnsltsedsavyfctrslnmcywgqgtsvtvssggggsggggsggg
gsggggsggggsggggsdivmtqspsslpvsvgekvtlscksssqsllysgnqknylawyqqkpg
qspkcliywastresgvpdrftgsgsgtdftlsissvetedlavyycqqyysypltfgagtklv
lktpvsekqlaevvantitplmkaqsipgmavaviyqgkphyytfgkadiaankpvtpqtlfel
gsisktftgvlggdaiargeislddavtkywpeltgkqwqgirmldlatytagglplqvpdevt
dnasllrfyqnwqpqwkpgttrlyanssiglfgalavkpsgmpyeqamttrvlkplkldhtwin
vpkaeeahyawgyrdgkavrvspgmldaqaygvktnvqdmarwvmanmapenvadaslkqgial
aqsrywrvgsmyqglgwemlnwpveantviegsdskvalaplpvaevnppappvkaswvhktgs
tggfgsyvafipekqlgivmlantsypnparveaayhilealq*

FIG. 1N pME403.3 DNA Sequence caggtgcagttacagcagtcagatgcggagttggtgaaaccgggcgcgagcgtaaagatttcttg
taaagcatccggctacacctttaccgaccatgccattcactgggtaaaacagaacccggaacagg
gcctggagtggattgggtatttcagcccgggtaatgatgactttaagtataacgaacgctttaaa
ggtaaagccaccctgacggcggacaaatcgtcgtccactgcttacctgcagctgaacagtctcac
gtcagaagatagcgcggtgtatttctgtacgcgtagccttaacatgtgctattggggtcaaggga
ccagcgtgaccgttagcagcggtggtggcggttcgggtggcggaggcagcggtggagggggctct
gggggcggcggttccggtggaggtggaagtggcggcggtggatctgatattgtcatgacccaatc
tccgtcatcactgcccgtgagtgttggagaaaaggtgacgctnagttgcaaaagctcccaaagcc
tgctatacagcggcaatcagaagaattatctggcatggtatcngcagaaaccaggccagtctcct
aaatgcctgatctattgggcctctacccgtgaatccggtgttccagatcgtttcaccggcagtgg
ttcgggcactgattttacactgtccatttcgtctgtggaaacagaagacctggctgtctactatt
gccaacaatactactcatatccgcttacttttggggcgggtactaaattagttctcaaaacaccg
gtgtcagaaaaacagctggcggaggtggtcgcgaatacgattacccgctgatgaaagcacagag
tattccaggcatggcggtggccgttatttatcagggaaaaccgcactattacacatttggcaagg
ccgatatcgcggcgaataaacccgttacgcctcagaccctgttcgagctggttctataagtaaa
accttcaccggcgttttaggtggggatgccattgctcgcggtgaaatttcgctggacgatgcggt
gaccaaatactggccagagctgacgggcaagcagtggcagggtattcgtatgctggatctcgcca
cctacaccgctggcggcctgccgctacaggtaccggatgaggtcacggataacgcctccctgctg
cgcttttatcaaaactggcagccgcagtggaagcctggcacaacgcgtctttacgccaactccag
catcggtctttttggtgcgctggcggtcaaaccttctggcatgccctatgagcaggccatgacga
cgcgggtccttaagccgctcaagctggaccatacctggattaacgtgccgaaagcggaagaggcg
cattacgcctggggctatcgtgacggtaaagcggtgcgcgtttcgccgggtatgctggatgcaca
agcctatggcgtgaaaaccaacgtgcaggatatggcgcgctgggtcatggccaacatggccccgg
agaacgttgctgatgcctcacttaagcagggcatcgcgctggcgcagtcgcgctactggcgtgtc
gggtcaatgtatcagggtctcggctgggagatgctcaactggcccgtggaggcaaacacggtgat
cgagggcagcgacagtaaggtagcgctagcgccgttgcccgtggcagaagtgaatccaccggctc
ccccggtcaaagcgtcctgggtccataaaactggctctactggcgggtttggatcctacgtggcc
tttattcctgaaaagcagctcggtattgtgatgctcgcgaatacaagctatccgaacccggctcg
agttgaggcggcataccatatcctagaggcgctacagtaa

FIG. 10

TAB2.8 Protein Sequence divmtqspsslpvsvgekvtlscksssqsllysgnqknylawyqqkpgqspklliywastresgv
pdrftgsgsgtdftlsissvetedlavyycqqyysypltfgagtklvlkggggsggggsggggs
ggggsggggsggggsqvqlqqsdaelvkpgasvkiscasgytftdhaihwvkqnpeqglewig
yfspgnddfkynerfkgkatltadkssstaylqlnsltsedsavyfctrslnmaywgqgtsvtv
sstpvsekqlaevvantitplmkaqsvpgmavaviyqgkphyytfgkadiaankpvtpqtlfel
gsisktftgvlggdaiargeislddavtrywpqltgkqwqgirmldlatytagglplqvpdevt
dnasllrfyqnwqpqwkpgttrlyanasiglfgalavkpsgmpyeqamttrvlkplkldhtwin
vpkaeeahyawgyrdgkavrvspgmldaqaygvktnvqdmanwvmanmapenvadaslkqgial
aqsrywrigsmyqglgwemlnwpveantvvetsfgnvalaplpvaevnppappvkaswvhktgs
tggfgsyvafipekqigivmlantsypnparveaayhilealq*

FIG. 1P

TAB2.8 DNA Sequence

```
gatattgtcatgacgcaatctccgagctccctgccagttagcgtcggcgagaaagtgacgctgag
ctgtaaatccagccaatctctgctgtatagcggcaatcagaagaactacctggcgtggtaccagc
agaaaccgggtcagtccccgaagctgctgatttattgggcttctacccgcgaaagcggtgtccca
gaccgcttcacgggtagcggtagcggcactgacttcaccctgtccatttcttctgttgaaacgga
agatctggcggtgtattactgccaacagtattactcctatccactgactttcggtgccggcacta
aactggttctgaagggtggcggcggttccggcggtggtggttccggtggcggtggctctggcggc
ggtggctccggcggcggcggttctggcggtggcggatcccaggtgcagctgcaacaaagcgatgc
agagctggttaaacctggtgcgagcgttaaaattagctgcaaggcgtccggttatacttttaccg
atcacgccattcactgggtcaagcagaacccggaacaaggcctggagtggatcggctatttctct
ccgggcaacgatgacttcaaatacaatgaacgctttaaaggcaaagccactctgaccgctgataa
atctagctccacggcctacctgcaactgaacagcctgacctccgaagatagcgccgtgtatttct
gcacccgcagcctgaatatggcgtactggggccagggcacttccgtgacggtgagcagcacaccg
gtgtcagaaaaacagctggcggaggtggtcgcgaatacgattacccgctgatgaaagcccagtc
tgttccaggcatggcggtggccgttatttatcagggaaaaccgcactattacacatttggcaagg
ccgatatcgcggcgaataaacccgttacgcctcagaccctgttcgagctgggttctataagtaaa
accttcaccggcgttttaggtggggatgccattgctcgcggtgaaatttcgctggacgatgcggt
gaccagatactggccacagctgacgggcaagcagtggcagggtattcgtatgctggatctcgcca
cctacaccgctggcggcctgccgctacaggtaccggatgaggtcacggataacgcctccctgctg
cgcttttatcaaaactggcagccgcagtggaagcctggcacaacgcgtctttacgccaacgccag
catcggtcttttggtgcgctggcggtcaaaccttctggcatgccctatgagcaggccatgacga
cgcgggtccttaagccgctcaagctggaccatacctggattaacgtgccgaaagcggaagaggcg
cattacgcctggggctatcgtgacggtaaagcggtgcgcgtttcgccgggtatgctggatgcaca
agcctatggcgtgaaaaccaacgtgcaggatatgcgaactgggtcatggcaaacatggcgccgga
gaacgttgctgatgcctcacttaagcagggcatcgcgctggcgcagtcgcgctactggcgtatcg
ggtcaatgtatcagggtctgggctgggagatgctcaactggcccgtggaggccaacacggtggtc
gagacgagttttggtaatgtagcactggcgccgttgcccgtggcagaagtgaatccaccggctcc
cccggtcaaagcgtcctgggtccataaaacgggctctactggcgggtttggcagctacgtggcct
ttattcctgaaaagcagatcggtattgtgatgctcgcgaatacaagctatccgaacccggcacgc
gttgaggcggcataccatatcctcgaggcgctacagtag
```

*FIG. 1Q*

Screening Data for Binding to Coated BSM of Clones from Libraries ME367 and ME368.

Screening Data for Binding to Coated BSM of Clones from Libraries ME367 and ME368.

Screening Data for Binding to Coated BSM vs Input BLA Activity of Clones from Libraries ME374, ME375 and ME377. Many Clones in the Libraries Were wt TAB2.4 and Are Shown by Black Squares.

FIG. 5 Statistical Analysis of the Screening Data vs Sequencing of Clones from Libraries ME374, ME375 and ME368.

Screening of 22 Clones from TAB2.4 CCM in Quadruplicate. The Data Shows the Ratio of the Value for the Clone Over TAB2.4 (WT) for Expression, BSM Binding and Off-rate. The Mutations Contained in Each Clone Is Used as Label.

Western Blot Using an Anti-BLA Antibody for Various TAB2.4 Variants From the Screening of CCM Typical SDS-PAGE of Purified Monomer of TAB2.4 After Endotoxin Removal. Lane 1: Molecular Weight Standard, Lanes 3-4; TAB2.4 Purified.

Binding of Various TAB Variants to Coated BSM.

Binding of TAB2.5 to Various Coated TAG-72 Antigens.

Binding of TAB2.4 and TAB2.5 to Coated BSM.

Off-rate of TAB2.4 and TAB2.5 to Coated BSM.

Competition of Binding of TAB2.5 to Coated TE by BSM, TE, CA72-4 and TAG-72 Multimer.

Screening Data for Binding to Coated BSM vs Input BLA Activity of Clones from Libraries ME384-ME387. Many Clones in the Libraries were Parent TAB2.5 and Are Shown by Black Squares. Clones Picked were as Similar as Possible to the TAB2.5 Average.

Effect of Thermolysin Treatment (1h at 37°C) on the BLA Activity of TAB2.5 and TAB2.7.

Effect of Thermolysin Treatment (1h at 37°C)
on the binding of TAB2.7 to Coated BSM.

Binding of TAB2.7 and pME403.3 to Coated BSM.

DSC Thermograms of TAB2.5 and TAB2.4.

FIG. 22 Immunohistochemistry of TAB2.5 on an Accumax A203 Colon Cancer Array (Petagen).

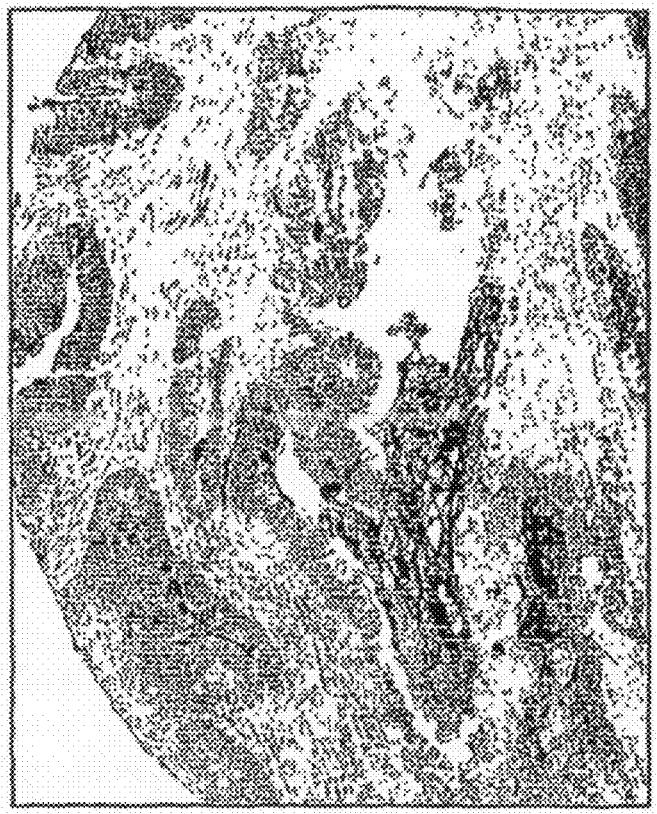
Immunohistochemistry of TAB2.5 on an Accumax A203 Colon Cancer Array (Petagen). Magnification of a Human Colon Adenocarcinoma.
FIG. 23

TAB2.4 Concentration-time Profiles in Mice.

Plasma TAB2.5 Concentration-time Profiles in rats.
Actual TAB2.5 Dose Each Rat Received: Rat 1=0.85 mg/kg,
rat 2=0.8 mg/kg, rat 3=0.4 mg/kg.

Efficacy Study of TAB2.5 in a LS174T Zenograph Mouse Model

Binding of Purified Monomer of TAB2.5 and TAB2.8 to Coated BSM or Tumor Extract.

TAB MOLECULES

CROSS-REFERENCE TO RELATED APPLICATIONS

The present application claims priority to U.S. Provisional Patent Application Ser. No. 60/675,728, entitled "TAB Molecules", filed Apr. 28, 2005.

FIELD OF THE INVENTION

The present invention relates to TAB molecules, ADEPT constructs directed against TAG-72 and their use in therapy.

BACKGROUND

Traditional non-targeted therapeutics circulate freely throughout the body of patients until removed from circulation. Such non-targeted molecules exert effects indiscriminately on a wide range of cells and tissues, which can cause serious side effects. When the therapeutic is toxic (e.g., a chemotherapeutic, where the "therapeutic window," the difference between an efficacious and injurious or even lethal dose, is small), the problem is particularly acute.

Researchers have attempted to develop therapeutics specific for a particular tissue. Most target particular tissues by preferentially binding a target displayed by the tissue. By targeting diseased tissues, the therapeutic window it increased and side effects reduced.

Preferential binding is employed in antibody-directed enzyme prodrug therapy ((ADEPT); See, e.g., Xu et al., 2001, Clin Cancer Res. 7:3314-24; Denny, 2001, Eur J Med Chem. 36:577-95). In ADEPT, an antibody or antibody fragment is linked to an enzyme capable of converting an inactive prodrug into an active cytotoxic, producing an ADEPT conjugate. The conjugate is administered to the patient and localizes to a target tissue via antibody/antigen binding. An inactive prodrug is subsequently administered, and the prodrug circulates throughout the patient's body, but causes few or no side effects because the prodrug is inactive until activated by the conjugate only in the vicinity of the tissue. Thus, the therapeutic window of the toxin is increased at the desired site, as a relatively low concentration of active drug is present throughout the body, but a relatively high concentration of active drug is produced in the vicinity of the target tissue.

In ADEPT, selecting the proper antigen is important (e.g., an antigen that has a high tumor/normal expression profile). A tumor antigen of particular interest is TAG-72, frequently found on the cell surface in cancer tissues. TAG-72 is mainly a carbohydrate epitope expressed on a variety of human adenocarcinomas, but showing low expression in most normal tissues [Cao, Y., P. Stosiek, G. F. Springer and U. Karsten (1996) *Histochem Cell Biol* 106, 197-207, Thomsen-Friedenreich-related carbohydrate antigens in normal adult human tissues: a systematic and comparative study].

SUMMARY OF THE INVENTION

The present invention relates to TAB molecules, ADEPT constructs directed against TAG-72 and their use in therapy, especially with prodrugs as described herein. The molecules of the current invention have been preferably deimmunized and do not elicit an immune response and can be produced in high yield. In a first aspect, the TAB molecule comprises an antibody/enzyme conjugate. In a preferred embodiment, the TAB molecule comprises an scFv, and the scFv has an unmodified amino acid sequence, the amino acid sequence comprising the sequence set forth in SEQ ID NO: 2. In a preferred embodiment, the TAB molecule has an amino acid sequence modified from the amino acid sequence set forth in SEQ ID NO: 2, the modification comprising at least one position selected from group consisting of: h8, h57, h62, h80, l5, l53, l79 and l105, the h and l in front of each designated position denoting a heavy or light chain, respectively, wherein numbering is with respect to the scFv set forth in SEQ ID NO: 2 based on the Kabat system (see, for example, Wu, T. T. and E. A. Kabat (1970) J. Exp. Med. 132, 211-250). In a preferred embodiment, the TAB molecule is modified at the following positions: h80, l5, l53 and l79. In a preferred embodiment, the TAB molecule has the following modifications: hV80L, lS5T, lA53T and lK79E. In a preferred embodiment, the TAB molecule comprises a TAB2.4, TAB2.5 or TAB2.8 molecule, the TAB2.4, TAB2.5 or TAB2.8 molecule comprising SEQ ID NO: 2, SEQ ID NO: 20 or SEQ ID NO: 22, respectively.

In a preferred embodiment, the TAB molecule further comprises an enzyme. In a preferred embodiment, the enzyme comprises a BLA.

In a preferred embodiment, the TAB molecule comprises a full-length antibody/enzyme TAB conjugate, and the scFv has an unmodified amino acid sequence, the amino acid sequence comprising the sequence set forth in SEQ ID NO: 6, SEQ ID NO: 8 or SEQ ID NO: 12. In a preferred embodiment, the TAB molecule has an amino acid sequence modified from the amino acid sequence set forth in SEQ ID NO: 8, the modification comprising at least one position selected from group consisting of: h8, h57, h62, h80, l5, l53, l79 and l105, the h and l in front of each designated position denoting a heavy or light chain, respectively, wherein numbering is with respect to the scFv set forth in SEQ ID NO: 2, based on the Kabat system (see, for example, Wu, T. T. and E. A. Kabat (1970) J. Exp. Med. 132, 211-250). In a preferred embodiment, the TAB molecule is modified at the following positions: h80, l5, l53 and l79. In a preferred embodiment, the TAB molecule has the following modifications: hV80L, lS5T, lA53T and lK79E. In a preferred embodiment, the TAB molecule comprises a TAB2.4, TAB2.5 or TAB2.8 molecule, the TAB2.4, TAB2.5 or TAB2.8 molecule comprising SEQ ID NO: 8, SEQ ID NO: 10 or SEQ ID NO:16, respectively.

In a preferred embodiment, the molecule comprises TAB2.6 having SEQ ID NO: 12. In a preferred embodiment, the molecule comprises clone ME374.4, ME375.18, ME374.31, ME374.63, ME374.73 or ME375.69.

In a second aspect, the invention is drawn to a nucleic acid encoding a TAB conjugate as set forth in any of the embodiments of the first Aspect, as well as those provided in the description, herein. In a preferred embodiment, the molecule is a nucleic acid comprising one of the following sequences: SEQ ID NO: 7, SEQ ID NO: 9, SEQ ID NO: 11 or SEQ ID NO: 13.

In a third aspect, the invention is drawn to treating a subject in need thereof, comprising administering to the subject a TAB molecule, as provided herein, and a prodrug that is a substrate of the TAB molecule. In a fourth aspect, the invention is drawn to a pharmaceutical composition comprising a TAB molecule.

BRIEF DESCRIPTION OF THE FIGURES

FIG. 1 shows relevant amino acid sequences set forth in the invention. FIG. 1A shows the amino acid sequence for TAB2.4 (SEQ ID NO: 8). The vH and vL sequences are underlined, the linker between vH and vL is in bold. FIG. 1B shows the protein sequence for CC49 (SEQ ID NO: 3). FIG.

1C sets forth the BLA portion of TAB2. FIG. 1D sets forth the amino acid sequence for TAB2.1 (SEQ ID NO: 6). FIG. 1E sets forth the DNA sequence for TAB2.1 (SEQ ID NO: 5). FIG. 1F sets forth the amino acid sequence for TAB2.4 (SEQ ID NO: 8). FIG. 1G sets forth the nucleotide sequence for TAB2.4 (SEQ ID NO: 7). FIG. 1H sets forth the amino acid sequence for TAB2.5 (SEQ ID NO: 10). FIG. 1I sets forth the nucleotide sequence for TAB2.5 (SEQ ID NO: 9). FIG. 1J sets forth the amino acid sequence for TAB 2.6 (SEQ ID NO: 12). FIG. 1K sets forth the nucleotide sequence for TAB2.6 (SEQ ID NO: 11). FIG. 1L sets forth the amino acid sequence for TAB2.7 (SEQ ID NO: 14). FIG. 1M sets forth the nucleotide sequence for TAB2.7 (SEQ ID NO: 13). FIG. 1N sets forth the amino acid sequence for the pME403.3 protein (SEQ ID NO: 18). FIG. 1O sets forth the nucleotide sequence encoding the pME403.3 protein (SEQ ID NO: 17). FIGS. 1P and 1Q set forth the amino acid and nucleotide sequences, respectively, for the TAB2.8 molecule (SEQ ID NO: 16 and SEQ ID NO: 15, respectively).

FI

3=0.4 mg/kg. The x-axis shows time in hours, and the y-axis shows TAB2.5 concentration in µg/ml.

Figure 26:
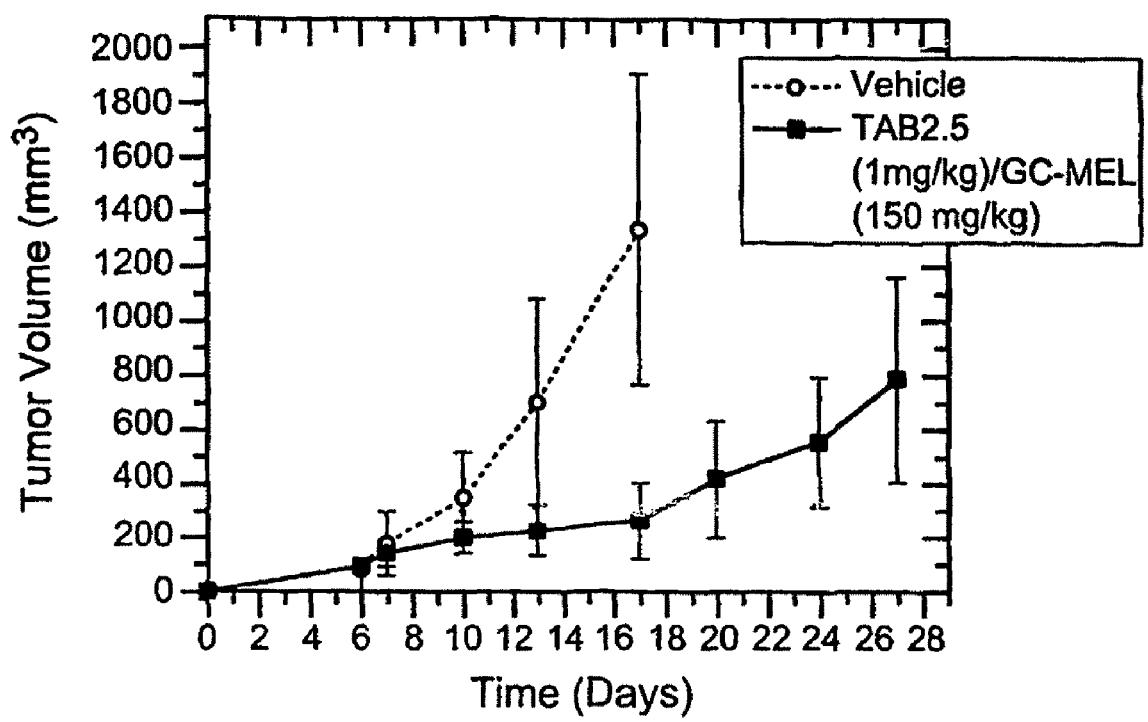

FIG. 26 shows an efficacy study of TAB2.5 in an LS174T xenograph mouse model, as set forth in Example 16. The x-axis shows time in days, and the y-axis shows tumor volume, measured in mm$^3$.

Figure 27:
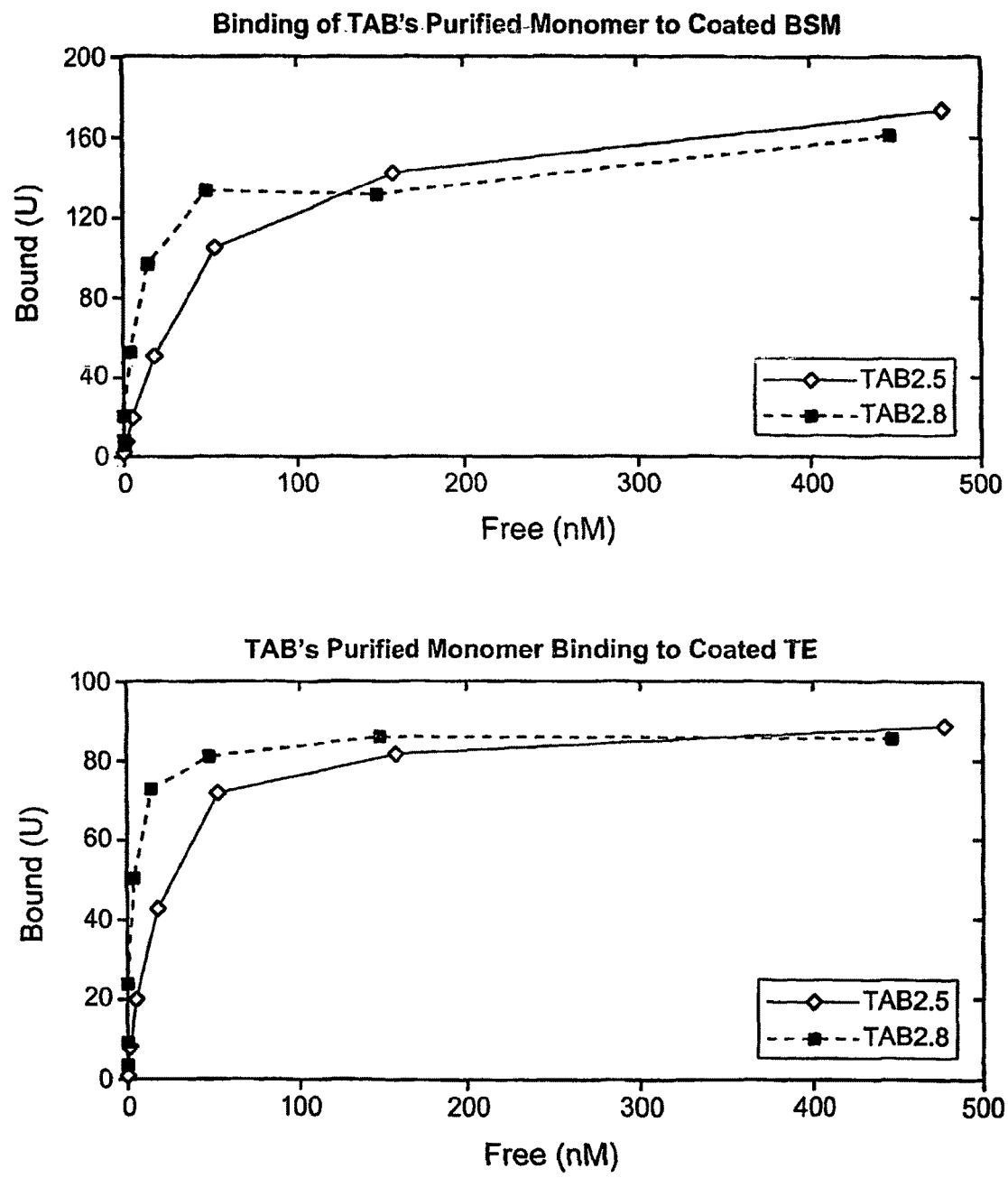

FIG. 27 shows TAB2.8 binding, as set forth in Example 18.

DETAILED DESCRIPTION OF THE INVENTION

Unless defined otherwise, all technical and scientific terms used have the same meaning as commonly understood by one of ordinary skill in the art to which this invention belongs. Although any methods and materials similar or equivalent to those described can be used in the practice or testing of the present invention, the preferred methods and materials are described. For purposes of the present invention, the following terms are used as described below.

As used herein, "conjugate" shall mean an ADEPT molecule that binds selectively to an antigen of interest. Examples of conjugates are antibody or antibody fragments conjugated to an enzyme of particular interest, for example a BLA, as set forth herein.

As used herein, "antigen" is a chemical structure recognized by an antibody, also sometimes referred to as an epitope. Of particular interest are tumor associated antigens, sometimes referred to as TAAs.

As used herein, "target" shall mean a group of cells, a tissue, an organ, cancer cells or tumor tissue. In that sense, a target is a region of the body to which one would like to specifically deliver compounds, for example as specifically set forth herein.

"TAB" molecule shall mean a conjugate that binds to a TAG-72 antigen ("TAG-72"). A TAB molecule may have an unmodified sequence or a modified sequence, wherein the unmodified sequence comprises the amino acid sequence set forth in SEQ ID NO: 2. The unmodified or modified sequence can also include BLA.

As used herein, an "unmodified" sequence shall refer to a sequence that has not been modified, either comprising an scFv or comprising an entire conjugate.

A "modified" sequence refers to a sequence that includes at least one mutation with respect to an unmodified sequence, as set forth above. Position numbering shall be with respect to the particular embodiment described. For example, relative position numbering with respect to an scFv is often with respect to SEQ ID NO: 2, as provided above. Likewise, for example, relative position numbering in this document with respect to the entire conjugate is often with respect to SEQ ID NO: 8. The relative position of an amino acid or mutation in an antibody or antibody fragment is often described by the Kabat numbering system [Wu, T. T. and Kabat, E. A. (1970) Biochem J 250, 753-760. Sequence and comparative analysis of three Enterobacter cloacae amp-C beta-lactamase genes and their products].

As used herein, "BLA" shall mean a protein that is able to cleave lactam or cephalosporin structures. Of particular interest are BLAs that can activate prodrugs that contain a lactam or cephalosporin structure. For example, BLA from Enterobacter cloacae are of interest, as well as homologs [see, for example, Galleni, M., Lindberg, F., Normark S., Cole. S., Honore, N., Joris, B. and Frere, J. M. (1988). Sequence and comparative analysis of three Enterobacter cloacae ampC beta-lactamase genes and their products. Biochem J. 250, 753-760) as well as TEM-4 lactamase [Sirot, D. (1995) Extended-spectrum plasmid-mediated beta-lactamases] and enzymes homologous to TEM-4.

BLA has been reported to activate a variety of prodrugs to release commonly used cancer drugs such as doxorubicin [Vrudhula, V. M., H. P. Svensson and P. D. Senter (1995) J Med Chem 38, 1380-5, Cephalosporin derivatives of doxorubicin as prodrugs for activation by monoclonal antibody-beta-lactamase conjugates], vinblastin [Meyer, D. L., L. N. Jungheim, K. L. Law, S. D. Mikolajczyk, T. A. Shepherd, D. G. Mackensen, S. L. Briggs and J. J. Starling (1993) Cancer Res 53, 3956-63, Site-specific prodrug activation by antibody-beta-lactamase conjugates: regression and long-term growth inhibition of human colon carcinoma xenograft models], paclitaxel [Vrudhula, V. M., D. E. Kerr, N. O. Siemers, G. M. Dubowchik and P. D. Senter (2003) Bioorg Med Chem Lett 13, 539-42, Cephalosporin prodrugs of paclitaxel for immunologically specific activation by L-49-sFv-beta-Lactamase fusion protein] and melphalan [Vrudhula, V. M., P. D. Senter, K. J. Fischer and P. M. Wallace (1993) J Med Chem 36, 919-23, Prodrugs of doxorubicin and melphalan and their activation by a monoclonal antibody-penicillin-G amidase conjugate].

A "binding moiety" is a part of an ADEPT construct, e.g., TAB molecule that binds a target. In the current invention, the binding moiety of a TAB molecule binds TAG72. A binding moiety can comprise more than one region, either contiguous or non-contiguous, of a TAB molecule.

An "active moiety" is a part of an ADEPT construct, e.g., TAB molecule that confers functionality to the agent. An active moiety can comprise more than one region, either contiguous or non-contiguous, of, for example, a TAB molecule. In particular, an active moiety can be an enzyme such as beta-lactamase.

The terms "cell", "cell line", and "cell culture" can be used interchangeably and all such designations include progeny. All progeny may not be precisely identical in DNA content, due to deliberate or inadvertent mutations. Mutant progeny that have the same functionality as screened for in the originally transformed cell are included in the definition of progeny or as transformants. The cells can be prokaryotic or eukaryotic.

The term "oligonucleotide" as used herein is defined as a molecule comprised of two or more deoxyribonucleotides or ribonucleotides. The exact size will depend on many factors, which in turn depends on the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Lett. 22:1859-1862; and the solid support method of U.S. Pat. No. 4,458,066, each incorporated herein by reference. A review of synthesis methods is provided in Goodchild, 1990, Bioconjugate Chemistry 1(3):165-187, incorporated herein by reference.

The term "primer" as used herein refers to an oligonucleotide capable of acting as a point of initiation of synthesis when placed under conditions in which primer extension is initiated. Synthesis of a primer extension product that is complementary to a nucleic acid strand is initiated in the presence of the requisite four different nucleoside triphosphates and a DNA polymerase in an appropriate buffer at a suitable temperature. A "buffer" includes a buffer, cofactors (such as divalent metal ions) and salt (to provide the appropriate ionic strength), adjusted to the desired pH.

A primer that hybridizes to the non-coding strand of a gene sequence (equivalently, is a subsequence of the noncoding strand) is referred to herein as an "upstream" or "forward" primer. A primer that hybridizes to the coding strand of a gene sequence is referred to herein as a "downstream" or "reverse" primer.

The term "protein" is used interchangeably here with the terms "peptide" and "polypeptide," and refers to a molecule comprising two or more amino acid residues joined by a peptide bond. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine), nonpolar side chains (e.g., alanine, valine, leucine, isoleucine, proline, phenylalanine, methionine, tryptophan, cysteine, glycine), beta-branched side chains (e.g., threonine, valine, isoleucine) and aromatic side chains (e.g., tyrosine, phenylalanine, tryptophan, histidine). Standard three-letter or one-letter amino acid abbreviations are used herein. Equivalent substitutions may be included within the scope of the claims.

The peptides, polypeptides and proteins of the invention can comprise one or more nonclassical amino acids. Nonclassical amino acids include but are not limited to the D-isomers of the common amino acids, α-amino isobutyric acid, 4-aminobutyric acid (4-Abu), 2-aminobutyric acid (2-Abu), 6-amino hexanoic acid (Ahx), 2-amino isobutyric acid (2-Aib), 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids and amino acid analogs in general.

The term "Ab" or "antibody" refers to polyclonal and monoclonal antibodies (MAb), chimeric antibodies, humanized antibodies, human antibodies, immunoglobulins or antibody or functional fragments of an antibody that bind to a target antigen. Examples of such functional entities include complete antibody molecules, antibody fragments, such as Fv, single chain Fv, complementarity determining regions (CDRs), VL (light chain variable region), VH (heavy chain variable region) and any combination of those or any other functional portion of an immunoglobulin peptide capable of binding to target antigen. Certain orders of portions are disclosed herein, but all orders are intended to be within the scope of the invention. For example, the TAB2.5 construct has the following order: vH-(GGGGS)6-vL (SEQ ID NO: 23); however, the example is non-limiting, and all orders of vL and vH, are contemplated to be within the scope of the invention.

As used herein, the term "linker" shall refer to a sequence of amino acids that joins two fragments of a TAB molecule. The fragments may be joined in any order, as set forth herein. Linker length may vary. The length of the linker need not be 30 amino acids in length, as disclosed herein, and different linker lengths are contemplated to be within the scope of the invention (e.g., the TAB 2.4 molecule has a linker length of 15 amino acids, and the TAB2.5 and TAB2.8 molecules have a linker length of 30 amino acids).

As used herein, a "linking structure" shall refer to a structure, which links two drug moieties. With respect to a prodrug, for example, a linker may also join an active to inactive moiety, the inactive moiety being removed enzymatically or spontaneously, for example, after cleavage or removal of the inactive moiety [see, for example, Papot, S. Tranoy, I. Tillequin, Florent, J. C., Gesson, J. P. (2002) Design of selectively activated anticancer prodrugs: elimination and cyclization strategies *Curr. Med. Chem. Anti-Canc Agents* 2, 155-185].

The term "prodrug" refers to a compound that is converted via one or more enzymatically-catalyzed or physiologically-catalyzed steps into an active compound that has an increased pharmacological activity relative to the prodrug. A prodrug can comprise a propart, or inactive moiety, and an active drug part or detectable moiety. Optionally, the prodrug also contains a linking structure. For example, the prodrug can be cleaved by an enzyme to release an active drug. Alternatively, an enzyme could alter the prodrug to release a detectable moiety useful, for example, as a diagnostic. In a more specific example, prodrug cleavage by the targeted enzyme releases the active drug into the vicinity of the target bound to the targeted enzyme. "Pro-part" and "inactive moiety" refers to the inactive portion of the prodrug after it has been converted.

As used herein, "GC-Mel" shall refer to the prodrug glutaryl-cephalosporin-melphalan as disclosed, for example, in Senter et al., U.S. Pat. No. 5,773,435, which is incorporated by reference herein, including any drawings.

As used herein, "Mel" shall mean Melphalan. The structure of Mel is well known in the art and can also be found in U.S. Pat. No. 5,773,435, incorporated by reference herein including any drawings.

Prodrugs can be designed to release a variety of drugs, including doxorubicin, vinblastin, paclitaxel, duocarmycin, camptothecin, alkylating drugs, topoisomerase inhibitors, platinum compounds and other drugs. Of particular interest are prodrugs that can be activated by lactamases [see, for example, Senter, P. D., and Springer, C. J. (2001) Selective activation of anticancer prodrugs by monoclonal antibody-enzyme conjugates *Adv Drug Deliv Res* 53, 247-264]. Other examples of prodrugs activated by various enzymes are known [see, Bagshawe, K. D., Sharma, S. K., Burke, P. J., Melton, R. G. and Knox, J. (1999) Developments with targeted enzymes in cancer therapy; also see, Niculescu-Duvaz, I., Friedlos, D., Niculescu-Duvez, D., Davies L. and Springer, C. J. (1999) Prodrugs for antibody and gene-directed enzyme prodrug therapies (ADEPT and ADEPT) *Anticancer Drug Des* 14, 517-538].

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art.

As used herein, "dosing interval" shall mean the interval between administration of the protein and subsequent administration of the pro-drug.

The term "% sequence homology" is used interchangeably herein with the terms "% homology," "% sequence identity" and "% identity" and refers to the level of amino acid sequence identity between two or more peptide sequences, when aligned using a sequence alignment program. For example, as used herein 80% homology means the same thing as 80% sequence identity determined by a defined algorithm, and accordingly, a homologue of a given sequence has greater than 80% sequence identity over a length of the given sequence. Exemplary levels of sequence identity include, but are not limited to, 60, 70, 80, 85, 90, 95, 98 or 99% or more sequence identity to a given sequence.

Exemplary computer programs that can be used to determine identity between two sequences include, but are not limited to, the suite of BLAST programs, e.g., BLASTN, BLASTX, and TBLASTX, BLASTP and TBLASTN, which are well-known to one skilled and the art. See also Altschul et al., 1990, *J. Mol. Biol.* 215: 403-10 and Altschul et al., 1997, *Nucleic Acids Res.*, 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See Altschul, et al., 1997.

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

The present invention relates to TAB molecules, ADEPT constructs directed against TAG-72, and their use in therapy, especially with prodrugs as described herein. The molecules of the current invention have been preferably deimmunized and do not elicit an immune response.

In a first aspect, the TAB molecule comprises an antibody/enzyme conjugate. In a preferred embodiment, the TAB molecule comprises an scFv, and the scFv has an unmodified amino acid sequence, the amino acid sequence comprising the sequence set forth in SEQ ID NO: 2. In a preferred embodiment, the TAB molecule has an amino acid sequence modified from the amino acid sequence set forth in SEQ ID NO: 2, the modification comprising at least one position selected from group consisting of: h8, h57, h62, h80, l5, l53, l79 and l105, the h and l in front of each designated position denoting a heavy or light chain, respectively, wherein numbering is with respect to the scFv set forth in SEQ ID NO: 2, based on the Kabat system (see, for example, Wu, T. T. and E. A. Kabat (1970) *J. Exp. Med.* 132, 211-250). In a preferred embodiment, the TAB molecule is modified at the following positions: h80, l5, l53, and l79. In a preferred embodiment, the TAB molecule has the following modifications: hV80L, lS5T, lA53T and lK79E. In a preferred embodiment, the TAB molecule comprises a TAB2.4, TAB2.5 or TAB2.8 molecule, the TAB2.4, TAB2.5 or TAB2.8 molecule comprising SEQ ID NO: 2, SEQ ID NO: 20 or SEQ ID NO: 22, respectively.

In a preferred embodiment, the TAB molecule further comprises an enzyme. In a preferred embodiment, the enzyme comprises a BLA. In a preferred embodiment, the BLA comprises TEM-4.

In a preferred embodiment, the TAB molecule comprises a full-length antibody/enzyme TAB conjugate, and the scFv has an unmodified amino acid sequence, the amino acid sequence comprising the sequence set forth in SEQ ID NO: 2. In a preferred embodiment, the TAB molecule has an amino acid sequence modified from the amino acid sequence set forth in SEQ ID NO: 8, the modification comprising at least one position selected from group consisting of: h8, h57, h62, h80, l5, l53, l79 and l105, the h and l in front of each designated position denoting a heavy or light chain, respectively, wherein numbering is with respect to the scFv set forth in SEQ ID NO: 2, based on the Kabat system as set forth herein. In a preferred embodiment, the TAB molecule is modified at the following positions: h80, l5, l53 and l79. In a preferred embodiment, the TAB molecule has the following modifications: hV80L, lS5T, lA53T and lK79E. In a preferred embodiment, the TAB molecule comprises a TAB2.4, TAB2.5 or TAB2.8 molecule, the TAB2.4, TAB2.5 or TAB2.8 molecule comprising SEQ ID NO: 8, SEQ ID NO: 10 or TAB: 16, respectively.

In a preferred embodiment, the molecule comprises TAB2.6 having SEQ ID NO: 12. In a preferred embodiment, the molecule comprises clone ME374.4, ME375.18, ME374.31, ME74.63, ME374.73 or ME375.69.

In another embodiment, the TAB is a milieu-dependent targeted agent as described in PCT Application Number US03/18200, filed Jun. 12, 2002 and incorporated herein by reference in its entirety. TAP, molecules of the present invention may be shown to preferentially bind to a target relative to a non-target under differing mileaus between the target and the non-target. The difference in binding can be caused by any difference between the target and non-target such as, for example a difference in pH, oxygen pressure, concentration of solutes or analytes (e.g., lactic acid, sugars or other organic or inorganic molecules), temperature, light or ionic strength. Preferential binding of the TABs of the current invention can be used to bind to a target under a desired set of conditions, identify a target in vitro, ex vivo, in situ or in vivo (e.g., a target tissue in a subject), kill a target cell or tissue or convert a prodrug into an active drug in or near a target tissue.

In one embodiment, the TAB is selected, made or modified using an affinity maturation method, e.g., as described in PCT application US03/18187, with a priority date filed Jun. 12, 2002 and incorporated herein by reference in its entirety.

In another embodiment, the TAB is selected, made or modified using a loop-grafting method, e.g., as described in U.S. patent application Ser. No. 10/170,387, filed Jun. 12, 2002 and incorporated herein by reference in its entirety.

In another embodiment, the TAB is a multifunctional polypeptide, e.g., as described in U.S. patent application Ser. No. 10/170,729, filed Jun. 12, 2002 and incorporated herein by reference in its entirety.

In another embodiment, the TABs of the current invention are used for diagnostic or therapeutic applications such as those disclosed, for example, in U.S. Pat. No. 4,975,278, which is incorporated herein by reference in its entirety, as well as methods well-known in the art.

In one embodiment, the TAB molecule further comprises an active moiety. The active moiety can be any molecule, or a part of a molecule, that has an activity. The activity can be any activity. Examples of types of activities that the active moiety can have include, for example, a detectable activity, an enzymatic activity, a therapeutic activity, a diagnostic activity, a toxic activity or a binding activity. The active moiety can be a discrete part of the TAB, for example, an enzyme that is fused or conjugated to the binding moiety, or it can be an integral part of the TAB, for example, binding of the TAB to the target can activate or inhibit an activity of the target.

In another embodiment, the active moiety exhibits enzymatic activity, e.g., it is an enzyme or an active fragment or derivative of an enzyme. Of particular interest are enzymes that can be used to activate a prodrug in a therapeutic setting. A large number of enzymes with different catalytic modes of action have been used to activate prodrugs. See, e.g., Melton & Knox Enzyme-prodrug strategies for cancer therapy (1999) and Bagshawe et al., *Curr Opin Immunol* 11:579 (1999). Examples of types of enzymes that can be used to make the TABs of the present invention include, but are not limited to, proteases, carboxypeptidases, β-lactamases, asparaginases, oxidases, hydrolases, lyases, lipases, cellulases, amylases, aldolases, phosphatases, kinases, transferases, polymerases, nucleases, nucleotidases, laccases, reductases, and the like. (See, e.g., co-pending U.S. patent application Ser. No. 09/954,385, filed Sep. 12, 2001, incorporated herein by reference in its entirety.) As such, TABs of the invention can, for example, exhibit protease, carboxypeptidase, β-lactamase, asparaginase, oxidase, hydrolase, lyase, lipase, cellulase, amylase, aldolase, phosphatase, kinase, tranferase, polymerase, nuclease, nucleotidase, laccase or reductase activity or the like. Examples of enzymes that can be used are those that can activate a prodrug, discussed below, and those that can produce a toxic agent from a metabolite, e.g., hydrogen peroxide from glucose. See Christofidou-Solomidou et al, 2000, *Am J Physiol Lung Cell Mol Physiol* 278:L794.

In one embodiment, the present invention provides a TAB further comprising a β-lactamase ("BLA"). A representative BLA sequence is depicted in FIG. 1.

BLA enzymes are widely distributed in both gram-negative and gram-positive bacteria. BLA sequences are well known. A representative example of a BLA sequence is depicted in SEQ ID NO: 4. BLA enzymes vary in specificity, but have in common that they hydrolyze β-lactams, producing substituted β-amino acids. Thus, they confer resistance to antibiotics containing β-lactams. Because BLA enzymes are not endogenous to mammals, they are subject to minimal interference from inhibitors, enzyme substrates, or endogenous enzyme systems (unlike proteases), and therefore are particularly well-suited for therapeutic administration. BLA enzymes are further well-suited to the therapeutic methods of the present invention because of their small size (BLA from *E. cloacae* is a monomer of 39 kD; BLA from *E. coli* is a monomer of 30 kD) and because they have a high specific activity against their substrates and have optimal activity at 37° C. See Melton et al., Enzyme-Prodrug Strategies for Cancer Therapy, Kluwer Academic/Plenum Publishers, New York (1999).

Examples of specific BLAs that can be used to make the TABs of the present invention include, but are not limited to, Class A, B, C or D β-lactamase, β-galactosidase, (see Benito et al., *FEMS Microbiol. Let.* 123:107 (1994)), fibronectin, glucose oxidase, glutathione S-transferase, see Napolitano et al., *Chem. Biol.* 3:359 (1996) and tissue plasminogen activator, see Smith et al., *J. Biol. Chem.* 270:30486 (1995). The β-lactamases have been divided into four classes based on their sequences. See Thomson et al., 2000, *Microbes and Infection* 2:1225-35. The serine β-lactamases are subdivided into three classes: A (penicillinases), C (cephalosporinases) and D (oxacillnases). Class B β-lactamases are the zinc-containing or metallo β-lactamases. Any class of BLA can be utilized to generate a TAB of the invention.

In one embodiment, the BLA has a measurable specific activity. In one embodiment of the invention, the BLA has a specific activity greater than about 0.01 U/pmol against nitrocefin using the assay described in U.S. patent application Ser. No. 10/022,097. In another embodiment, the specific activity is greater than about 0.1 U/pmol. In another embodiment, the specific activity is greater than about 1 U/pmol. Preferably, these specific activities refer to the specific activity of the BLA when it is bound to a target.

In one embodiment, the BLA enzyme in the TAB comprises the amino acid sequence set forth in SEQ ID NO: 4. In another embodiment, the BLA enzyme in the TAB is at least 50%, 60%, 70%, 80%, 90%, 95%, 98% or 99% or more identical to the sequence depicted in SEQ ID NO: 4.

The targets bound by the TAB, or one or more binding moieties, can be any substance or composition to which a molecule can be made to bind to TAG-72. In one embodiment, the target is a surface. In one embodiment, the surface is a biological surface. In another embodiment, the biological surface is a surface of an organ. In another embodiment, the biological surface is a surface of a tissue. In another embodiment, the biological surface is a surface of a cell. In another embodiment, the biological surface is a surface of a diseased organ, tissue or cell. In another embodiment, the biological surface is a surface of a normal or healthy organ, tissue or cell. In another embodiment, the surface is a macromolecule in the interstitial space of a tissue. In another embodiment, the biological surface is the surface of a virus or pathogen. In another embodiment, the surface is a non-biological surface. In another embodiment, the non-biological surface is a surface of a medical device. In another embodiment, the medical device is a therapeutic device. In another embodiment, the therapeutic device is an implanted therapeutic devices. In another embodiment, the medical device is a diagnostic device. In another embodiment, the diagnostic device is a well or tray.

Tissues are complex targets and refer to a single cell type, a collection of cell types or an aggregate of cells generally of a particular kind. Tissue may be intact or modified. General classes of tissue in humans include, but are not limited to, epithelial tissue, connective tissue, nerve tissue and muscle tissue.

In another embodiment, the target is a cancer-related target that expresses the antigen TAG-72 or that has TAG-72 bound to itself or that has TAG-72 located in its vicinity. The cancer-related target can be any target that a composition of the invention binds to as part of the diagnosis, detection or treatment of a cancer or cancer-associated condition in a subject, for example, a cancerous cell, tissue or organ, a molecule associated with a cancerous cell, issue or organ, or a molecule, cell, tissue or organ that is associated with a cancerous cell, tissue or organ (e.g., a tumor-bound diagnostic or therapeutic molecule administered to a subject or to a biopsy taken from a subject, or a healthy tissue, such as vasculature, that is associated with cancerous tissue).

In a second aspect, the invention is drawn to a nucleic acid encoding a TAB conjugate as set forth in any of the embodiments of the first aspect, as well as those provided in the description, herein. In a preferred embodiment, the nucleic acid comprises at least one of the following sequences: SEQ ID NO: 7, SEQ ID NO: 9, SEQ ID NO: 15 or SEQ ID NO: 11. In a preferred embodiment, the nucleic acid comprises SEQ ID NO: 13.

The nucleic acid can be, for example, a DNA or an RNA. The present invention also provides a plasmid comprising a nucleic acid encoding a polypeptide comprising all or part of a TAB. The plasmid can be, for example, an expression plasmid that allows expression of the polypeptide in a host cell or organism, or in vitro. The expression vector can allow expression of the polypeptide in, for example, a bacterial cell. The bacterial cell can be, for example, an *E. coli* cell.

Because of the redundancy in the genetic code, typically a large number of DNA sequences encode any given amino acid sequence and are, in this sense, equivalent. As described below, it may be desirable to select one or another equivalent DNA sequences for use in an expression vector, based on the preferred codon usage of the host cell into which the expression vector will be inserted. The present invention is intended to encompass all DNA sequences that encode the desired TAB.

An operable expression clone may be used and is constructed by placing the coding sequence in operable linkage with a suitable control sequence in an expression vector. The vector can be designed to replicate autonomously in the host cell or to integrate into the chromosomal DNA of the host cell. The resulting clone is used to transform a suitable host, and the transformed host is cultured under conditions suitable for expression of the coding sequence. The expressed TAB is then isolated from the medium or from the cells, although recovery and purification of the TAB may not be necessary in some instances.

Construction of suitable clones containing the coding sequence and a suitable control sequence employ standard ligation and restriction techniques that are well understood in the art. In general, isolated plasmids, DNA sequences or synthesized oligonucleotides are cleaved, modified and religated in the form desired. Suitable restriction sites can, if not normally available, be added to the ends of the coding sequence so as to facilitate construction of an expression clone.

Site-specific DNA cleavage is performed by treating with a suitable restriction enzyme (or enzymes) under conditions that are generally understood in the art and specified by the manufacturers of commercially available restriction enzymes. See, e.g., product catalogs from Amersham (Arlington Heights, Ill.), Roche Molecular Biochemicals (Indianapolis, Ind.), and New England Biolabs (Beverly, Mass.). Incubation times of about one to two hours at a temperature that is optimal for the particular enzyme are typical. After each incubation, protein is removed by extraction with phenol and chloroform; this extraction can be followed by ether extraction and recovery of the DNA from aqueous fractions by precipitation with ethanol. If desired, size separation of the cleaved fragments may be performed by polyacrylamide gel or agarose gel electrophoresis using standard techniques. See, e.g., Maxam et al., 1980, Methods in Enzymology 65:499-560.

Ligations can be performed, for example, in 15-30 μl volumes under the following standard conditions and temperatures: 20 mM Tris-Cl, pH 7.5, 10 mM $MgCl_2$, 10 mM DTT, 33 μg/ml BSA, 10-50 mM NaCl, and either 40 μM ATP and 0.01-0.02 (Weiss) units T4 DNA ligase at 0° C. (for ligation of fragments with complementary single-stranded ends) or 1 mM ATP and 0.3-0.6 units T4 DNA ligase at 14° C. (for "blunt end" ligation). Intermolecular ligations of fragments with complementary ends are usually performed at 33-100 μg/ml total DNA concentrations (5-100 nM total ends concentration). Intermolecular blunt end ligations (usually employing a 20-30 fold molar excess of linkers, optionally) are performed at 1 μM total ends concentration.

Correct ligations for plasmid construction can be confirmed using any suitable method known in the art. For example, correct ligations for plasmid construction can be confirmed by first transforming a suitable host, such as E. coli strain DG101 (ATCC 47043) or E. coli strain DG116 (ATCC 53606), with the ligation mixture. Successful transformants are selected by ampicillin, tetracycline or other antibiotic resistance or sensitivity or by using other markers, depending on the mode of plasmid construction, as is understood in the art. Plasmids from the transformants are then prepared according to the method of Clewell et al., 1969, Proc. Natl. Acad. Sci. USA 62:1159, optionally following chloramphenicol amplification. See Clewell, 1972, J. Bacteriol. 110: 667. Alternatively, plasmid DNA can be prepared using the "Base-Acid" extraction method at page 11 of the Bethesda Research Laboratories publication Focus 5 (2), and very pure plasmid DNA can be obtained by replacing steps 12 through 17 of the protocol with CsCl/ethidium bromide ultracentrifugation of the DNA. As another alternative, a commercially available plasmid DNA isolation kit, e.g., HISPEED™, QIAFILTER™ and QIAGEN® plasmid DNA isolation kits (Qiagen, Valencia Calif.) can be employed following the protocols supplied by the vendor. The isolated DNA can be analyzed by, for example, restriction enzyme digestion and/or sequenced by the dideoxy method of Sanger et al., 1977, Proc. Natl. Acad. Sci. USA 74:5463, as further described by Messing et al., 1981, Nuc. Acids Res. 9:309, or by the method of Maxam et al., 1980, Methods in Enzymology 65:499.

The control sequences, expression vectors and transformation methods are dependent on the type of host cell used to express the gene. Generally, prokaryotic, yeast, insect or mammalian cells are used as hosts. Prokaryotic hosts are in general the most efficient and convenient for the production of recombinant proteins and are therefore preferred for the expression of the protein.

The prokaryote most frequently used to express recombinant proteins is E. coli. However, microbial strains other than E. coli can also be used, such as bacilli, for example Bacillus subtilis, various species of Pseudomonas and Salmonella, and other bacterial strains. In such prokaryotic systems, plasmid vectors that contain replication sites and control sequences derived from the host or a species compatible with the host are typically used.

For expression of constructions under control of most bacterial promoters, E. coli K12 strain MM294, obtained from the E. coli Genetic Stock Center under GCSC #6135, can be used as the host. For expression vectors with the $P_L N_{RBS}$ or $P_L T7_{RBS}$ control sequence, E. coli K12 strain MC1000 lambda lysogen, $N_7 N_{53} cI857$ $SusP_{80}$, ATCC 39531, may be used. E. coli DG116, which was deposited with the ATCC (ATCC 53606) on Apr. 7, 1987, and E. coli KB2, which was deposited with the ATCC (ATCC 53075) on Mar. 29, 1985, are also useful host cells. For M13 phage recombinants, E. coli strains susceptible to phage infection, such as E. coli K12 strain DG98 (ATCC 39768), are employed. The DG98 strain was deposited with the ATCC on Jul. 13, 1984.

E. coli is typically transformed using derivatives of pBR322, described by Bolivar et al., 1977, Gene 2:95. Plasmid pBR322 contains genes for ampicillin and tetracycline resistance. These drug resistance markers can be either retained or destroyed in constructing the desired vector and so help to detect the presence of a desired recombinant. Commonly used prokaryotic control sequences, i.e., a promoter for transcription initiation, optionally with an operator, along with a ribosome binding site sequence, include the β-lactamase (penicillinase) and lactose (lac) promoter systems, see Chang et al., 1977, Nature 198:1056, the tryptophan (trp) promoter system, see Goeddel et al., 1980, Nuc. Acids Res. 8:4057, and the lambda-derived $P_L$ promoter, see Shimatake et al., 1981, Nature 292:128, and gene N ribosome binding site ($N_{RBS}$) A portable control system cassette is set forth in U.S. Pat. No. 4,711,845, issued Dec. 8, 1987. This cassette comprises a $P_L$ promoter operably linked to the $N_{RBS}$ in turn positioned upstream of a third DNA sequence having at least one restriction site that permits cleavage within six base pairs 3' of the $N_{RBS}$ sequence. Also useful is the phosphatase A (phoA) system described by Chang et al., in European Patent Publication No. 196,864, published Oct. 8, 1986. However, any available promoter system compatible with prokaryotes can be used to construct an expression vector of the invention.

In addition to bacteria, eukaryotic microbes, such as yeast, can also be used as recombinant host cells. Laboratory strains of Saccharomyces cerevisiae, Baker's yeast, are most often used, although a number of other strains are commonly available. While vectors employing the two micron origin of replication are common, see Broach, 1983, Meth. Enz. 101:307, other plasmid vectors suitable for yeast expression are known. See, e.g., Stinchcomb et al., 1979, Nature 282:39; Tschempe et al., 1980, Gene 10:157; and Clarke et al., 1983, Meth. Enz. 101:300. Control sequences for yeast vectors include promoters for the synthesis of glycolytic enzymes. See Hess et al., 1968, J. Adv. Enzyme Reg. 7:149; Holland et al., 1978, Biotechnology 17:4900; and Holland et al., 1981, J. Biol. Chem. 256:1385. Additional promoters known in the art include the promoter for 3-phosphoglycerate kinase, see Hitzeman et al., 1980, J. Biol. Chem. 255:2073, and those for other glycolytic enzymes, such as glyceraldehyde 3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase. Other promoters that have the additional advantage of transcription controlled by growth conditions are the promoter regions for alcohol dehydrogenase 2, isocytochrome C, acid phosphatase, degradative enzymes associated with nitrogen metabolism and enzymes responsible for maltose and galactose utilization.

Terminator sequences may also be used to enhance expression when placed at the 3' end of the coding sequence. Such terminators are found in the 3' untranslated region following the coding sequences in yeast-derived genes. Any vector containing a yeast-compatible promoter, origin of replication and other control sequences is suitable for use in constructing yeast expression vectors.

The coding sequence can also be expressed in eukaryotic host cell cultures derived from multicellular organisms. See, e.g., Tissue Culture, Academic Press, Cruz and Patterson, editors (1973). Useful host cell lines include COS-7, COS-A2, CV-1, murine cells such as murine myelomas N51 and VERO, HeLa cells and Chinese hamster ovary (CHO) cells. Expression vectors for such cells ordinarily include promoters and control sequences compatible with mammalian cells such as, for example, the commonly used early and late promoters from Simian Virus 40 (SV 40), see Fiers et al., 1978, Nature 273:113, or other viral promoters such as those derived from polyoma, adenovirus-2, bovine papilloma virus (BPV) or avian sarcoma viruses, or immunoglobulin promoters and heat shock promoters.

Enhancer regions are also important in optimizing expression; these are, generally, sequences found upstream of the promoter region. Origins of replication may be obtained, if needed, from viral sources. However, integration into the chromosome is a common mechanism for DNA replication in eukaryotes.

Plant cells can also be used as hosts, and control sequences compatible with plant cells, such as the nopaline synthase promoter and polyadenylation signal sequences, see Depicker et al., 1982, J. Mol. Appl. Gen. 1:561, are available. Expression systems employing insect cells utilizing the control systems provided by baculovirus vectors have also been described. See Miller et al., in Genetic Engineering (1986), Setlow et al., eds., Plenum Publishing, Vol. 8, pp. 277-97. Insect cell-based expression can be accomplished in *Spodoptera frugipeida*. These systems are also successful in producing recombinant enzymes.

Depending on the host cell used, transformation is done using standard techniques appropriate to such cells. The calcium treatment employing calcium chloride, as described by Cohen, 1972, Proc. Natl. Acad. Sci. USA 69:2110, is used for prokaryotes or other cells that contain substantial cell wall barriers. Infection with *Agrobacterium tumefaciens*, see Shaw et al., 1983, Gene 23:315, is used for certain plant cells. For mammalian cells, the calcium phosphate precipitation method of Graham et al., 1978, Virology 52:546 is preferred. Transformations into yeast are carried out according to the method of Van Solingen et al., 1977, J. Bact. 130:946, and Hsiao et al., 1979, Proc. Natl. Acad. Sci. USA 76:3829.

It may be desirable to modify the sequence of a DNA encoding a polypeptide comprising all or part of a TAB of the invention to provide, for example, a sequence more compatible with the codon usage of the host cell without modifying the amino acid sequence of the encoded protein. Such modifications to the initial 5-6 codons may improve expression efficiency. DNA sequences which have been modified to improve expression efficiency, but which encode the same amino acid sequence, are considered to be equivalent and encompassed by the present invention.

A variety of site-specific primer-directed mutagenesis methods are available and well-known in the art. See, e.g., Sambrook et al., Molecular Cloning: A Laboratory Manual, Cold Spring Harbor, 1989, second edition, chapter 15.51, "Oligonucleotide-mediated mutagenesis," which is incorporated herein by reference. The polymerase chain reaction (PCR) can be used to perform site-specific mutagenesis. In another technique now standard in the art, a synthetic oligonucleotide encoding the desired mutation is used as a primer to direct synthesis of a complementary nucleic acid sequence contained in a single stranded vector, such as pBSM13+ derivatives, that serves as a template for construction of the extension product of the mutagenizing primer. The mutagenized DNA is transformed into a host bacterium, and cultures of the transformed bacteria are plated and identified. The identification of modified vectors may involve transfer of the DNA of selected transformants to a nitrocellulose filter or other membrane and the "lifts" hybridized with kinased synthetic mutagenic primer at a temperature that permits hybridization of an exact match to the modified sequence but prevents hybridization with the original unmutagenized strand. Transformants that contain DNA that hybridizes with the probe are then cultured (the sequence of the DNA is generally confirmed by sequence analysis) and serve as a reservoir of the modified DNA.

Once the polypeptide has been expressed in a recombinant host cell, purification of the polypeptide may be desired. A variety of purification procedures can be used, such as those set forth in the Examples. Proteins can be purified by various chromatography methods like ion exchange chromatography, size exclusion chromatography, hydrophobic interaction chromatography and related techniques. In addition, proteins can be purified by precipitation of either the protein of interest itself or by selective precipitation of contaminating products using salts or other reagents that affect solubility. Proteins can also be purified by extraction.

In one embodiment, a nucleic acid encoding the TAB hybridizes to a nucleic acid complementary to a nucleic acid encoding any of the amino acid sequences disclosed herein under highly stringent conditions. The highly stringent conditions can be, for example, hybridization to filter-bound DNA in 0.5 M NaHPO$_4$, 7% sodium dodecyl sulfate (SDS), 1 mM EDTA at 65° C. and washing in 0.1×SSC/0.1% SDS at 68° C. (Ausubel et al., eds., 1989, *Current Protocols in Molecular Biology*, Vol. I, Green Publishing Associates, Inc., and John Wiley & Sons, Inc., New York, at p. 2.10.3). Other highly stringent conditions can be found in, for example, *Current Protocols in Molecular Biology*, at pages 2.10.1-16 and *Molecular Cloning: A Laboratory Manual,* 2d ed., Sambrook et al. (eds.), Cold Spring Harbor Laboratory Press, 1989, pages 9.47-57). In another embodiment, moderately stringent conditions are used. The moderately stringent conditions can be, for example, washing in 0.2×SSC/0.1% SDS at 42° C. (Ausubel et al., 1989, supra). Other moderately stringent conditions can be found in, for example, *Current Protocols in Molecular Biology*, Vol. I, Ausubel et al. (eds.), Green Publishing Associates, Inc., and John Wiley & Sons, Inc., 1989, pages 2.10.1-16 and *Molecular Cloning: A Labo-*

*ratory Manual*, 2d ed., Sambrook et al. (eds.), Cold Spring Harbor Laboratory Press, 1989, pages 9.47-57.

In a third aspect the present invention provides a method of treating a subject in need thereof comprising administering to a subject a TAB and a prodrug that is a substrate of the TAB. In another embodiment, the invention provides a method of treating a subject by administering to the subject a TAB molecule and a prodrug that is converted by the BLA into an active drug. In another embodiment, the TAB is specifically TAB2.4, TAB2.5 or TAB2.8 as set forth in SEQ ID NO: 8, SEQ ID NO: 10 or SEQ ID NO: 16, respectively.

Melphalan derivatives are especially suitable as the prodrug for this embodiment of the invention. Examples of enzyme/prodrug/active drug combinations can be found in, e.g., Senter et al., U.S. Pat. No. 5,773,435, which is incorporated by reference herein, including any drawings. Other examples of suitable prodrugs for this embodiment are provided in, e.g., Melton et al., Enzyme-Prodrug Strategies for Cancer Therapy, Kluwer Academic/Plenum Publishers, New York (1999), Bagshawe et al., *Current Opinion in Immunology* 11:579-83 (1999) and Kerr et al., *Bioconjugate Chem* 9:255-59 (1998). Wilman, "Prodrugs In Cancer Chemotherapy," *Biochemical Society Transactions*, 14, pp. 375-82 (615th Meeting, Belfast 1986) and V. J. Stella et al., "Prodrugs: A Chemical Approach To Targeted Drug Delivery," *Directed Drug Delivery*, R. Borchardt et al. (ed), pp. 24767 (Humana Press 1985).

The prodrugs of the invention can include, but are not limited to, auristatins, camptothecins, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide containing prodrugs, 5-fluorocytosine and other 5-fluorouridine prodrugs which can be converted by the enzyme of the conjugate into the more active cytotoxic free drug. Examples of cytotoxic drugs that can be derivatized into a prodrug form for use in this invention include, but are not limited to, etoposide, temposide, adriamycin, daunomycin, caminomycin, aminopterin, dactinomycin, mitomycins, cis-platinum and cis-platinum analogues, bleomycins, esperamicins (see U.S. Pat. No. 4,675,187), 5-fluorouracil, melphalan, other related nitrogen mustards and derivatives thereof. (See, e.g., U.S. Pat. No. 4,975,278).

In one embodiment of the invention, the TAB comprises an alkaline phosphatase (AP) that converts a 4'-phosphate derivative of the epipodophyl-lotoxin glucosides into an active anti-cancer drug. Such, derivatives include etoposide-4'-phosphate, etoposide-4'-thiophosphate and teniposide-4'-phosphate. Other embodiments of the invention may include phosphate derivatives of these glucosides wherein the phosphate moiety is placed at other hydroxyl groups on the glucosides. According to another embodiment, however, the phosphate derivative used as a pro-drug in this invention is etoposide-4'-phosphate or etoposide-4'-thiophosphate. The targeted AP removes the phosphate group from the prodrug, releasing an active antitumor agent. The mitomycin phosphate prodrug of this embodiment may be an $N^7$—$C_{1-8}$ alkyl phosphate derivative of mitomycin C or porfiromycin or pharmaceutically acceptable salts thereof. $N^7$ refers to the nitrogen atom attached to the 7-position of the mitosane nucleus of the parent drug. According to another embodiment, the derivative used is 7-(2'-aminoethylphosphate)mitomycin ("MOP"). Alternatively, the MOP compound may be termed, 9-methoxy-7-[[(phos-phonooxy)ethyl]amino]mitosane disodium salt. Other embodiments of the invention may include the use pf $N^7$-alkyl mitomycin phosphorothioates as prodrugs.

In still another embodiment of the invention, the TAB comprises a penicillin amidase enzyme that converts a novel adriamycin prodrug into the active antitumor drug adriamycin. In another embodiment, the penicillin amidase is a penicillin V amidase ("PVA") isolated from *Fusarium oxysporum* that hydrolyzes phenoxyacetyl amide bonds. The prodrug utilized can be N-(p-hydroxypbenoxyacetyl)adriamycin ("APO"), which is hydrolyzed by the amidase to release the potent antitumor agent or adriamycin.

The present invention also comprises, for example, the use of the adriamycin prodrug, N-(p-hydroxyphenoxyacetyl) adriamycin and other related adriamycin prodrugs that can be derivatized in substantially the same manner. For example, use of the prodrug N-(phenoxyacetyl)adriamycin is also within the scope of the invention. In addition, it is to be understood that the adriamycin prodrugs of this invention include other N-hydroxyphenoxyacetyl derivatives of adriamycin, e.g., substituted at different positions of the phenyl ring, as well as N-phenoxyacetyl derivatives containing substituents on the phenyl ring other than the hydroxyl group described herein.

Furthermore, the present embodiment encompasses the use of other amidases, such as penicillin G amidase, as part of TAB as well as other prodrugs correspondingly derivatized such that the particular amidase can hydrolyze that prodrug to an active antitumor form. For example, when the TAB further comprises penicillin G amidase, the prodrug should contain a phenylacetylamide group (as opposed to the phenoxyacetylamide group of APO) because penicillin G amidases hydrolyze this type of amide bond (see, e.g., A. L. Margolin et al., *Biochim Biophys Acta* 616, pp. 283-89 (1980)). Thus, other prodrugs of the invention include N-(p-hydroxyphenylacetyl) adriamycin, N-(phenylacetyl)adriamycin and other optionally substituted N-phenylacetyl derivatives of adriamycin.

It should also be understood that the present invention includes any prodrug derived by reacting the amine group of the parent drug with the carboxyl group of phenoxyacetic acid, phenylacetic acid or other related acids. Thus, prodrugs of anthracyclines other than adriamycin that are capable of being derivatized and acting in substantially the same manner as the adriamycin prodrugs described herein falls within the scope of this invention. For example, other prodrugs that can be produced and used in accordance with this invention include hydroxyphenoxyacetylamide derivatives, hydroxyphenylacetylamide derivatives, phenoxyacetylamide derivatives and phenylacetylamide derivatives of anthracyclines such as daunomycin and caminomycin. Other amine-containing drugs such as melphalan, mitomycin, aminopterin, bleomycin and dactinomycin can also be modified described herein to yield prodrugs of the invention.

Another embodiment of the invention involves a TAB form of the enzyme cytosine deaminase ("CD"). The deaminase enzyme catalyzes the conversion of 5-fluorocytosine ("5-FC"), a compound lacking in antineoplastic activity, to the potent antitumor drug, 5-fluorouracil ("5-FU").

In one embodiment, the prodrug is a peptide. Examples of peptides as prodrugs can be found in Trouet et al., *Proc Natl Acad Sci USA* 79:626 (1982), and Umemoto et al., *Int J Cancer* 43:677 (1989). These and other reports show that peptides are sufficiently stable in blood. Another advantage of peptide-derived prodrugs is their amino acid sequences can be chosen to confer suitable pharmacological properties like half-life, tissue distribution and low toxicity to the active drugs. Most reports of peptide-derived prodrugs relied on relatively nonspecific activation of the prodrug by, for instance, lysosomal enzymes.

The prodrug can be one that is converted to an active drug in more than one step. For example, the prodrug can be converted to a precursor of an active drug by the TAB. The precursor can be converted into the active drug by, example, the catalytic activity of one or more additional TABs, the catalytic activities of one or more other enzymes administered to the subject, the catalytic activity of one or more enzymes naturally present in the subject or at the target site in the subject (e.g., a protease, a phosphatase, a kinase or a polymerase), by a drug that is administered to the subject or by a chemical process that is not enzymatically catalyzed (e.g., oxidation, hydrolysis, isomerization or epimerization).

Most studies involving prodrugs are generated after programs with existing drugs are found to be problematic. In particular anticancer drugs were generally characterized by a very low therapeutic index. By converting these drugs into prodrugs with reduced toxicity and then selectively activating them in the diseased tissue, the therapeutic index of the drug can be significantly increased. See, e.g., Melton et al., Enzyme-prodrug strategies for cancer therapy (1999), and Niculescu-Duvaz et al., *Anticancer Drug Des* 14:517 (1999).

The literature describes many methods to alter the substrate specificity of enzymes by protein engineering or directed evolution. Thus one skilled in the art is able to evolve the specificity of an enzyme to accommodate even structures that would be poor substrates for naturally-occurring enzymes. Accordingly, prodrugs can be designed even though the drugs were otherwise not amenable to a prodrug strategy.

Another embodiment of the method of this invention provides a method of combination chemotherapy using several prodrugs and a single TAB. According to this embodiment, a number of prodrugs are used that are all substrates for the same TAB. Thus, a particular TAB converts a number of prodrugs into cytotoxic form, resulting in increased antitumor activity at the tumor site.

There is often a requirement for extending the blood circulation half-lives of pharmaceutical peptides, proteins, or small molecules. Typically short half-lives—lasting minutes to hours—require not only frequent, but also high doses for therapeutic effect—often so high that initial peak doses cause side effects. Extending the half-life of such therapeutics permits lower, less frequent, and therefore potentially safer doses, which are cheaper to produce. Previously, researchers have increased protein half-life by fusing them covalently to PEG, see U.S. Pat. No. 5,711,944, human blood serum albumin, see U.S. Pat. No. 5,766,883, or Fc fragments, see WO 00/24782. In addition, nonspecific targeting of drugs to human serum albumin has been accomplished by chemical coupling drugs in vivo. (See U.S. Pat. No. 5,843,440). Furthermore, in the case of cancer drugs it has been proposed that high molecular weight drugs may localize in tumors due to enhanced permeability and retention. Therefore, improvement in the therapeutic index of a drug can be obtained by linking the drug to a protein or other high molecular weight polymer.

In one embodiment, the subject in need thereof is a cancer patient. In another embodiment, the TAB is targeted to a TAG-72 expressing cell, tissue, tumor or organ. In another embodiment, the prodrug is converted by the TAB into an active drug. In another embodiment, the active drug is an alkylating agent. In another embodiment, the prodrug is an anticancer nitrogen mustard prodrug. In another embodiment, the active drug is melphalan. In another embodiment, the prodrug is C-Mel. In another embodiment, the prodrug is glutaryl-C-Mel or glutaryl-C-Mel-L-Phe-NH2 (see, for example, Senter et al, U.S. Pat. No. 5,773,435, which is incorporated by reference herein, including any drawings and Kerr et al, *Bioconjugate Chem* 9:255-59 (1998)). In another embodiment, the prodrug is vinca-cephalosporin or doxorubicin cephalosporin. See Bagshawe et al., *Current Opinion in Immunology*, 11:579-83 (1999). Other prodrug/enzyme combinations that can be used in the present invention include, but are not limited to, those found in U.S. Pat. No. 4,975,278 and Melton et al., Enzyme-Prodrug Strategies for Cancer Therapy Kluwer Academic/Plenum Publishers, New York (1999).

In a fourth aspect, the invention is drawn to a pharmaceutical composition comprising a TAB molecule. The TABs, nucleic acids encoding them and, in certain embodiments, prodrugs described herein can be incorporated into pharmaceutical compositions suitable for administration. Such compositions typically comprise the active compound and a pharmaceutically acceptable carrier. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a TAB, prodrug or nucleic acid of interest. Such methods comprise formulating a pharmaceutically acceptable carrier with an agent that modulates expression or activity of an active compound of interest. Such compositions can further include additional active agents. Thus, the invention further includes methods for preparing a pharmaceutical composition by formulating a pharmaceutically acceptable carrier with an agent that modulates expression or activity of a TAB, prodrug or nucleic acid of interest and one or more additional active compounds.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include normal saline, Water for Injection, 5% dextrose or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like) and suitable mixtures thereof. The proper fluidity can be maintained by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols such as mannitol, sorbitol, sodium chloride in the composition.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred method of preparation is freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches or capsules.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate or orange flavoring.

For administration by inhalation, the compounds are delivered in the form of an aerosol spray from a pressurized container or dispenser that contains a suitable propellant, e.g., a gas such as carbon dioxide or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts and fusidic acid derivatives. Transmucosal administration can be accomplished through the use of nasal sprays or suppositories. For transdermal administration, the active compounds are formulated into ointments, salves, gels or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In one embodiment, the formulation comprises sulfobutylether-7-beta-cyclodextrin and 2-hydroxypropyl-β-cyclodextrin, as disclosed, for example, in U.S. Pat. No. 6,216,375 and U.S. Pat. No. 6,537,988, each of which are incorporated by reference, herein, including any drawings.

Typically, the amount of TAB to be delivered to a subject will depend on a number of factors, including, for example, the route of administration, the activity of the TAB, the degree to which it is specifically targeted to the desired cells, tissues or organs of the subject, the length of time required to clear the non-specifically bound TAB from the subject, the desired therapeutic effect, the body mass of the subject, the age of the subject, the general health of the subject, the sex of the subject, the diet of the subject, the subject's immune response to the TAB, other medications or treatments being administered to the subject, the severity of the disease and the previous or future anticipated course of treatment.

For applications in which a prodrug also is administered, other factors affecting the determination of a therapeutically effective dose will include, for example, the amount of prodrug administered, the interval between administration of the TAB and the prodrug, the activity of the prodrug and its corresponding active drug and the side effects or toxicities of the prodrug and the active drug.

Examples of ranges of mass of TAB/mass of subject include, for example, from about 0.001 to 30 mg/kg body weight, from about 0.01 to 25 mg/kg body weight, from about 0.1 to 20 mg/kg body weight, and from about 1 to 10 mg/kg, 2 to 9 mg/kg, 3 to 8 mg/kg, 4 to 7 mg/kg, or 5 to 6 mg/kg body weight.

In a particular example, a subject is treated with a TAB in the range of between about 0.1 to 20 mg/kg body weight, one time per week for between about 1 to 10 weeks, preferably between 2 to 8 weeks, preferably between about 3 to 7 weeks and preferably for about 4, 5 or 6 weeks. It will also be appreciated that the effective dosage of TAB may increase or decrease over the course of a particular treatment, and that the treatment will continue, with or without modification, until a desired result is achieved or until the treatment is discontinued for another reason. Changes in dosage may result and become apparent from the results of diagnostic assays as described herein.

It is understood that appropriate doses of prodrugs depend upon a number of factors within the ken of the ordinarily skilled physician, veterinarian or researcher. The dose(s) of the prodrug will depend, for example, on the same factors provided above as factors affecting the effective dose of the TAB. Exemplary doses include milligram or microgram amounts of the prodrug per kilogram of subject or sample weight (e.g., about 1 microgram per kilogram to about 500 milligrams per kilogram, about 100 micrograms per kilogram to about 5 milligrams per kilogram or about 1 microgram per kilogram to about 50 micrograms per kilogram). It is furthermore understood that appropriate doses of a prodrug depend upon the potency of the prodrug with respect to the desired therapeutic effect. When one or more of these prodrugs is to be administered to an animal (e.g., a human), a physician, veterinarian or researcher may, for example, prescribe a relatively low dose at first, subsequently increasing the dose until an appropriate response is obtained.

Preferably, the TAB is administered to the subject, then the prodrug is administered. More preferably, the time between the administration of the TAB and administration of the prodrug is sufficient to allow the TAB to accumulate at its target site by binding to its target, and to allow unbound TAB to be cleared from the non-targeted portions of the subject's body. Most preferably, the ratio of target-bound TAB to unbound TAB in the subject's body will be at or near its maximum when the prodrug is administered. The time necessary after administration of the TAB to reach this point is called the clearing time. The clearing time can be determined or approximated in an experimental system by, for example, administering a detectable TAB (e.g., a radiolabeled or fluorescently labeled TAB) to a subject and simultaneously measuring the amount of enzyme at the target site and at a non-targeted control site at timed intervals. For some prodrugs, particularly those whose counterpart active drugs are highly toxic, it may be more important to ensure that the levels of unbound TAB in the subject's system are below a certain threshold. This too can be determined experimentally, as described above. Dosing intervals of between about 72 and about 96 hours are preferred.

In one embodiment, administration of the prodrug is systemic. In another embodiment, administration of the prodrug is at or near the target.

The pharmaceutical compositions can be included in a container, pack, dispenser or kit together with instructions for administration.

EXAMPLES

Example 1

Construction of Plasmid pNA22.7 Expressing TAB2.1 Protein

The amino acid sequence of the scFv portion of TAB2.1 molecule was derived from murine anti-TAG-72 monoclonal antibody (mAb) CC49 sequence (Abergel et. al. (1993) Proteins: Structure, Function and Genetics 17:438-443). The nucleotide sequence of the synthetic gene was designed based on E. coli codon usage plus a 15-aa peptide linker connecting the vH and vL domains with the following genetic configuration: vH-(GGGGS)$_3$-VI (SEC) ID NO: 24). A 973-bp DNA fragment containing the designed gene was synthesized by McLab (South San Francisco, Calif.) with flanking BglI and EcoRV restriction enzyme sites and cloned into plasmid pPCRII-TOPO (Invitrogen Corp., Carlsbad, Calif.) resulting in plasmid pAG.

Plasmid pME25.1 was used to clone the synthetic scFv portion of CC49 antibody from plasmid pAG. Upon digestion of plasmids pAG and pME25.1 with BglI and EcoRV enzymes, a 0.88-kb insert fragment and a 4.3-kb vector fragment, respectively, were gel purified. They were then ligated, followed by transformation into E. coli TOP10 (Invitrogen, Carlsbad, Calif.) chemically competent cells and selection on LA+Cm5+0.1 CTX plates. Plasmid DNAs isolated from 10 transformants were checked for proper size and orientation of the CC49 scFv fragment by digestion with PvuII enzyme. Expected restriction patterns were observed for all 10 clones tested. After testing several of them for expression and binding, plasmid pNA22.7 was selected for further engineering and named TAB2.1.

Example 2

Construction of Plasmid pSW239.1 Expressing TAB2.4 Protein

Plasmid pSW239.1 (TAB2.4) was constructed using plasmid pNA22.7 (TAB2.1) as a PCR template by a modification of the regular Quikchange Mutagenesis protocol (Stratagene, CA) as described before (Wang, W. & Malcolm, B. A. BioTechniques 26:680-682 (1999)). This manipulation increases the linker size between vH and vL domains from 15-aa [(GGGGS)$_3$] (SEQ ID NO: 24) to 30-aa [(GGGGS)$_6$] (SEQ ID NO: 23) in the TAB2.4 protein. Using primers HR061F and HR061R (HR061F: 5'-ACCGTTAGCAGCGGTGGTG- GCGGTTCGGGTGGCGGAGGCAGCGGTG- GAGGGGGCTCTG GGGGCGGCGGTTCCGGTGGAG- GTGGAAGTGGC-3' (SEQ ID NO: 25) and HR061R: 5'-ACCGCCGCCCCCAGAGCCCCCTCCAC- CGCTGCCTCCGCCACCCGAACCGCCACCACCGC TGCTAACGGTCACGCTGGTCCCTTGACC-3' (SEQ ID NO: 26)) for inserting 15-aa (GGGGS)$_3$ (SEQ ID NO: 24) sequence whose nucleotide sequence is shown in capitals. A two-step regular Quikchange mutagenesis (Stratagene, CA) PCR reaction was performed followed by digestion with DpnI enzyme. Two μL out of 50 μL PCR product was transformed into E. coli TOP10F' chemically competent cells followed by selection of transformants on LA+Cm10+0.1 CTX plates. Plasmid DNAs from 16 clones were amplified by Templiphi-100 amplification kit (Amersham Biosciences) and sequenced to confirm the insertion of extra sequences. Eleven out of 16 clones were found to have the desired insertion. Complete sequencing of the entire fusion gene of plasmid pSW239.1 revealed no additional mutations elsewhere in the gene. Finally, plasmid pSW239.1 was selected as TAB2.4 molecule, sequence ID NO: (TAB2.4), as shown in FIG. 1A. The amino acid sequence of TAB2.4 is shown in FIG. 1.

Example 3

Combinatorial Consensus Mutagenesis of TAB2.4

To improve the expression of the TAB2.4 protein, a combinatorial consensus mutagenesis approach as described in WO US04/30085, incorporated by reference, herein, including any drawings and was pursued by targeting 12 amino acid residues in the frame work regions of vH and vL domains using plasmid pSW239.4 as a template. These 12 residues (8 positions in vH and 4 positions in vL) were identified as being significantly different (<10% abundance) compared to a typical human antibody sequence. 21 mutations were made among these 12 sites, some having more than one substitution. Using a modified version of Multi-site Quikchange Mutagenesis (Stratagene, CA) protocol as described before in WO US04/30085, incorporated by reference, herein, including any drawings, CCM libraries ME367 and ME368 with combined primer concentrations of 0.4 μM and 2 μM, respectively, were constructed employing 21 phosphorylated primers as shown in Table 1.

TABLE 1

Sequence of primers used for combinatorial consensus mutagenesis (CCM) of TAB2.4 protein. Primer name corresponds to the amino acid to be changed in the light (L) or heavy (H) chain, its position, and the intended mutation (mutated codon shown in upper case). So, HD8G corresponds to Asp (D) at position 8 of the heavy (H) chain to be changed to Gly (G). The numbering is based on the Kabat system of either light or heavy chains. All primers were designed to the sense strand.

| Oligo's: Name | Sequence (5' > 3') | Length(bp) | SEQ ID NO |
|---|---|---|---|
| Combinatorial consensus mutagenesis primers | | | |
| vH | | | |
| HD8G | [Phos]GTTACAGCAGTCAGGCGCGGAGTTGGTGAAACCGGC | 37 | 27 |
| HH32M | [Phos]CACCTTTACCGACATGGCCATTCACTGGGTAAACAG | 37 | 28 |

TABLE 1-continued

Sequence of primers used for combinatorial consensus mutagenesis (CCM) of TAB2.4 protein. Primer name corresponds to the amino acid to be changed in the light (L) or heavy (H) chain, its position, and the intended mutation (mutated codon shown in upper case). So, HD8G corresponds to Asp (D) at position 8 of the heavy (H) chain to be changed to Gly (G). The numbering is based on the Kabat system of either light or heavy chains. All primers were designed to the sense strand.

| Oligo's: Name | Sequence (5' > 3') | Length(bp) | SEQ ID NO |
|---|---|---|---|
| HH32I | [Phos]CACCTTTACCGACATTGCCATTCACTGGGTAAAACAG | 37 | 29 |
| HA33G | [Phos]CTTTACCGACCATGGCATTCACTGGGTAAAACAGAAC | 37 | 30 |
| HA33W | [Phos]CTTTACCGACCATTGGATTCACTGGGTAAAACAGAAC | 37 | 31 |
| HA33Y | [Phos]CTTTACCGACCATTATATTCACTGGGTAAAACAGAAC | 37 | 32 |
| HN4R | [Phos]CTGGGTAAAACAGCGCCCGGAACAGGGCCTGGAGTGG | 37 | 33 |
| HN40A | [Phos]CTGGGTAAAACAGGCGCCGGAACAGGGCCTGGAGTGG | 37 | 118 |
| HN40P | [Phos]CTGGGTAAAACAGCCGCCGGAACAGGGCCTGGAGTGG | 37 | 119 |
| HF51I | [Phos]GATTGGGTATATTAGCCCGGGTAATGATGACTTTAAG | 37 | 34 |
| HF57T | [Phos]GTAATGATGACACCAAGTATAACGAACGCTTTAAAG | 36 | 35 |
| HR62K | [Phos]GTATAACGAAAAATTTAAAGGTAAAGCCACCCTGAC | 36 | 36 |
| HR62S | [Phos]GTATAACGAAAGCTTTAAAGGTAAAGCCACCCTGAC | 36 | 37 |
| HV80L | [Phos]GTCCACTGCTTACCTGCAGCTGAACAGTCTCACGTCAG | 38 | 38 |
| HV80M | [Phos]GTCCACTGCTTACATGCAGCTGAACAGTCTCACGTCAG | 38 | 39 |
| vL LS5T | [Phos]GATATTGTCATGACCCAATCTCCGTCATCACTGCCC | 36 | 40 |
| LA53N | [Phos]CTATTGGGCCTCTAACCGTGAATCCGGTGTTCCAGATC | 38 | 41 |
| LA53T | [Phos]CTATTGGGCCTCTACCCGTGAATCCGGTGTTCCAGATC | 38 | 42 |
| LK79E | [Phos]CATTTCGTCTGTGGAAACAGAAGACCTGGCTGTCTAC | 37 | 43 |
| LK79Q | [Phos]CATTTCGTCTGTGCAGACAGAAGACCTGGCTGTCTAC | 37 | 44 |
| LV105E | [Phos]GTACTAAATTAGAACTCAAAACACCGGTGTCAGAAAAAC | 39 | 45 |

After mutagenesis and DpnI digestion, 1.5 µL out of 25 µL PCR reaction mix was transformed into *E. coli* TOP10F' cells followed by selection on LA+Cm20+0.1 CTX plates. 96 clones from each library were initially screened for improved expression in 96-well microtiter plates as described below. Statistical analysis of the sequence to activity data revealed that 5 of the 21 mutations included in the library design were detrimental for binding. Thus, new libraries were designed without the primers coding for those mutations (light chain H32M, H32I, A33G, A33W and A33Y). These new libraries were named ME374, ME375, and ME377. ME374 contained all 16 mutations at 0.4 µM primer concentration, ME375 had all 16 at 0.1 µM primer concentration, and ME377 had mutations D8G, N40A, N40P, V80L in the heavy chain and A53T in the light chain.

Example 4

Screening of CCM Libraries

Libraries pME367 and pME368 were plated onto agar plates containing LB medium and 5 mg/L chloramphenicol (CMP) and 0.1 mg/L cephotaxime (CTX, Sigma). Colonies from each library (96 clones each including parent) were transferred into 96-well plates containing 100 µL LB+5 mg/L CMP. Plates were incubated at 37° C. in a humidified box with shaking for 24 h as a preculture. Plates were replicated into 100 µL of LB+5 mg/L CMP and grown for 48 h at 37° C. On the day of screening, 100 µL of B-Per reagent (PIERCE) was added into each well and shaken at room temperature for 30 min.

Figure 2A:
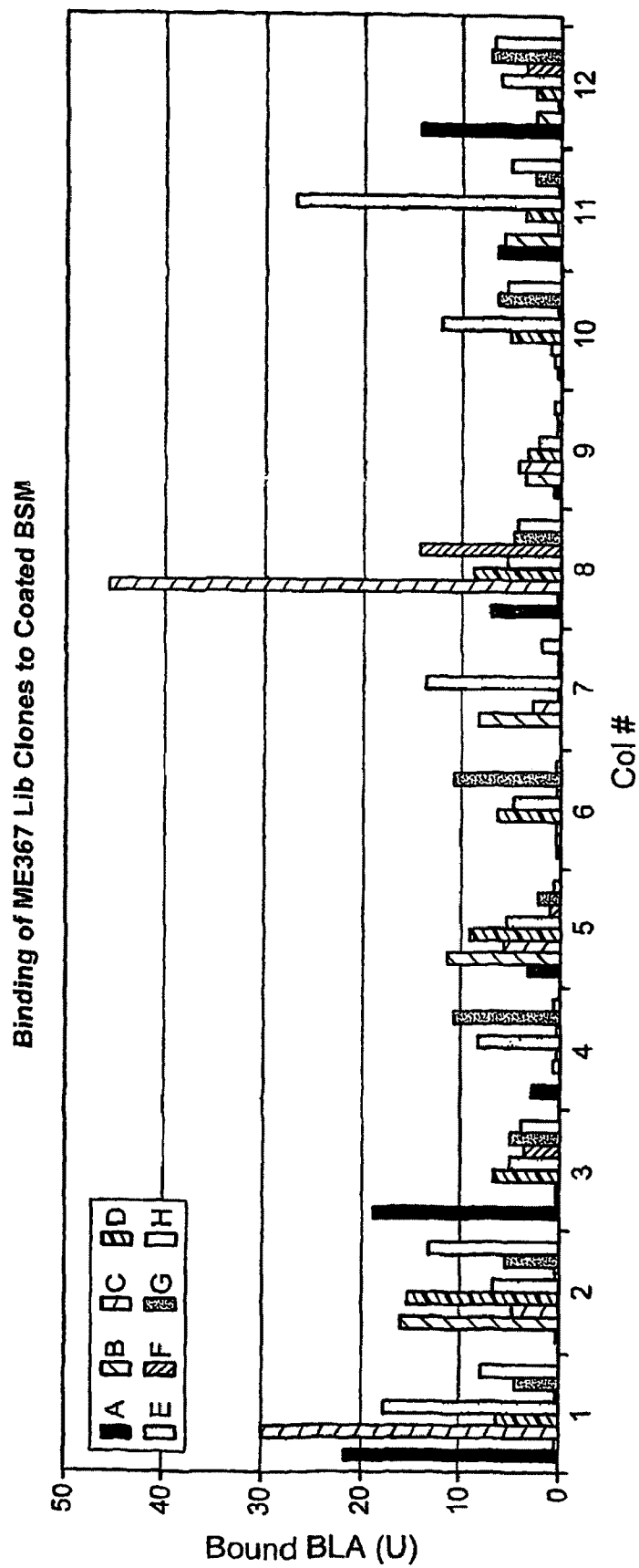
FIG. 2 shows the screening data for binding to coated BSM, the data showing clones from 36 libraries ME367 (top) and ME368 (bottom), as set forth in Example 4. The x-axis shows the colony number, and the y-axis shows bound BLA.
Figure 2B:
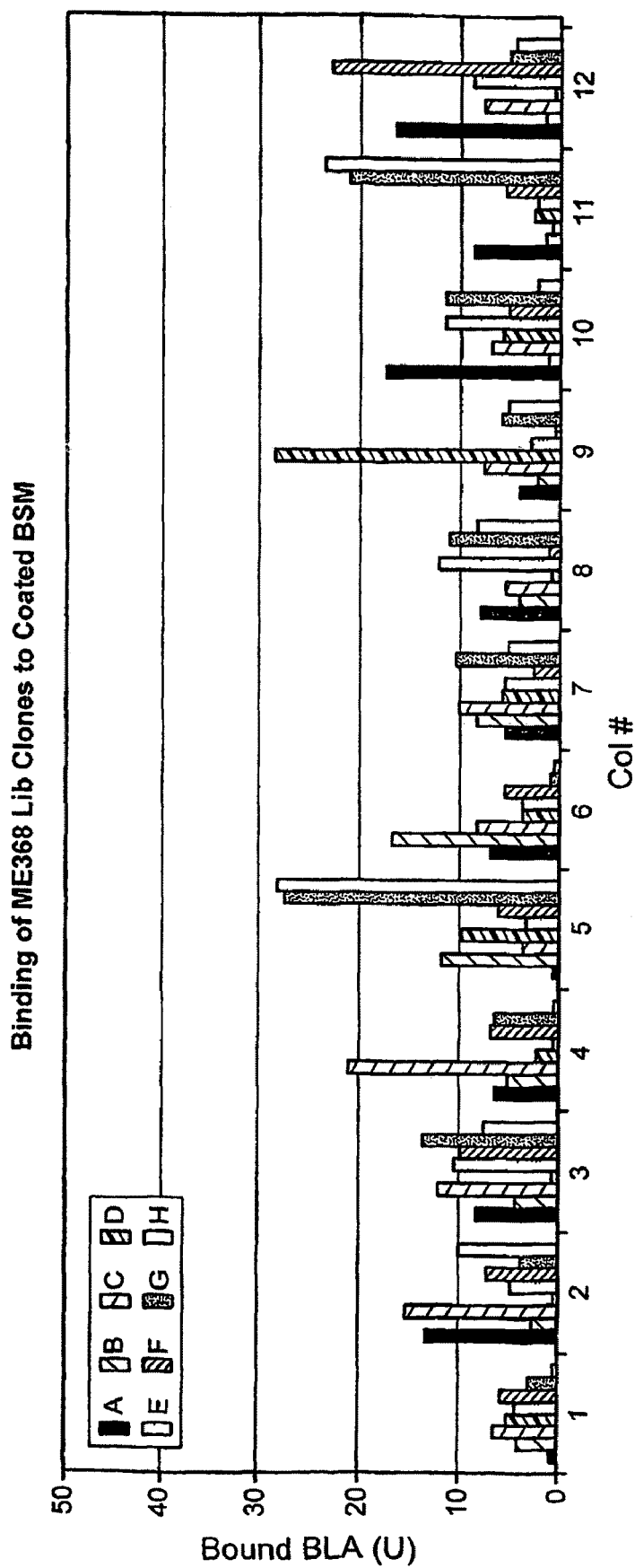
Figure 3:
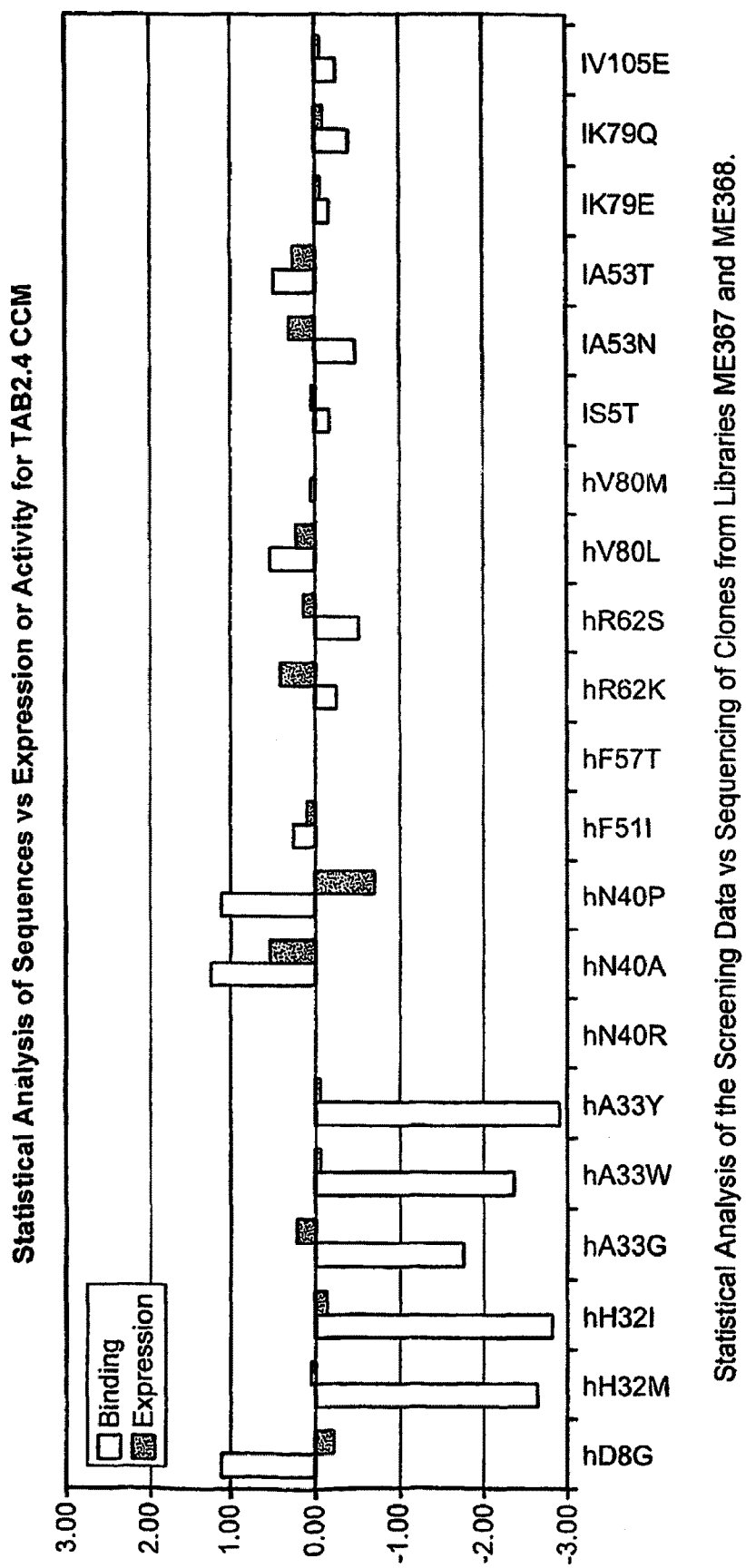
FIG. 3 sets forth the statistical analysis of the screening data versus sequencing of clones from libraries ME367 and ME368, as set forth in Example 4.

Target Bovine Submaxillary Mucin ("BSM", Sigma) is a mucin containing the TAG-72 epitope shown previously to react with B72.3 and CC49 (O'Boyle, K P. et al. (1996). Hybridoma 15, 401-408). BSM was coated in high binding capacity 96-well polystyrene plate (Costar #9018) by adding 100 µL of 10 µg/mL BSM in PBS and the plate was incubated at 4° C. overnight. The plates were then washed with PBST (PBS+0.1% Tween 20) and blocked with 200 µl well of PBST for 2 h at room temp. The plates were then washed three times with PBST. 7 µL of B Per extract library sample was added to 93 µL/well of PBST. The plate was incubated at room temperature with gentle shaking for 2 h. The plates were then washed three times with PBST. 200 µL of BLA substrate nitrocefin in PBSO (PBS+0.125% Octylglucopyranoside) was added into each well, and the bound BLA activity was measured by monitoring hydrolysis of nitrocefin at wavelength 490 nm at room temperature (t=0) (see FIG. 2 and for nitrocefin assay, see, WO 03/105757, incorporated by reference herein, including any drawings). Statistical analysis of the sequence to activity data revealed that 5 of the 21 mutations included in the library design were detrimental for BSM binding (see e.g., FIG. 3). For each mutation in the library, the statistical analysis results in a parameter determined from the experimental data. If a mutation improves either expression or binding or another measurable variable, the parameter will be positive in value or negative in value if the mutation is detrimental. The parameter is based on a logarithmic value such that a parameter of 1 means that the mutation provides a ~10-fold improvement. The parameter has to be analysed with regards to the number of times that mutation was observed in the library. The more a mutation was observed, the more credible the parameter value becomes. Thus, new libraries were designed without primers coding for those mutations (light chain H32M, H32I, A33G, A33W and A33Y). One plate each of libraries ME374, ME375 and ME377 were screened as previously described except that LB+10 mg/L CMP was used as the growth media. Also, total BLA activity (expression) was measured a 1/10 dilution of the B-per extract in PBSO by adding 20 µL sample dilution to 180 µL PBSO and by monitoring hydrolysis of nitrocefin at wavelength 490 nm at room temperature.

Figure 4:
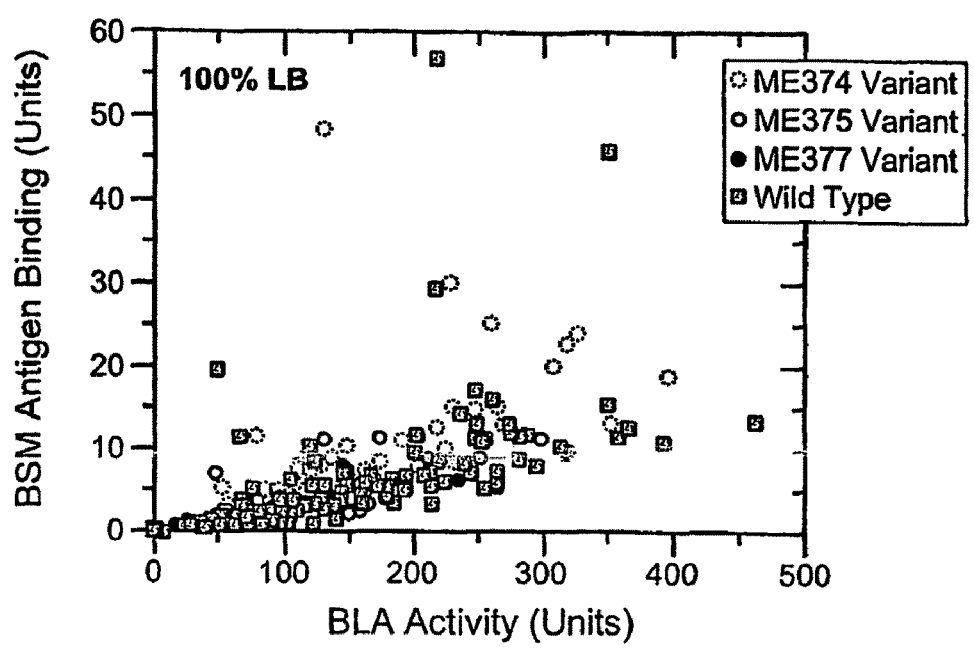
FIG. 4 shows the screening data for binding to coated BSM as opposed to BLA activity of clones from libraries ME374, ME375 and ME377, as set forth in Example 4. Many clones in the libraries are wild type TAB2.4 and are shown by squares. The x-axis shows input BLA activity, and the y-axis shows BSM antigen-binding units. Clones located to the right express more BLA activity and clones higher than the average diagonal trend bind better to coated BSM so that the output/input ratio of BLA activity is higher then average. The inset shows clone codes used.

Finally, a comparison of binding was determined as follows. After BSM bound BLA activity was measured at t=0, the plates were incubated 1 h at room temperature with gentle shaking. The plates were then washed three times with PBST. The remaining bound BLA activity (t=1) was measured. The ratio of the bound activity after an hour incubation t=1 over the bound BLA activity at t=0 provides a comparison of off-rates. FIG. 4 shows the screening data for libraries ME374, MB375 and ME377 where many variants show a bound/input ratio higher than the average of TAB2.4 clones.

Figure 5:
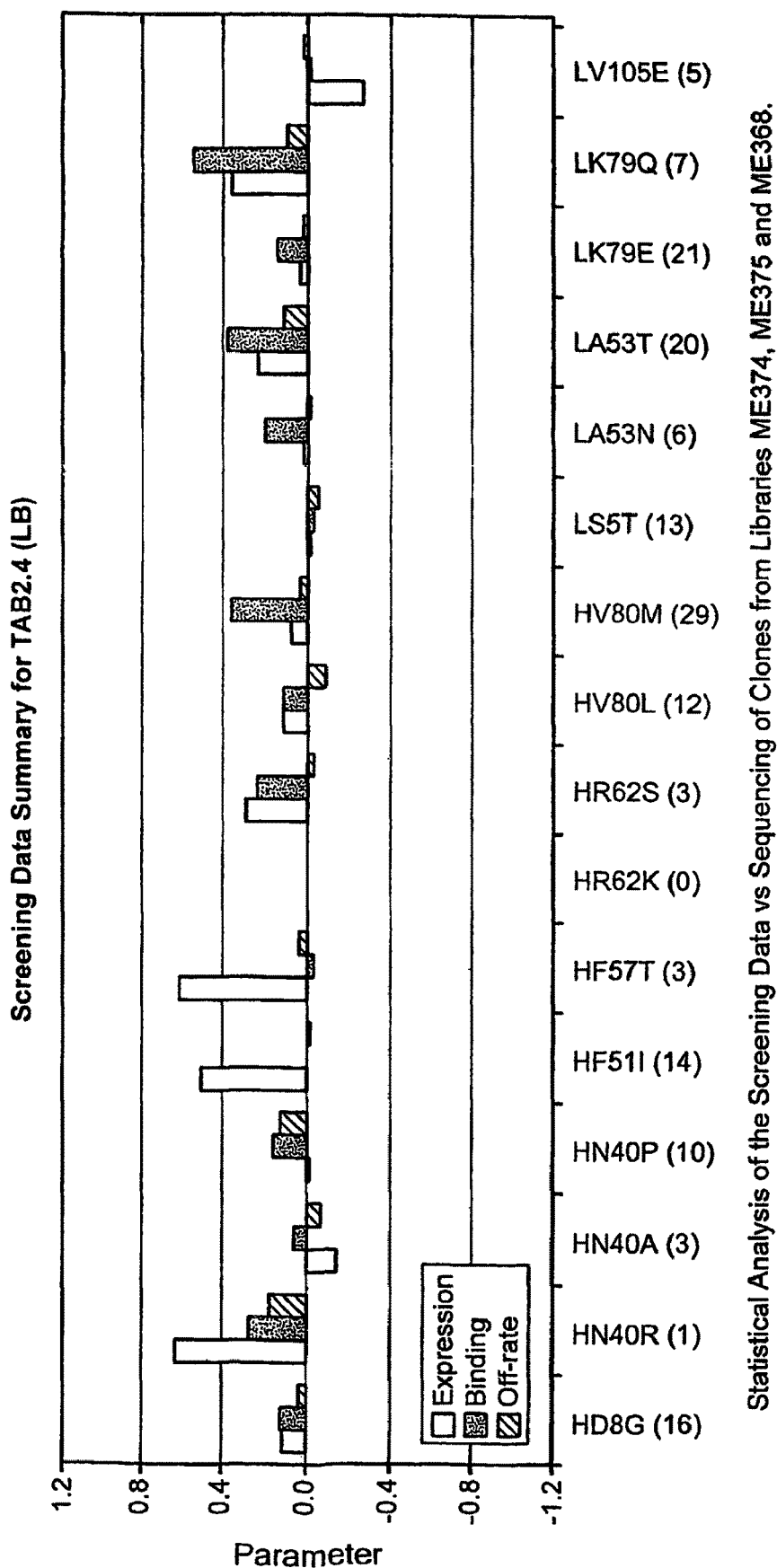
FIG. 5 shows the statistical analysis of screening data as opposed to sequencing of clones from libraries ME374, ME375 and ME368, as set forth in Example 4. The x-axis shows the clone number, and the y-axis shows the parameter [for the statistical algorithm, please see, Amin, N., A. D. Liu, S. Ramer, W. Aehle, D. Meijer, M. Metin, S. Wong, P. Gualfetti and V. Schellenberger (2004) Protein Eng Des Sel 17, 787-93, Construction of stabilized proteins by combinatorial consensus mutagenesis].

In FIG. 5, statistical analysis of the sequence to screening data shows that a few mutations seem beneficial for increased expression of TAB2.4.

From the screen, 22 clones were picked for further analysis. Glycerol stocks of the clones, plus parent TAB2.4 and a control CAB1.2, which binds carcinoembryonic antigen ("CEA"), but does not bind TAG-72, were streaked out on LA+5 mg/L CMP agar plate. Four colonies from each variant were inoculated in 100 µL of LB+10 mg/L CMP in a 96-well plate and grown overnight at 37° C. The plate was replicated into three 96-well plates containing 100 µL of LB+10 mg/L CMP and grown 48 h at 37° C. B-per extracts of the three plates (triplicate) were prepared as previously described. BLA activity, binding to BSM and off-rate were also measured as previously described. Samples were diluted 10-fold in PBS for the measurement of BSM binding.

Figure 6:
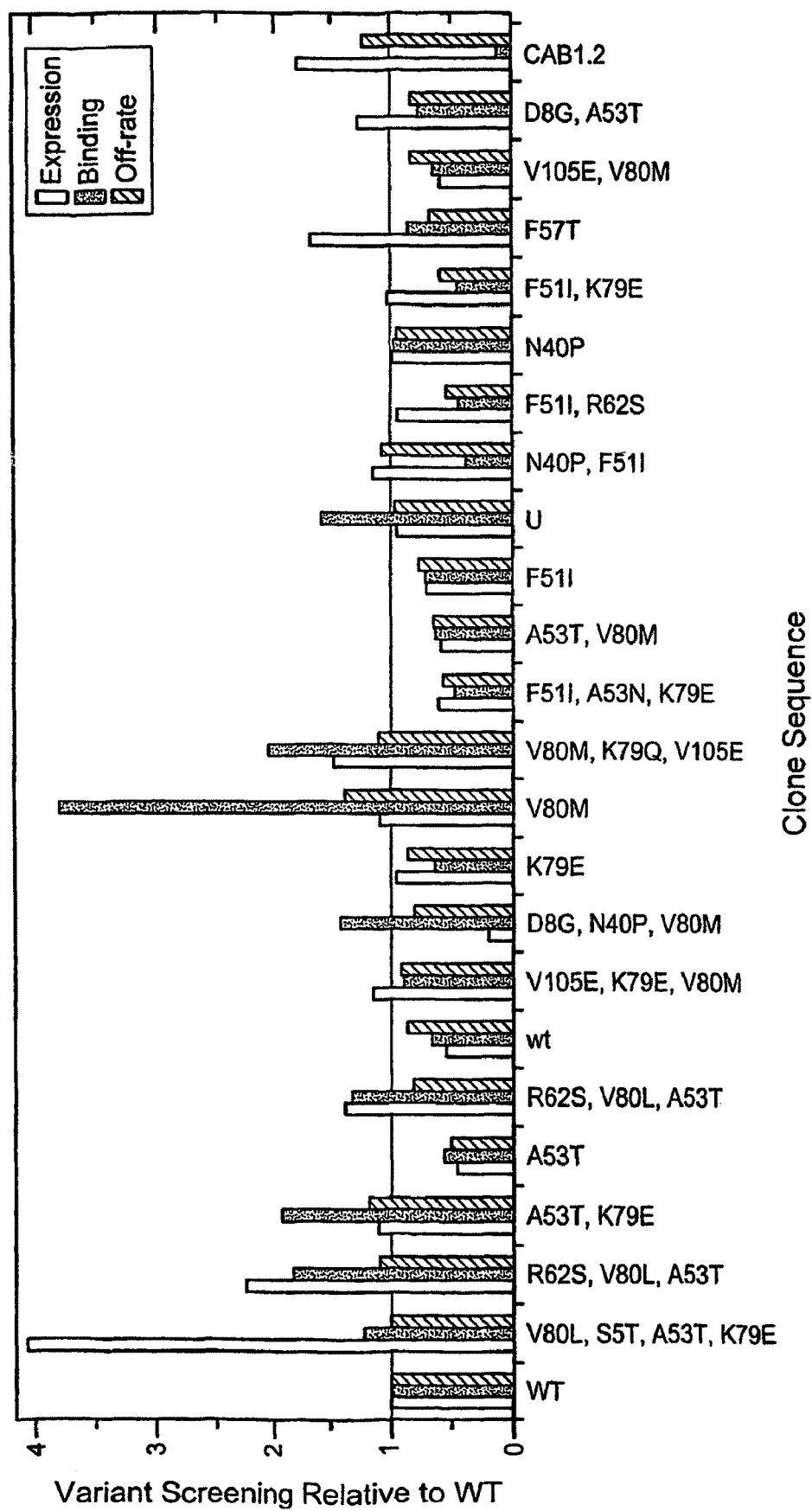
FIG. 6 shows screening of 22 clones from TAB2.4 consensus combinatorial mutagenesis, as set forth in Example 4. The data show the ratio of the value for the clone over TAB2.4, wild-type for expression, BSM binding or off-rate. A value>1 means that the clone has better expression, BSM binding than parent TAB2.4, while a value<1 means that the clone has a lower expression, BSM binding or off-rate. The x-axis shows clone number, and the y-axis shows variant screening relative to wild-type.

Data in FIG. 6 show that a few clones have better expression and binding to BSM. However, careful analysis of the sequences revealed that some clones had mutations in the linker region between the vL and the vH which could affect the amount of dimer and multimer present in the B-per extract and thus affect the binding data. The clones having linker mutations were not further analyzed.

The seven best expressing/binding clones from the data and sequence analysis, and a TAB2.4 control, were grown in a tube containing 2 mL LB+10 mg/L CMP overnight at 37° C. Then, 200 µL of the culture was transferred to 25 mL TB media+10 mg/L CMP in triplicate and grown 48 h at 37° C. One mL of the culture was pelleted and one ML of B-per reagent was added and incubated 60 min with shaking. The B-per extract was spun and the supernatant was transferred to a new tube. Each sample was tested for BLA activity, BSM binding (serial dilution) and off-rate as described previously. The samples were compared in an anti-BLA western blot for intactness of the fusion protein. For the western blot, each of the samples were prediluted so that only 50 ng fusion protein in each well was loaded. The 50 ng was diluted 2/3 into reducing agent by mixing 60 µL of each sample with 30 µL 4×LDS Sample Buffer and Sample Reducing Agent (Invitrogen). The gel loading samples were heated for 5 min at 85° C. 15 µL of each sample was loaded for the gel that was to be stained into separate wells of NuPAGE 4-12% Bis-Tris gels.

Protein was then transferred from the SDS-PAGE gel onto a PVDF membrane using transfer buffer (Invitrogen) and run at 25V constant voltage for 60 min. Membrane was blocked by immersing it in a 2.5% BSA solution (Blocker BSA in Tris Buffered Saline with 0.1% tween-20 (TBST) and shaking for 60 min. Membrane was immersed into the primary antibody solution and shaken for 60 min (Abgent mouse anti-BLA mAb was diluted 1:10,000 in TBST). Membrane was rinsed 3×5 min in TBST. Membrane was immersed into the secondary antibody solution (goat anti-mouse IgG:HRP (Pierce) diluted 1:20,000 in TBST) and shaken for 60 min. Membrane was rinsed 3×10 min in TBS-T.

2 mL ECL Plus (Amersham Biosciences) detection solution was made by adding 50 µL of solution B to 2 mL of solution A. The detection solution was pipetted over the membrane surface. After 5 min incubation with the detection solution, excess reagent was drained off and the membrane was placed protein-side down on Storm Imager scanning bed. A scan was done using the blue fluorescence/chemifluorescence mode. Densitometry was used to determine the percentage of intact protein. The western membrane was scanned using Storm Imager using the image Quant program to do densitometry on the bands for both intact and degraded material. Cross-section lines were used to report band intensity as area under the curve (AUC) and values were calculated in terms of percent intact, percent degraded as BLA and total magnitude of band intensity (AUC).

Figure 7:
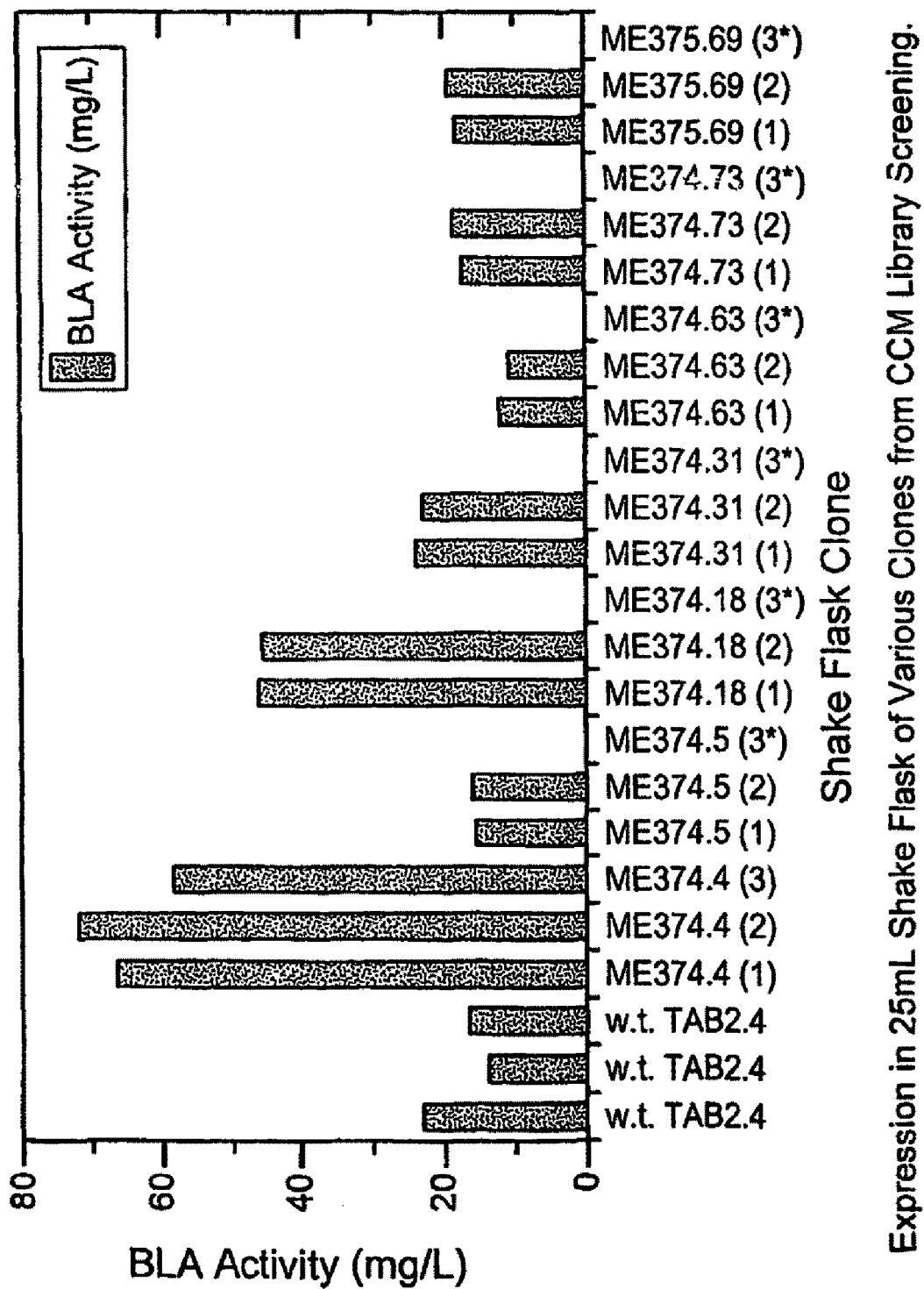
FIG. 7 shows expression in a 25 mL shake flask of various clones from the combinatorial consensus mutagenesis library screening, as set forth the clone number, and the y-axis shows BLA activity.
Figure 8:
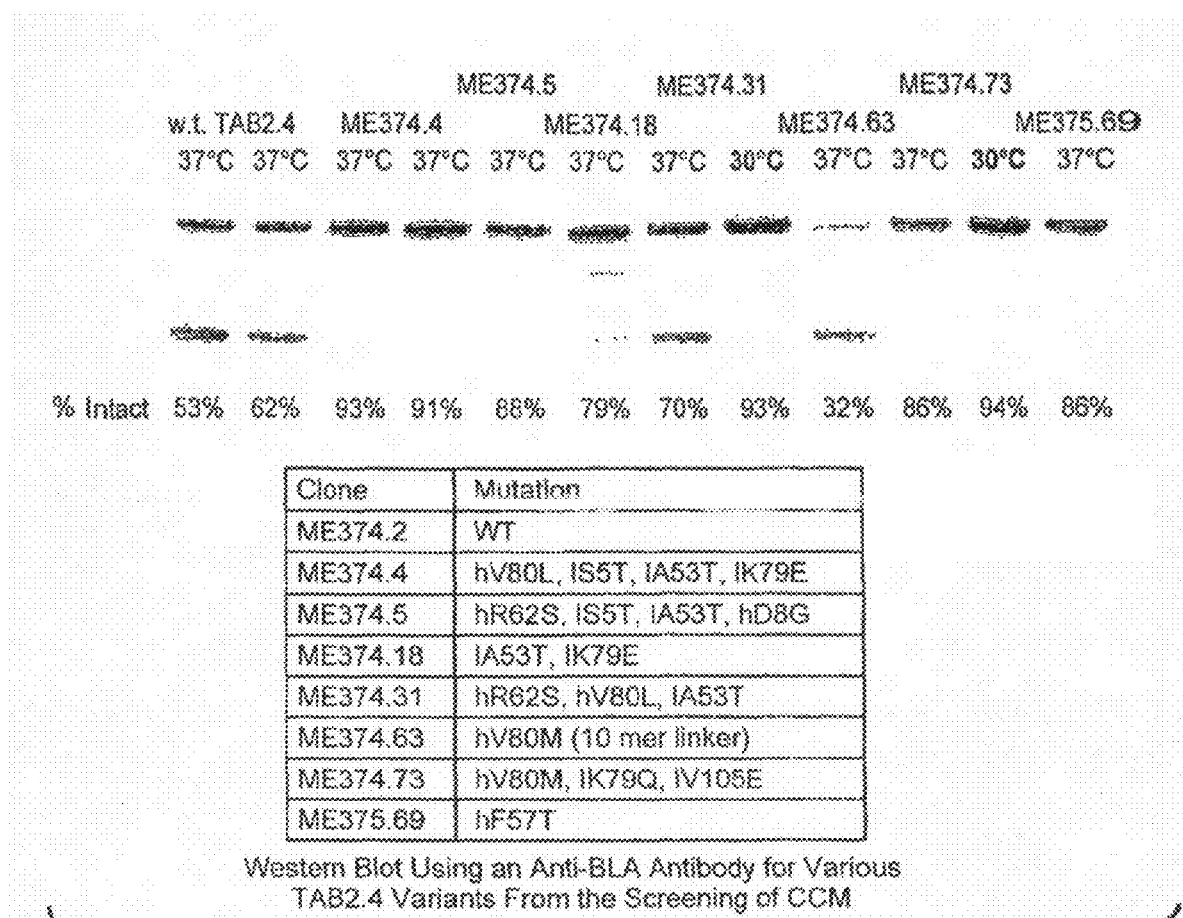
FIG. 8 shows a Western blot using an anti-BLA antibody for various TAB2.4 variants from the screening of the combinatorial consensus mutagenesis library, as set forth in Example 4. The top panel shows the Western, the bottom panel contains a chart setting forth mutations present in each of the clones.
Figure 10:
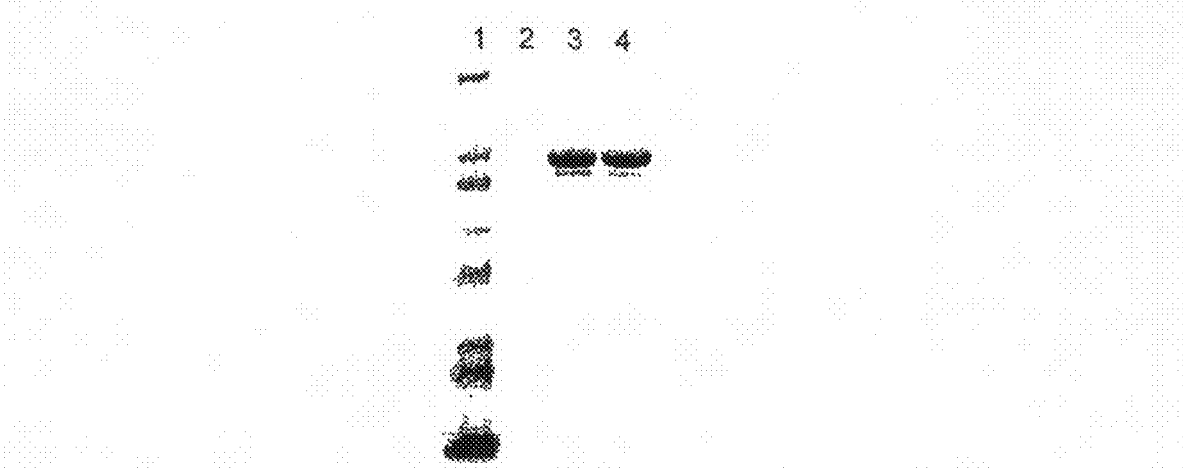
Figure 9:
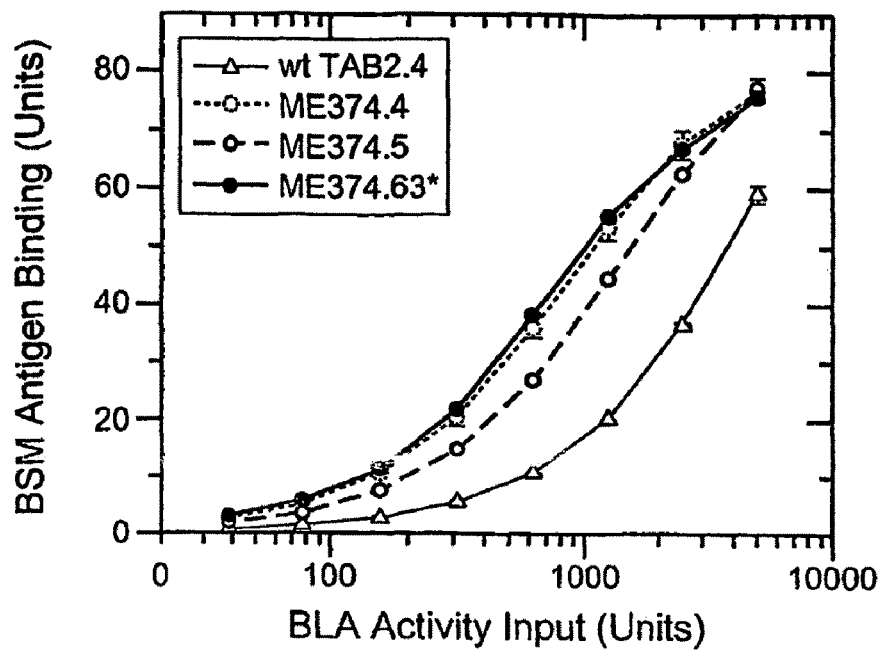
Figure 11:
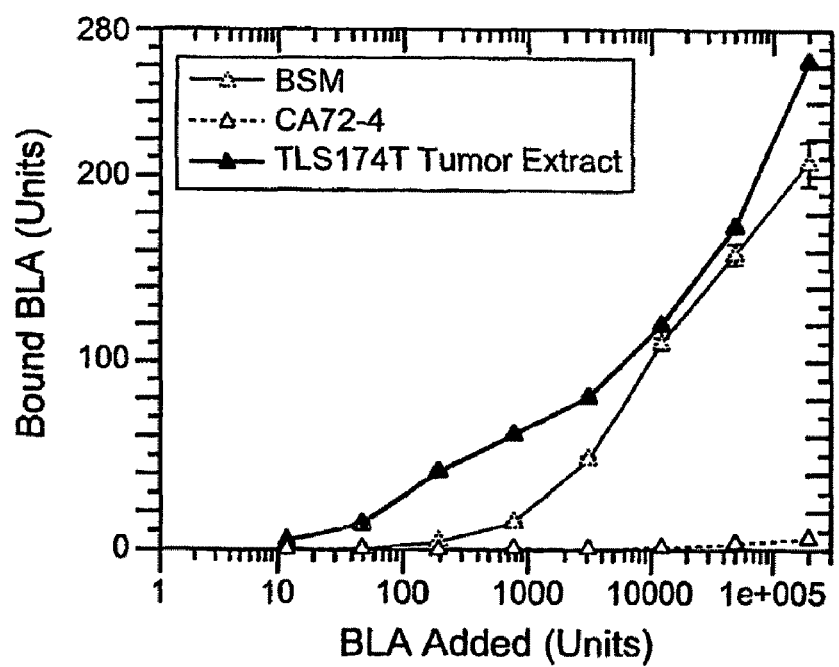
Figure 12:
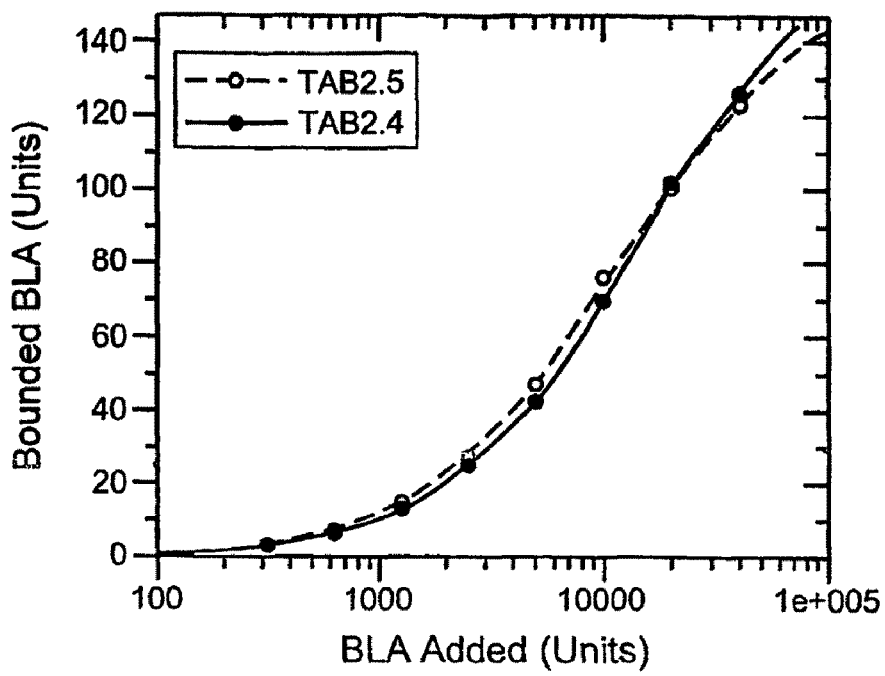
Figure 13:
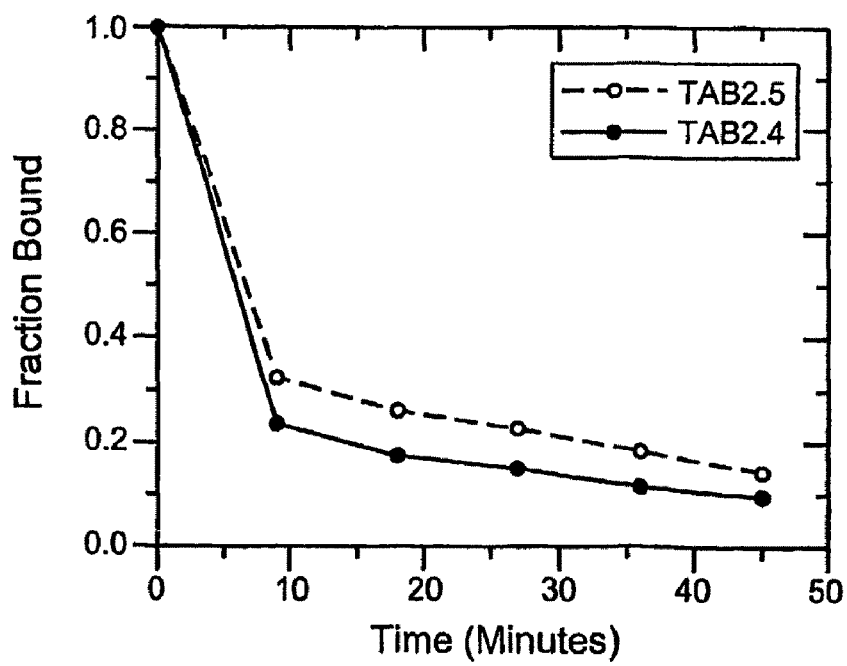
Figure 14:
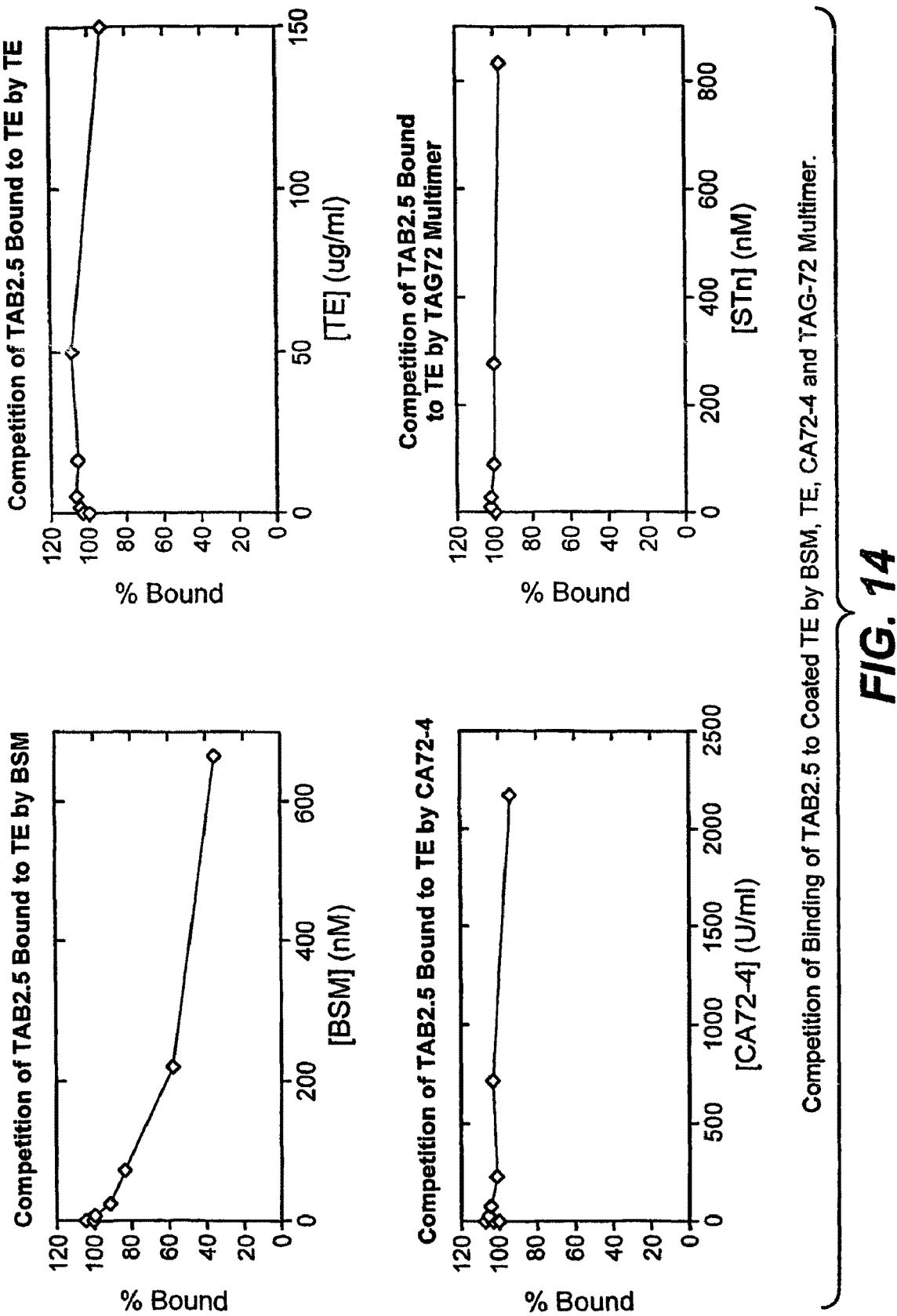
Figure 15:
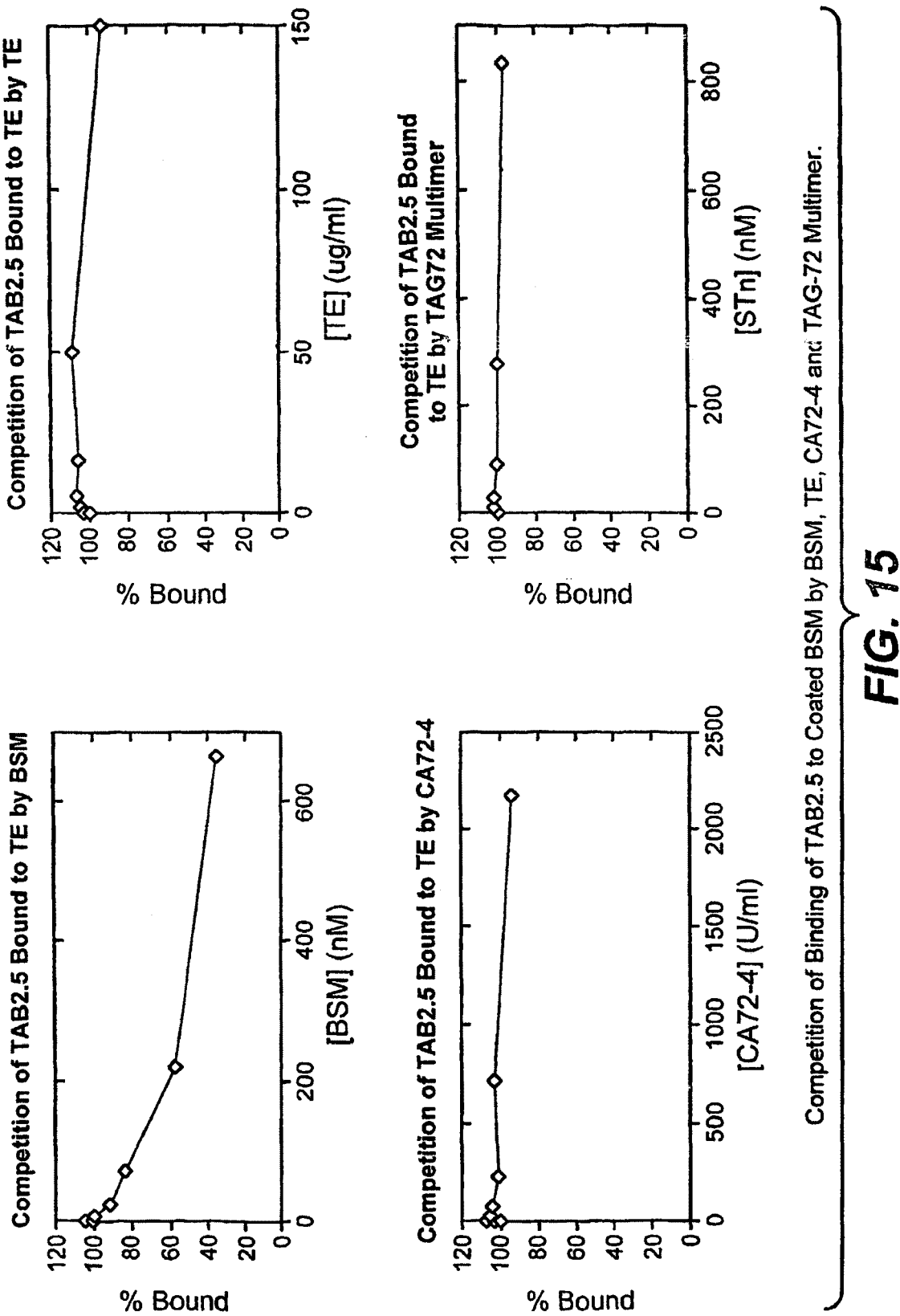

Clone pME374.4 showed better expression (3.5-4-fold better, see FIG. 7) and intactness (~90% vs ~50%, see FIG. 8) than the parent TAB2.4 and equivalent binding and off-rate to coated BSM and was picked as the next generation and named TAB2.5. TAB2.5 contains mutations V80L in the vH region of the scFv fragment, and S5T, A53T and K79E in the vL region compared to TAB2.4. A binding curve to coated BSM showed that the clones tested had higher apparent affinities than TAB2.4 (see FIG. 9).

Example 5

Expression and Purification of TAB2.4 and TAB2.5

The cell was disrupted with B-PER as follows. 2.5 mL B-PER Reagent (in Phosphate Buffer, Pierce Biotechnology Inc., product #78266) per gram of frozen *E. coli* cell paste was added. Benzonase Nuclease (Novagen, product #70664-3) was also added at a dilution of 1:1000 to hydrolyze DNA. Mixture was stirred vigorously for 60 min at room temperature. Cell debris was removed by centrifugation at 4° C. for 20 min and 12,000 rpm. Pellet was discarded.

Fusion protein was captured via PBA affinity chromatography. A 5 mL PBA column (m-Aminophenylboronic acid immobilized onto agarose beads from Sigma, product # A-8312) was equilibrated with 25 mL TEA buffer (20 mM triethanolamine, pH 7) prior to loading crude protein. After sample loading, the column was washed first with 25 mL TEA buffer, and a second time with 25 mL TEA/NaCl buffer (20 mM triethanolamine; 0.5 M NaCl, pH 7). β-lactamase fusion protein was eluted with 25 mL borate/NaCl buffer (0.5 M borate/0.5 M NaCl, pH 7) and collected in 5 mL fractions. Eluted fractions were assayed for β-lactamase activity using the nitrocefin plate assay, as described above.

Size exclusion chromatography was used to obtain pure monomer. 5 mL of concentrated TAB protein was loaded onto a Superdex 75 preparative grade column (Amersham Biosciences, product #17-1070-01) equilibrated with PBS. Proteins were separated with a flow rate of 2 mL/min of PBS and collected in 5 mL fractions.

Endotoxin was removed via Detoxi-Gel™. 1-4 mL of concentrated β-lactamase fusion protein was loaded onto a 10 mL Detoxi-Gel™ (immobilized polymixin-B, Pierce, product #20339) column equilibrated with PBS. The sample was left bound to the resin for 2.5 h before eluting with PBS. 151 mL fractions were collected. A typical SDS-PAGE gel of the fractions eluted is shown in FIG. 10. Individual fractions were assayed for β-lactamase activity using the nitrocefin plate assay and for endotoxin using the BioWhittaker QCL-1000 Chromogenic Endpoint LAL assay. Endotoxin units per mg of TAB protein were calculated. The maximum limit for in vivo murine studies was 5 U/mg.

Example 6

Binding of TAB2.4 and TAB2.5 to TAG-72 Preparations

Antigens for binding were coated as follows. All assays were performed using high binding capacity 96-well plates (Costar 9018). BSM (Sigma) was coated at 10 μg/mL in 100 μL PBS for either 2 h at room temperature or >16 h at 4° C. Tumor extract was coated at 1 μg/well in PBS and the plate was air dried at 25° C. O/N in an incubator. Tumor extract was generated from a pool of several LS174T xenografts from mice. Tumor pool was treated with T-per (Pierce #78510) (1 mL per 100 mg of tumor) and Halt protease inhibitor (PIERCE, #78410, 100×) was added 1× concentration and the tumor was homogenized. The T-per suspension was shaken at RT for 20 min to resuspend cells and then spun at 10,000 rpm for 15 min. The supernatant was collected as tumor extract (TE) and was aliquoted and frozen at −80° C. BCA (Biorad) assay was performed on the cell lysate to determine protein concentration. For antigen CA72-4 which is a purified form of TAG-72 purified from human fluids available commercially (Bioprocessing Inc., stock at 43,504 U/mL), 100 μL of a 1/1000 dilution was coated in PBS for 16 h at 4° C. After coating, wells were washed three times with PBST and blocked for 2 h with 200 μL PBST. Various concentrations of TAB molecules were added in a final volume of 100 μL in PBST and incubated for 2 h at room temperature with shaking. Unbound material was washed three times with PBST and bound TAB was detected by adding 200 μL nitrocefin solution followed by OD at 490 nm for 15 min.

TAB2.5 bound to all tested TAG-72 antigens. Binding signal varied depending on the antigen and CA 72-4 antigen gave low binding signal compared to BSM and tumor extract (see FIG. 11). TAB2.4 and TAB2.5 bound to coated BSM with similar affinity (see FIG. 12) and had similar off-rates (see FIG. 13, as measured above). In all cases, saturation of the binding signal was not obtained at the highest concentration of TAB tested.

Competition assays were also performed. BSM or tumor extract were coated in a 96-well plate as described previously. After washing and blocking the wells, 5 000 U of TAB2.5 was added with various concentrations of competitors in a final volume of 100 μL in PBST. The competitors used were BSM (Sigma, assuming a molecular weight of 150 kDa), STn biotinylated multimer (TAG-72, Glycotech #01-059), tumor extract (TE) from LS174T cells and CA 72-4 (BioProcessing). Biotinylated STn multimer is a purified synthetic form of TAG-72 that may also be recognized by TAB conjugate. TAB2.5 in the presence of competitor was incubated for 2 h at room temperature with agitation and unbound material was washed three times with PBST and bound TAB2.5 was measured by adding 200 μL nitrocefin solution and reading kinetic OD at 490 nm for 15 min. FIGS. 14 and 15 show that BSM inhibits binding of TAB2.5 to tumor extract and BSM with $IC_{50}$'s of ~300 nM and ~200 nM, respectively. TAB2.5 binding to either BSM or tumor extract was not inhibited by tumor extract, CA72-4 or STn in the conditions tested (up to 150 μg/mL for tumor extract, up to ~2200 U/mL for CA72-4 and up to 850 nM for STn).

Example 7

Construction of Charge Variant Libraries

To study the impact of protein net charge on pharmacokinetic parameters of the TAB2.5 protein, we constructed 4 libraries to either increase or decrease net charge based on the scFv, or on the beta-lactamase portion of the molecule. Using a modified version of Multi-site Quikchange Mutagenesis (Stratagene, CA) protocol as described before. (see, for example, WO US04/30085, which is incorporated by reference, herein; including any drawings); 4 libraries were made to either increase or decrease the net charge of TAB2.5 with libraries based in the scFv, and two based in beta-lactamase. Library ME384 was created in beta-lactamase to increase the charge by replacing certain non-conserved positively charged residues with arginine or lysine, and ME385 was created to decrease the net charge by substituting aspartic acid or glutamic acid. Libraries ME386 and ME387 were created in the same manner in the scFv, to increase or decrease the net charge respectively. Libraries ME384 and ME385 were created using 17 and 20 phosphorylated primers respectively, as shown in Table 2. Libraries ME386 and ME387 were created using 14 and 15 phosphorylated primers respectively, as shown in Table 3. All primers were HPLC purified. The 4 individual reactions were set up with combined primer concentrations of 0.4 μM, using pME374.4 as template. After mutagenesis and DpnI digestion, 1.5 μL out of 25 μL PCR reaction mix was transformed into *E. coli* TOP10F' cells followed by selection on LA+20 mg/L CMP+0.1 mg/L CTX plates. 96 clones from each library were screened for improved expression in 96-well microtiter plates as described below.

TABLE 2

Sequence of primers used for beta-lactamase mutagenesis of TAB2.5 protein. Primer name corresponds to the amino acid to be changed, its position, and the intended mutation (mutated codon shown in upper case). All primers used in beta-actamase mutagenesis are named starting with B. So, BE5R corresponds to Glu (E) at position 5 of beta-lactamase to be changed to Arg (R). The numbering is based on the first residue of beta-lactamase. All primers were designed to the sense strand.

| Name | Sequence (5'-3') | Length | SEQ ID NO |
|---|---|---|---|
| | Primers for TAB2.5 charge mutagenesis ME384 beta-lactamase charge increase | | |
| BE5R | [Phos]AACACCGGTGTCACGCAAACAGCTGGCGGAGGTGGTCG | 38 | 46 |
| BE10K | [Phos]AAACAGCTGGCGAAAGTGGTCGCGAATACGATTACC | 36 | 47 |
| BD76R | [Phos]TTTTAGGTGGGCGCGCCATTGCTCGCGGTGAAATTTC | 37 | 48 |
| BD86R | [Phos]GAAATTTCGCTGCGCGATGCGGTGACCAGATACTGG | 36 | 49 |
| BE124R | [Phos]ACAGGTACCGGATCGCGTCACGGATAACGCCTCCCTG | 37 | 50 |
| BD127R | [Phos]GATGAGGTCACGCGCAACGCCTCCCTGCTGCGC | 33 | 51 |
| BE171R | [Phos]TGGCATGCCCTATCGCCAGGCCATGACGACGCGGGTC | 37 | 52 |
| BD185K | [Phos]CCGCTCAAGCTGAAACATACCTGGATTAACGTGCCG | 36 | 53 |
| BE196R | [Phos]CCGAAAGCGGAACGCGCGCATTACGCCTGGGGCTATC | 37 | 54 |
| BD217R | [Phos]CCGGGTATGCTGCGCGCACAAGCCTATGGCGTGAAAAC | 38 | 55 |
| BE241R | [Phos]AAACATGGCGCCGCGCAACGTTGCTGATGCCTCAC | 35 | 56 |
| BD245R | [Phos]GGAGAACGTTGCTCGCGCCTCACTTAAGCAGGGCATC | 37 | 57 |
| BE279K | [Phos]CAACTGGCCCGTGAAAGCCAACACGGTGGTCGAGAC | 36 | 58 |
| BE285R | [Phos]CAACACGGTGGTCCGCACGAGTTTTGGTAATGTAGC | 36 | 59 |
| BE331R | [Phos]GGCCTTTATTCCTCGCAAGCAGATCGGTATTGTGATG | 37 | 60 |
| BE351K | [Phos]CCGGCACGCGTTAAAGCGGCATACCATATCCTCGAG | 36 | 51 |
| BE358K | [Phos]ATACCATATCCTCAAAGCGCTACAGTAGGAATTCGAG | 37 | 62 |
| | ME385 beta-lactamase charge decrease | | |
| BK6E | [Phos]ACCGGTGTCAGAAGAACAGCTGGCGGAGGTGGTCGCG | 37 | 63 |
| BK21E | [Phos]TACCCCGCTGATGGAAGCCCAGTCTGTTCCAGGCATG | 37 | 64 |
| BK37E | [Phos]TATTTATCAGGGAGAACCGCACTATTACACATTTGG | 36 | 65 |
| BK45E | [Phos]TACACATTTGGCGAAGCCGATATCGCGGCGAATAAAC | 37 | 66 |
| BK52E | [Phos]ATCGCGGCGAATGAACCCGTTACGCCTCAGACCCTG | 36 | 67 |
| BR80E | [Phos]GATGCCATTGCTGAAGGTGAAATTTCGCTGGACGATG | 37 | 68 |
| | Primers for TAB2.5 charge mutagenesis ME384 beta-lactamase charge increase | | |
| BR91E | [Phos]GATGCGGTGACCGAATACTGGCCACAGCTGACGGG | 35 | 69 |
| BK99E | [Phos]AGCTGACGGGCGAACAGTGGCAGGGTATTCGTATG | 35 | 70 |
| BR105D | [Phos]TGGCAGGGTATTGATATGCTGGATCTCGCCACCTAC | 36 | 71 |
| BR133D | [Phos]ACGCCTCCCTGCTGGATTTTTATCAAAACTGGCAGCC | 37 | 72 |
| BK143D | [Phos]CAGCCGCAGTGGGATCCTGGCACAACGCGTCTTTAC | 36 | 73 |
| BK164D | [Phos]GCGCTGGCGGTCGATCCTTCTGGCATGCCCTATGAG | 36 | 74 |

TABLE 2-continued

Sequence of primers used for beta-lactamase mutagenesis of TAB2.5 protein. Primer name corresponds to the amino acid to be changed, its position, and the intended mutation (mutated codon shown in upper case). All primers used in beta-actamase mutagenesis are named starting with B. So, BE5R corresponds to Glu (E) at position 5 of beta-lactamase to be changed to Arg (R). The numbering is based on the first residue of beta-lactamase. All primers were designed to the sense strand.

| Name | Sequence (5'-3') | Length | SEQ ID NO |
|---|---|---|---|
| BK180D | [Phos]GACGCGGGTCCTTGATCCGCTCAAGCTGGACCATAC | 36 | 75 |
| BK183D | [Phos]CTTAAGCCGCTCGATCTGGACCATACCTGGATTAAC | 36 | 76 |
| BK193E | [Phos]GATTAACGTGCCGGAAGCGGAAGAGGCGCATTACGC | 36 | 77 |
| BK249E | [Phos]TGATGCCTCACTTGAACAGGGCATCGCGCTGGCGCAG | 37 | 78 |
| BR261E | [Phos]AGTCGCGCTACTGGGAAATCGGGTCAATGTATCAGGG | 37 | 79 |
| BK309E | [Phos]GGCTCCCCCGGTCGAAGCGTCCTGGGTCCATAAAAC | 36 | 80 |
| BK332E | [Phos]TTTATTCCTGAAGAACAGATCGGTATTGTGATGCTC | 36 | 81 |
| BR349E | [Phos]TCCGAACCCGGCAGAAGTTGAGGCGGCATACCATATC | 37 | 82 |

TABLE 3

Sequence of primers used for scFv mutagenesis of TAB2.5 protein. Primer name corresponds to the amino acid to be changed in the light (L) or heavy (H) chan, its position, and the intended mutation (mutated codon shown in upper case). So, HD8R corresponds to Asp (D) at position 8 of the heavy chain to be changed to Arg (R). The numbering is based on the Kabat system for both the light and heavy chains. All primers were designed to the sense strand.

| Name | Sequence (5'-3') | Length | SEQ ID NO |
|---|---|---|---|
| Primers for TAB2.5 charge mutagenesis ME386 scFv charge increase | | | |
| HD8R | [Phos]GTTACAGCAGTCACGCGCGGAGTTGGTGAAACCGGG | 36 | 83 |
| HE10R | [Phos]CAGTCAGATGCGCGCTTGGTGAAACCGGGCGCGAG | 35 | 84 |
| HE42R | [Phos]TAAAACAGAACCCGCGCCAGGGCCTGGAGTGGATTGG | 37 | 85 |
| HE46K | [Phos]GGAACAGGGCCTGAAATGGATTGGGTATTTCAGCCC | 36 | 86 |
| HE61R | [Phos]CTTTAAGTATAACCGCCGCTTTAAAGGTAAAGCCAC | 36 | 87 |
| HD72K | [Phos]ACCCTGACGGCGAAAAAATCGTCGTCCACTGCTTAC | 36 | 88 |
| HE85R | [Phos]CAGTCTCACGTCACGCGATAGCGCGGTGTATTTCTG | 36 | 89 |
| LD1R | [Phos]GGCGGTGGATCTCGCATTGTCATGACCCAATCTCC | 35 | 90 |
| LE17K | [Phos]GTGAGTGTTGGAAAAAAGGTGACGCTGAGTTGCAAAAG | 38 | 91 |
| LE55K | [Phos]GCCTCTACCCGTAAATCCGGTGTTCCAGATCGTTTC | 36 | 92 |
| LD60K | [Phos]TCCGGTGTTCCAAAACGTTTCACCGGCAGTGGTTC | 35 | 93 |
| LD70K | [Phos]GGTTCGGGCACTAAATTTACACTGTCCATTTCGTC | 35 | 94 |
| LE79K | [Phos]ATTTCGTCTGTGAAAACAGAAGACCTGGCTGTCTAC | 36 | 95 |
| LE81K | [Phos]GTCTGTGGAAACAAAAGACCTGGCTGTCTACTATTG | 36 | 96 |

TABLE 3-continued

Sequence of primers used for scFv mutagenesis of TAB2.5 protein. Primer name corresponds to the amino acid to be changed in the light (L) or heavy (H) chan, its position, and the intended mutation (mutated codon shown in upper case). So, HD8R corresponds to Asp (D) at position 8 of the heavy chain to be changed to Arg (R). The numbering is based on the Kabat system for both the light and heavy chains. All primers were designed to the sense strand.

| Name | Sequence (5'-3') | Length | SEQ ID NO |
|---|---|---|---|
| ME387scFv charge decrease | | | |
| HK13E | [Phos]TGCGGAGTTGGTGGAACCGGGCGCGAGCGTAAAGATTTC | 39 | 97 |
| HK19E | [Phos]GGCGCGAGCGTAGAAATTTCTTGTAAAGCATCCGG | 35 | 98 |
| HK23E | [Phos]AAAGATTTCTTGTGAAGCATCCGGCTACACCTTTAC | 36 | 99 |
| HK38E | [Phos]CATTCACTGGGTAGAACAGAACCCGGAACAGGGCCTG | 37 | 100 |
| HK58E | [Phos]TAATGATGACTTTGAATATAACGAACGCTTTAAAGG | 36 | 101 |
| HR62D | [Phos]TAAGTATAACGAAGATTTTAAAGGTAAAGCCACCCTG | 37 | 102 |
| HK64E | [Phos]ATAACGAACGCTTTGAAGGTAAAGCCACCCTGACGGC | 37 | 103 |
| HK73D | [Phos]CTGACGGCGGACGATTCGTCGTCCACTGCTTACCTG | 36 | 104 |
| LK18D | [Phos]GAGTGTTGGAGAAGATGTGACGCTGAGTTGCAAAAG | 36 | 105 |
| LK24E | [Phos]GACGCTGAGTTGCGAAAGCTCCCAAAGCCTGCTATAC | 37 | 106 |
| LK39E | [Phos]TGGTATCAGCAGGAACCAGGCCAGTCTCCTAAATTG | 36 | 107 |
| LK45E | [Phos]AGGCCAGTCTCCTGAATTGCTGATCTATTGGGCCTC | 36 | 108 |
| LR54E | [Phos]TTGGGCCTCTACCGAAGAATCCGGTGTTCCAGATCG | 36 | 109 |
| LK103E | [Phos]GGGCGGGTACTGAATTAGTTCTCAAAACACCGGTG | 35 | 110 |
| LK107E | [Phos]TAAATTAGTTCTCGAAACACCGGTGTCAGAAAAACAG | 37 | 111 |

Example 8

Screening of Charge Variant Libraries

One plate each of libraries MB384, ME385, ME386, ME387 were screened as previously described except that LB+10 mg/L CMP was used as the growth media and the cultures were grown at 30° C. for 48 h. Expression, measured as total BLA activity, BSM binding and off-rate were measured for all the clones and parent TAB2.5.

Figure 16:
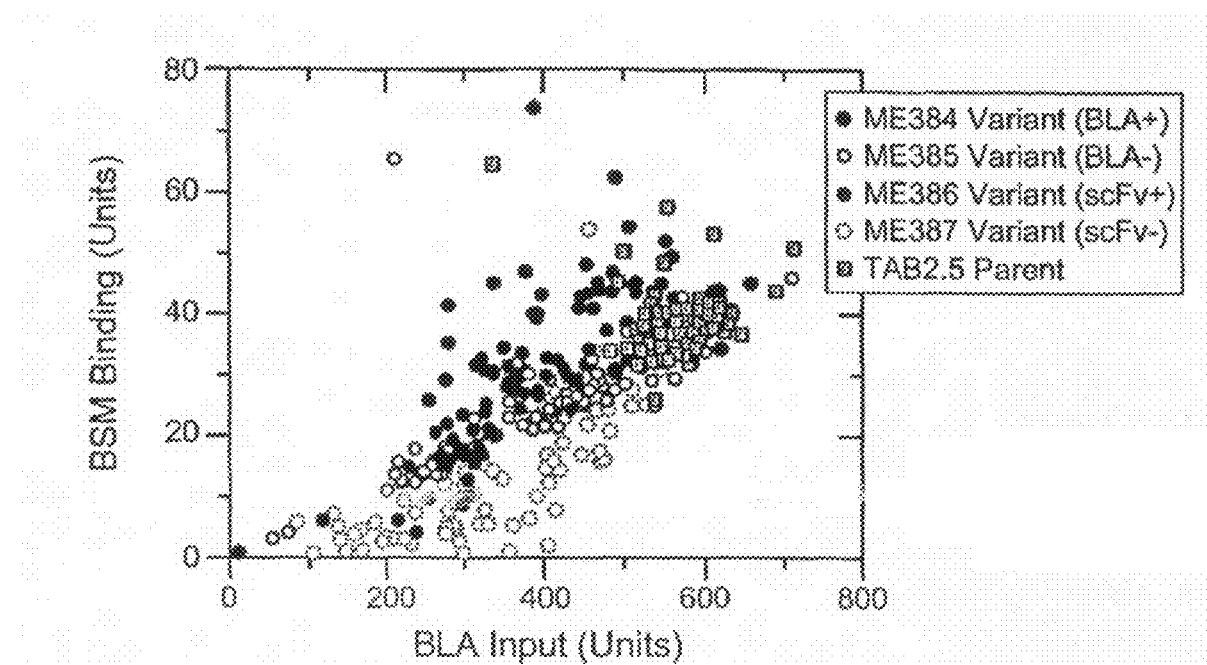

Many variants containing up to 3 charge reversal mutations in the BLA portion of the fusion were identified that expressed and bound in a similar fashion to TAB2.5. Also, many variants were identified that contained up to 7 charge reversal mutations in the scFv portion of the fusion protein and showed good expression and binding to BSM, similar to TAB2.5 parent (see FIG. 16). For further analysis, clones that had similar BSM binding and expressed well and that contained a range of net charges were picked. The B-per extracts for these clones were tested in quadruplicates (for expression and BSM binding) after being grown in 96-well format at 30° C. for 48 h. Furthermore, the choice of clones was narrowed down to 11 clones plus template TAB2.5. The mutations, net charge and theoretical pI of the clones is shown in Table 4. Clones that had similar binding to BSM and good enough expression were chosen. These were grown in 25 mL shake flasks containing TB medium with 10 μg/mL CMP for 48 h at 30° C. Expression (BLA activity), BSM and tumor extract (TE) binding and off-rates, intactness using western blot were measured and compared with wt template TAB2.5. A summary of the results is shown in Table 5 where many clones have characteristics similar to TAB2.5,

TABLE 4

List of clones selected for further analysis and their characteristics. h or l indicate mutations in the heavy or light chain, respectively.

| Clone name | # of mutation | Mutations | Net charge | pI |
|---|---|---|---|---|
| pME384.36 | 3 | E10K, D86R, E196R | 7.4 | 8.9 |
| pME385.95 | 4 | K21E, K37E, K99E, R261E | −6.6 | 5.7 |
| pME386.10 | 7 | lD1R, lE17K, lE55K, lD60K, lD70K, lE79K, lE81K | 15.3 | 9.3 |

TABLE 4-continued

List of clones selected for further analysis and their characteristics.
h or l indicate mutations in the heavy or light chain, respectively.

| Clone name | # of mutation | Mutations | Net charge | pI |
|---|---|---|---|---|
| pME386.19 | 4 | lE17K, lD60K, lD70K, lE79K | 9.4 | 9.0 |
| pME386.36 | 6 | hE46K, lD1R, lE55K, lD70K, lE79K, lE81K | 13.3 | 9.2 |
| pME386.41 | 3 | lE55K, lD70K, lE79K | 7.4 | 8.9 |
| pME386.74 | 5 | hE42R, lD1R, lE17K, lD70K, lE81K | 11.4 | 9.1 |
| pME387.28 | 4 | hK13E, hK23E, lK24E, lK103E | −6.6 | 5.7 |
| pME387.64 | 6 | hK13E, hK19E, lK64E, lK24E, lK45E, lK103E | −10.6 | 5.3 |
| pME387.75 | 5 | hK13E, hK23E, lK24E, lK45E, lK103E | −8.6 | 5.5 |
| pME387.91 | 7 | hK13E, hK23E, lK18D, lK24E, lK45E, lR54E, lK103E | −12.6 | 5.2 |
| TAB2.5 | 0 |  | 1.4 | 7.7 |

TABLE 5

Summary of the biochemical data generated for selected charge variant clones.

| Clone name | Expression | BSM binding | BSM off-rate | TE binding | TE off-rate | Western |
|---|---|---|---|---|---|---|
| pME384.36 | = | − | = | − | = | = |
| pME385.95 | − | − | =+ | − | = | − |
| pME386.10 | −− | = | −−− | = | = | − |
| pME386.19 | = | − | = | = | = | = |
| pME386.36 | − | − | −−− | = | = | −−− |
| pME386.41 | = | = | + | = | = | − |
| pME386.74 | − | = | =− | = | = | −− |
| pME387.28 | =+ | = | + | − | = | = |
| pME387.64 | − | − | −− | − | = | − |
| pME387.75 | = | = | = | = | = | − |
| pME387.91 | − | − | − | = | = | = |
| TAB2.5 | = | = | = | = | = | = |

Example 9

Construction and Testing of TAB2.6

AmpC or TAB2.5 was replaced with TEM-4 β-lactamase, which is approximately 100 amino acids smaller and may affect plasma clearance. Plasmid pME381.10 contains TAB2.5 and suitable restriction sites to swap β-lactamase. TEM-4 was amplified from a mutant of pLITMUS39 (New England Biolabs, Beverly, Mass.), a plasmid having increased activity on cephalosporins [Long-McGie, J., A. D. Liu and V. Schellenberger (2000) *Biotechnol. Bioeng.* 68, 121-125, Rapid in vivo evolution of a β-lactamase using phagemids] using primers ME363F (5'-ACTAAATTAGT-TCTCAAAACACCGGTGCACCCA-GAAACGCTGGTGAAAG-3') (SEQ ID NO: 112) and ME363R (5'-CGTTTGATCTCGAGTGCGGCCG-CAAGCTTGTCGACGGAGCTCGTTAC-CAATGCTTAATCA GTGAGG-3') (SEQ ID NO: 113) containing restriction sites PinAI and NotI. The PCR product was purified using a Qiaquick PCR purification kit (Qiagen), and both pME381.10 and PCR product were digested with PinAI and NotI. The approx. 850 bp insert fragment and 4.1 kb vector fragment were gel purified. Fragments were ligated together overnight, followed by purification and transformation into *E. coli* TOP10F' (Invitrogen, Carlsbad, Calif.) competent cells and selection on LA+20 mg/L CMP+0.1 mg/L CTX plates. Two colonies were selected and sequenced, and plasmid pME382.1 was chosen as TAB2.6. TAB2.6 was expressed and a B-per extract was prepared as described previously. BLA activity and binding to BSM was measured. TAB2.6 expressed, but the amount of BLA activity observed is low compared to TAB2.5 (10-fold less), data not shown.

Example 10

Construction and Testing of TAB2.7

Another version of β-lactamase replacing ampC with a stabilized version of ampC created in previous experiments (see, Amin, N., Liu, A. D., Ramer, S., Aehle, W., Meijer, D., Metin, M., Wong, S., Gualfetti, P., Schellenberger, V. (2004) *Protein Engineering, Design, and Selection,* 17, 787-793). Plasmid pME381.10 contains TAB2.5 and suitable restriction sites to swap β-lactamase. Our stabilized β-lactamase was PCR amplified from plasmid pNA04.17 using primers ME365F (5'-ACTAAATTAGTTCTCAAACACCGGTGT-CAGAAAAACAGCTG-3') (SEQ ID NO: 114) and ME365R (5'-CGTTTGATCTCGAGTGCGGCCGCAAGCT-TGTCGACGGAGCTCGTTACTGTAGCGCCTCTA GGATATGG-3') (SEQ ID NO: 115) containing restriction sites PinAI and NotI. The PCR product was purified using a Qiaquick PCR purification kit (Qiagen), and both pME381.10 and PCR product were digested with PinAI and NotI. The approximately 1.1 kb insert fragment and 4.1 kb vector fragment were gel purified. Fragments were ligated together overnight, followed by transformation into *E. coli* TOP10F' (Invitrogen, Carlsbad, Calif.) competent cells and selection on LA+20 mg/L CMP+0.1 mg/L CTX plates. One colony was selected and sequenced, and plasmid pME388.1 was chosen as TAB2.7.

TAB2.5 and TAB2.7 were grown in 25 mL shake flask cultures and B-per extracts were prepared as described previously. Expression of TAB2.7 was 5-fold higher than TAB2.5.

Both molecules were tested for protease stability. Thermolysin protease was prepared at a stock concentration of 2.5 mg/mL in imidazol/HCl buffer. The stock solution was then diluted 5-fold in series to give thermolysin concentrations 500 μg/mL, 100 μg/mL, 20 μg/mL, and 4 μg/mL and one without protease. 87 μL of each extract was added to 800 μL buffer containing the various concentration of thermolysin and incubated 1 h at 37° C. in a water bath.

The protease was then inactivated by adding 200 μL of 10 mM EDTA. All samples were tested for remaining BLA activity by adding 20 μL of the sample to 180 μL of nitrocephin substrate. These plates were read at 490 nm in 5 min at room temperature in a kinetic assay. The samples were also compared for remaining BSM binding activity as previously described. BSM binding was not measured for protease-treated TAB2.5 because the BLA portion of the molecule was too unstable to have a read out for the assay.

Figure 17:
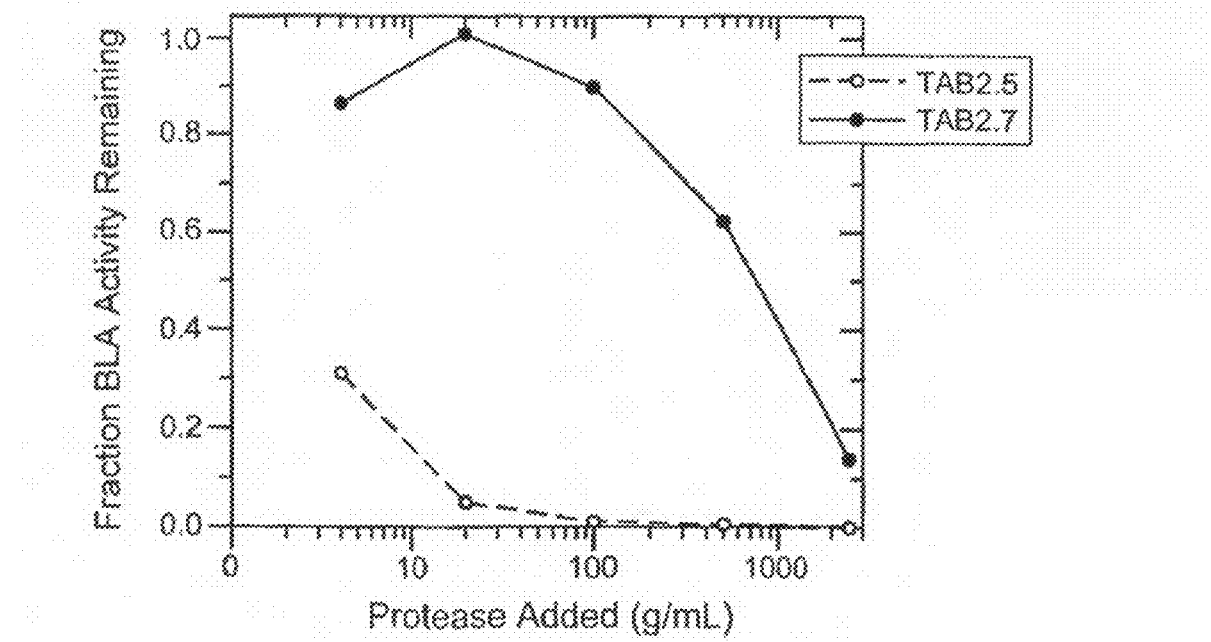
Figure 18:
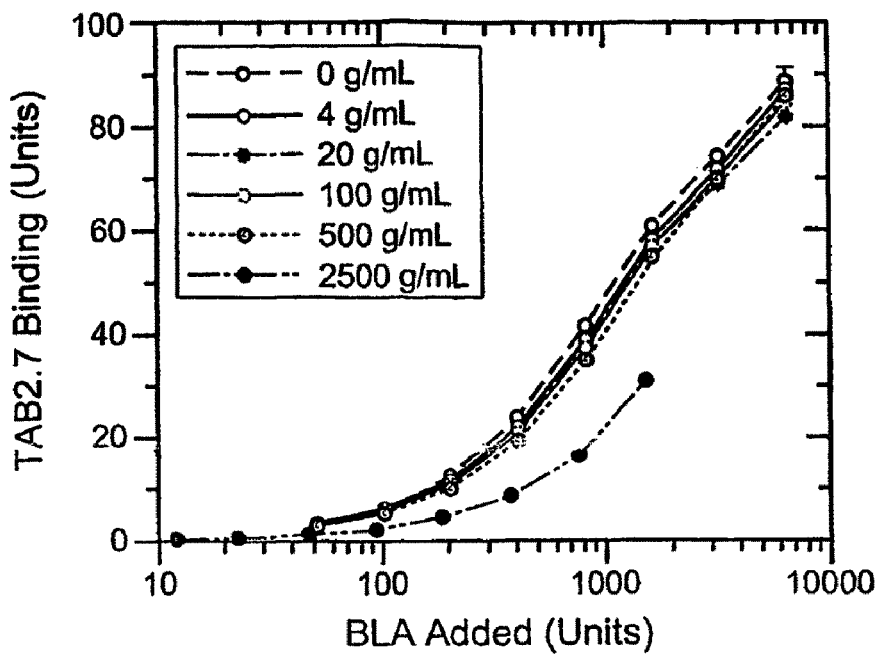

To test the effect of protease on the TAB scFv, TAB32.7 was tested, which has the exact same scFv as does TAB2.5, but with a much more stable BLA. As can be seen from FIG. 17, the stabilized version of BLA in TAB2.7 is more protease stable than the one in TAB2.5 as expected. TAB2.7's binding to BSM was not affected until the highest concentration of thermolysin used of 2.5 mg/mL (see FIG. 18). The data indicate that the scFv portion of TAB2.5, as well as TAB2.7, is more stable to thermolysin treatment than the BLA portion of the fusion protein.

Example 11

Cysteine Bond Between Light and Heavy Chain of svFv

In an effort to stabilize TAB2.7, we placed a disulfide bond between the heavy and light chains of the scFv by substituting a cysteine in each chain. The position of the disulfide bond was determined by modeling the protein (see, for example, V. S. Dani, C. Ramakrishnan and R. Varadarajan (2003) Protein Engineering 16, 187-193). Plasmid pME388.1 (TAB2.7) was modified using a modified version of Multi-site Quikchange Mutagenesis (Stratagene, CA) protocol as described before (see, for example, WO US04/30085, which is incorporated by reference, herein, including any drawings). Using template pME388.1, the reaction was set up with 100 ng each of 2 phosphorylated primers. TABLL46C; 5'-[Phos]CAGTCTC-CTAAATGCCTGATCTATTGGGCCTCTAC-3' (SEQ ID NO: 116) for replacement of light chain Leu46 with Cys and TABHA101C; 5'-[Phos]AGCCTTAACATGTGCTAT-TGGGGTCAAGGGACCAGC-3' (SEQ ID NO: 117) for replacement of heavy chain Ala101 with Cys. After mutagenesis and DpnI digestion, 1.5 μL out of 25 μL PCR reaction mix was transformed into E. coli TOP10F' cells followed by selection on LA+20 mg/L+0.1 mg/L CTX plates. 30 colonies resulted, and 12 were picked for sequencing. Sequencing of these clones revealed that 4 contained mutations (3 IL46C, 1 hA101C), but none of them had both together. Clone pME395.1 (hA101C) was chosen for a new round of mutagenesis with 100 ng of the TABLL46C primer alone. This reaction was performed as above, and 12 colonies resulted. All 12 were picked for sequencing, and pME403.3 had the additional cysteine. This construct was chosen for further stability and expression studies.

Figure 19:
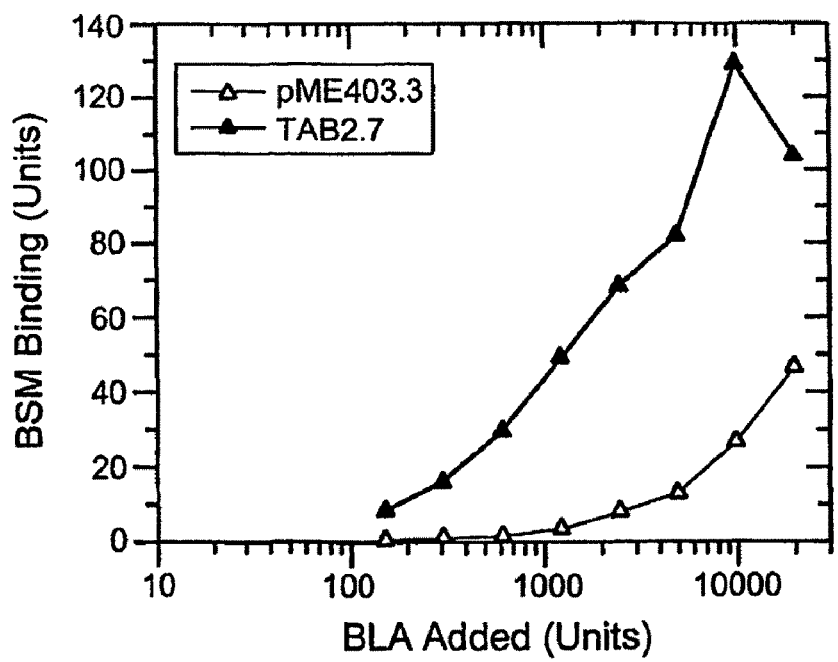

The variant was expressed and a B-per extract was prepared as described previously. BLA activity and binding to BSM were measured. pME403.3 expressed well, but ~35% less than TAB2.7 and the B-per extract contained only 35% intact protein compared to 85% for TAB2.7 (data not shown). The binding affinity to coated BSM was reduced by ~40-fold (see, FIG. 19). The data thus suggest that mutations of residues IL46 and hA101 to cysteines affected stability and binding affinity of the protein. More variants could be designed and tested, according to this protocol.

Example 12

Thermal Stability of TAB2 Variants

Figure 20:
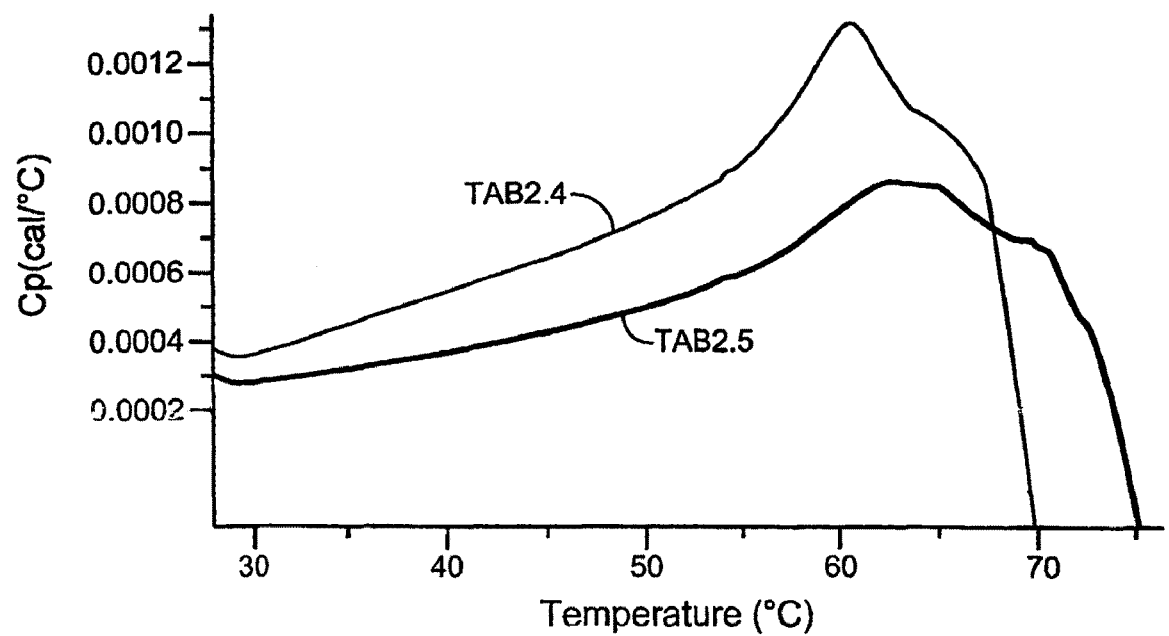

DSC thermograms were collected on a VP DSC from Micorocal. Buffer conditions were phosphate buffered saline at pH 7.4 and protein concentration was ~0.7 mg/mL based on BLA activity. Data was collected from 25 to 90° C. with a scan rate of 90° C./hour. TAB2.5 is more stable (~2° C.) than TAB2.4 and may be less prone to aggregation (see, FIG. 20). The transition is broader and less cooperative.

Example 13

Immunohistochemistry of TAB2.5

Figure 21:
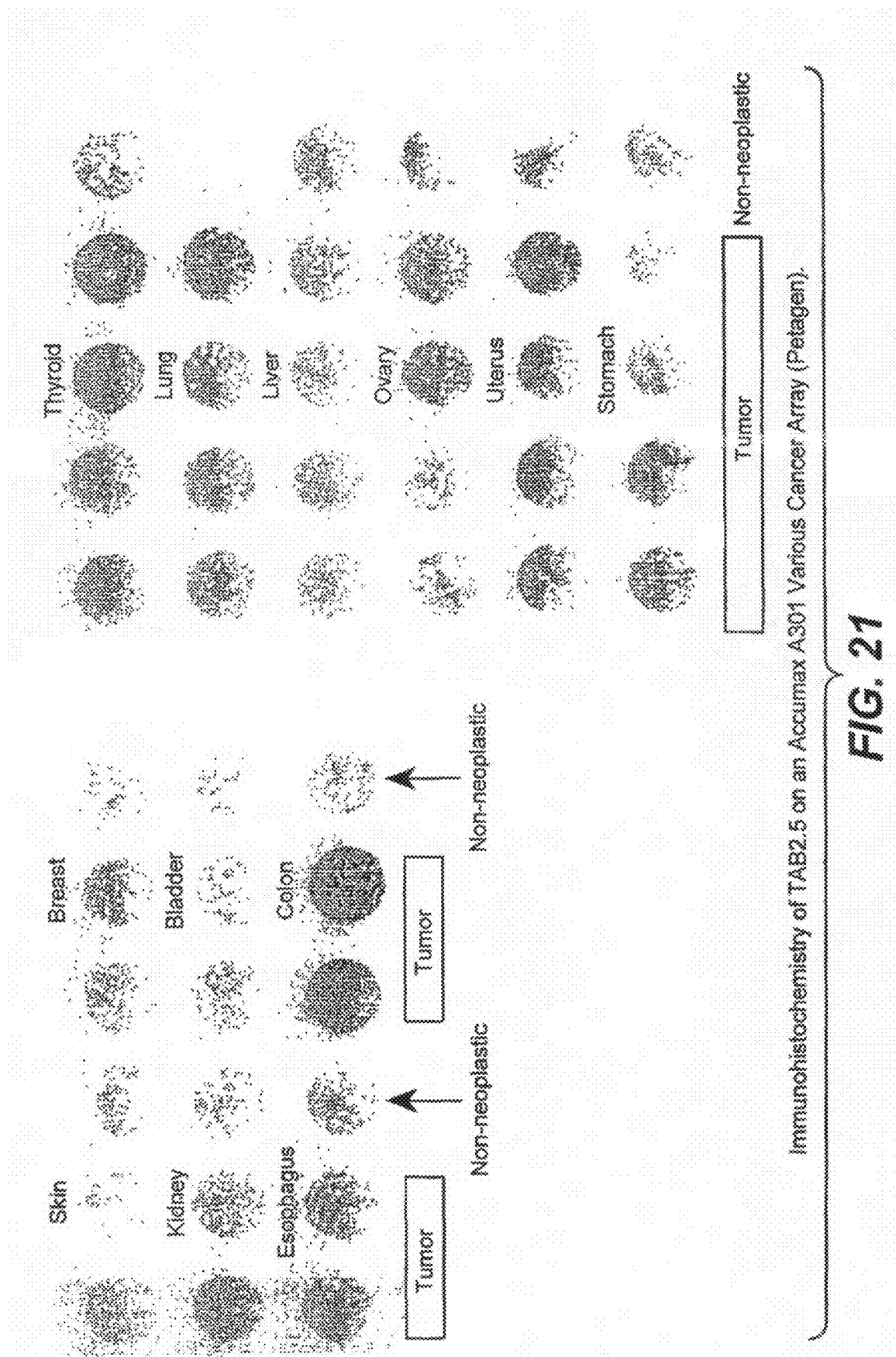
Figure 22:
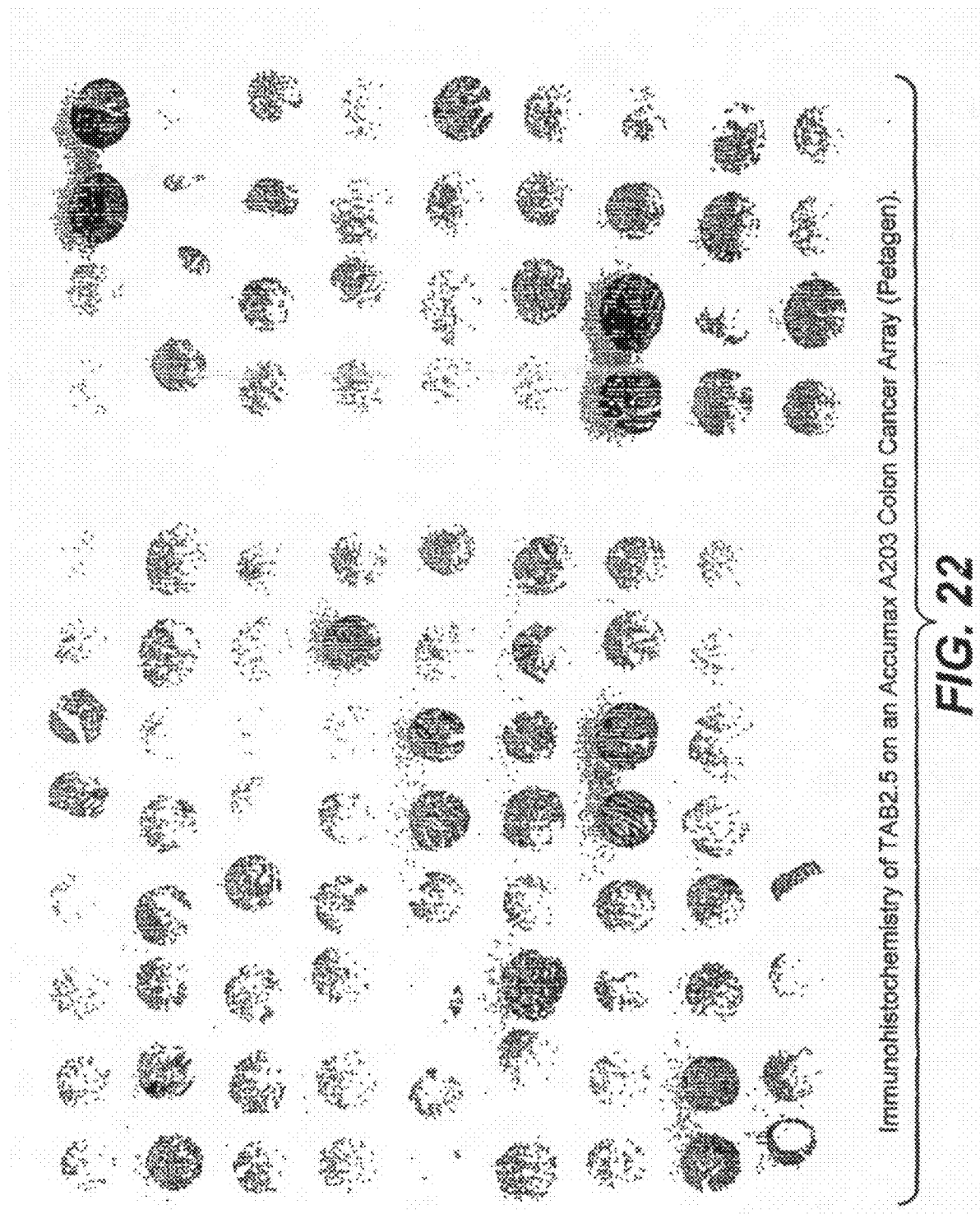

Immunohistochemistry of TAB2.5 was performed on an Accumax A301 various cancer array and A203 Colon Cancer array (Petagen) using the following method:
Deparaffinize with Histo-Clear, 2× for 5 min (National Diagonistics, catalog #HS-200)
Rehydrate in graded ethanol series (2 min each of 100%, 95%, 75%, 50% ethanol, DI water)
Heat-Based Antigen Retrieval (30 min, 1 mM EDTA, pH 8.0 at 90° C.)
Incubate sections in PBS containing 1% normal goat serum for 20 min
Block endogenous peroxidase activity with DAKO Peroxidase Blocking Solution for 10 min
Wash slides for 1 min in TBS
Incubate sections with TAB2.5 for 30 min (10 μg/mL, diluted in PBS containing 1% normal goat serum)
Wash slides for 5 min in TBS
Incubate sections with ROPO2 (see, for example, U.S. Ser. No. 60/636,002, which is incorporated by reference, herein, including any drawings) for 30 min (0.15 μg/mL, anti-BLA rabbit polyclonal, diluted in PBS containing 1% normal goat serum)
Wash slides for 5 min in TBS
Incubate sections with DAKO anti-rabbit antibody for 30 min (DakoCytomation Rabbit Envision+System-HRP, DAB, catalog #K4010)
Wash slides for 5 min in TBS
Incubate sections in DAKO Peroxidase substrate solution for 3-5 min until desired staining intensity develops
Rinse slides in DI water
Counterstain with Haemotoxylin, clear and mount In this initial assessment of TAB2.5 tissue binding by IHC using a various cancer array, a strong signal was observed for one colon cancer and weaker signals for uterus and stomach cancer sections, while no binding was observed for any of the normal tissues (see FIG. 21). In a colon cancer tissue array, positive TAB 2.5 staining of several human colon tumors ranging from mild to very strong was observed (see FIG. 22). A magnification of one of the colon tumor samples is shown (see FIG. 23).

Example 14

Pharmacokinetics and Tissue Distribution of TAB2.4 in a Xenograft Mouse Model of Human Colorectal Cancer Female Ncr athymic nude mice, 18-22 g, approximately 6-10 weeks of age, were implanted subcutaneously with approximately 2 million tumor-derived LS174T human colorectal cancer cells. LS174T cells were obtained from the ATCC, passaged through mice and re-isolated to generate TLS174T. When tumors reached approximately 200-300 mm³, 30 animals were administered a single IV bolus injection of TAB2.4 (1 mg/kg) via the tail vein. Three animals were anaesthetized and sacrificed at pre-dosing, 2, 15, 30 min, 1, 2, 4, 8, 24, 48, and 72 h, respectively. Tumors were harvested from each animal at 8, 24, 48, and 72 h, snap frozen in liquid nitrogen, and stored at approximately −70° C. until analysis. Blood was collected via cardiac puncture onto EDTA containing tubers. Blood samples were centrifuged to separate plasma, which was then stored at −70° C. until analysis.

The tissue samples were homogenized on ice in PBS with 15 μg/mL aprotinin (2 mL buffer: gram tissue). The homogenate was mixed with T-per (1:1) (from Pierce) and centrifuged. TAB2.4 concentrations in the tissue supernatant and plasma samples were determined by measuring β-lactamase (BLA) activity using a capture BLA nitrocefin assay, according to the following.
1. Coat high binding capacity (HBC) plates (Costar #9018) with 5 μg/mL of either chicken polyclonal anti-BLA antibody (PAS 3313/3314), 100 μL/well, O/N at 4° C.;
2. Wash the plate 3× with 1× PBS/0.05% Tween-20 (PBST);
3. Block the plate with 250 μL/well of Blocker Casein in PBS (Pierce #37528) for 2 h at room temperature with gentle shaking;
4. Wash the plate 3× with PBST;
5. Add 20 μL plasma samples or tissue supernatant to each well, then diluted it with 80 μL/well of Blocker Casein buffer, incubate for 2 h at room temperature with gentle shaking;
6. Wash 6× with PBST;
7. Add 200 μL/well of nitrocefin substrate solution;
8. Read kinetics at 490 nm for 15 min.

Figure 24:
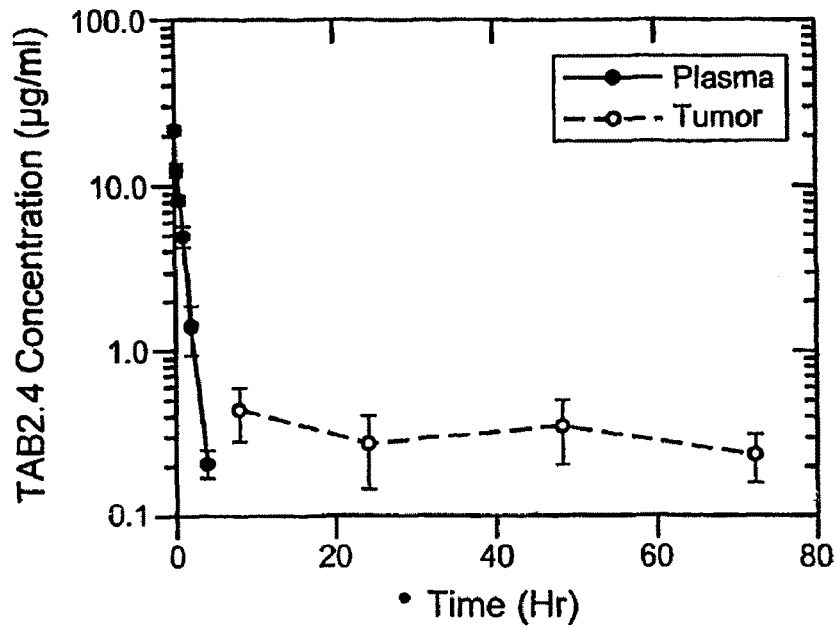

The results of this experiment demonstrate that TAB2.4 was rapidly eliminated from plasma and localized to the TLS174T tumor (see FIG. 24). High tumor to blood ratio of TAB2.4 concentrations were achieved and sustained.

Example 15

Pharmacokinetics of TAB2.5 in Non-Tumor Bearing Male Sprague Dawley Rats

Three male Sprague Dawley rats, 300-350 g, approximately 6-8 weeks of age, were administered a single IV bolus injection of TAB 2.5 (1 mg/kg) via the femoral vein catheter. Blood samples were drawn via jugular vain catheter at pre-dosing, 2, 5, 15, 30 min 1, 2, 4, 8, 12, 24, and 48 h onto EDTA containing tubes, and were centrifuged to separate plasma, which was then stored at −70° C. until analysis.

Figure 25:
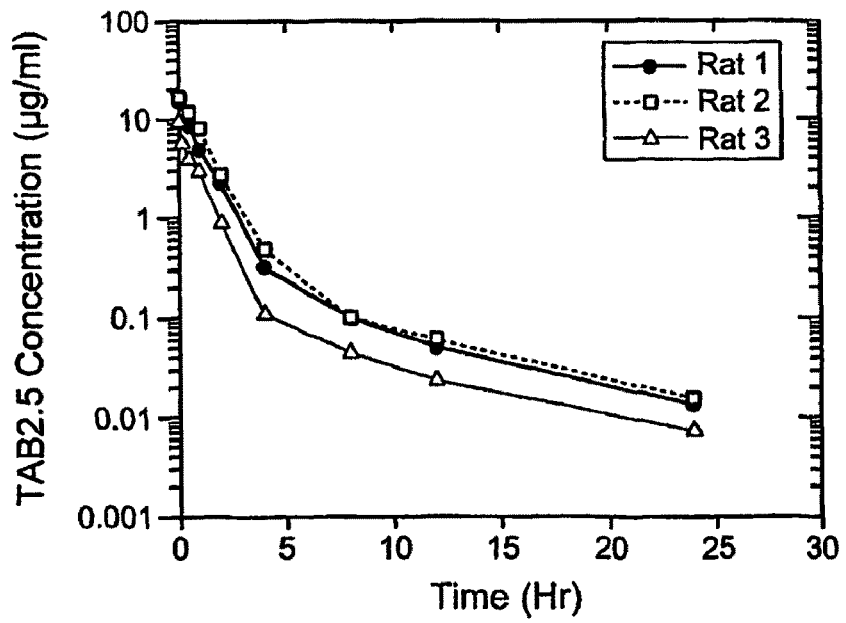

Plasma TAB2.5 concentrations were determined by a capture BLA nitrocefin assay described above. The results of this experiment indicated that following an intravenous injection, plasma TAB2.5 disposition was biphasic with a rapid distribution $t_{1/2\alpha}$ of 0.63 h followed by a slow terminal $t_{1/2\beta}$ of 6 h (see, FIG. 25). More than 50% of drug exposure occurred within 1 h. The drug clearance was 0.27 mL/min and the volume of distribution (16 mL) was similar to the plasma volume.

Example 16

Efficacy of TAB2.5 in a Xenograft Mouse Model of Human Colorectal Cancer

Ncr athymic nude mice, 18-22 g, approximately 6-8 weeks of age, were implanted subcutaneously with 5 million tumor-derived LS174T human colorectal cancer cells. LS174T cells were obtained from ATCC, passaged through mice and re-isolated to generate TLS174T. When the tumors reached the size range of 50-150 mm³, the animals were randomized for tumor volume into two groups with ten animals per group so that there was no significant difference between the groups. The animals were administered vehicle (group 1) or TAB2.5 (1 mg/kg, group 2). Following 24 h, the animals that received TAB2.5 were administered GC-Mel at a dose of 150 mg/kg. All drugs were administered by IV bolus injections via the tail vein. Tumors were measured twice weekly. The average tumor volumes for each group are plotted versus (Study) Days in FIG. 26. This demonstrated that TAB2.5 at 1 m/kg in combination with the prodrug GC-Mel at 150 mg/kg are active in inhibiting the growth of TLS174T tumor cells a mouse model of human colorectal cancer.

Example 17

Construction of TAB2.8

TAB 2.8 consists of an scFv fused to ampC (*Euterobacter cloacae*) β-lactamase. The scFv was based on TAB2.5 scFv (vH-linker-vL), but the heavy and light chains are reversed (vL-linker-vH). The scFv containing the reversed chains was synthesized by DNA2.0 (Menlo Park), also containing restriction sites NcoI and PinAI flanking 5' and 3' of the gene respectively. Both pME381.10 (TAB2.5 cloning vector) and the synthesized gene (pG00931) were cut with NcoI and PinAI. The approx. 784 bp insert fragment and 4.4 kb vector fragment were gel purified. Fragments were ligated together overnight, followed by transformation into *E. coli* TOP10F' (Invitrogen, Carlsbad, Calif.) competent cells and selection on LA+Cm20+0.1 CTX plates. Two colonies were selected and sequenced, and plasmid pME411.1 was chosen as TAB2.8.

TAB2.8 and TAB2.5 in TOP10F' were grown in 600 ml of TB-10 μg/ml cmp for 48 h at 30° C. The culture was spun 15 min at 10 000 rpm and the cell lysate was recovered by treating with 50 ml B-PER at room temperature for 60 min and then spinning 15 min at 10 000 rpm. The TAB proteins were purified as described earlier using a 5 ml PBA column. 20 μL of ~5 mg/ml PBA purified material was loaded onto an analytical size exclusion column (SEC, Phenomenex Biosep-SEC-S 3000; 600×7.8 mm) and the monomer was purified by running the column at 1 mL/min in PBS. The monomer peak was manually collected between 16.5 and 17.5 min of elution. The monomers of TAB2.5 and TAB2.8 were compared in a binding assay against coated BSM and tumor extract (TE) as described previously.

Example 18

TAB2.8 Binding

Bound BLA activity was plotted against the concentration of free TAB to determine $K_D$'s as shown in FIG. 27. The software Graphit ver. 3.01 curve fitting tool for binding to one site was used to calculate the $K_D$'s. TAB2.5 and TAB2.8 have $K_D$'s of 45 and 9.9 nM, respectively to coated BSM while the $K_D$'s are 19 and 4.1 nM against TE. In both cases, TAB2.8 had ~4-fold better affinity than TAB2.5 indicating that the vL-vH orientation in TAB2.8 is better than the vH-vL in TAB25. Expression was about 2-fold down for TAB2.8 compared to TAB2.5.

Having described the preferred embodiments of the present invention, it will appear to those ordinarily skilled in the art that various modifications may be made to the disclosed embodiments, and that such modifications are intended to be within the scope of the present invention. One skilled in the art would readily appreciate that the present invention is well adapted to carry out the objects and obtain the ends and advantages mentioned, as well as those inherent. The molecular complexes and the methods, procedures, treatments, molecules and specific compounds are presently representative of preferred embodiments, are exemplary and are not intended as limitations on the scope of the invention. It will be readily apparent to one skilled in the art that varying substitutions and modifications may be made to the invention without departing from the scope and spirit of the invention.

All patents and publications mentioned in the specification are indicative of the levels of those skilled in the art to which the invention pertains. All patents and publications are incorporated by reference to the same extent as if each individual publication was specifically and individually indicated to be incorporated by reference.

The invention may be practiced in the absence of any element or elements, limitation or limitations not specifically disclosed herein. The terms and expressions which have been employed are used as terms of description and not of limitation, and there is no intention that in the use of such terms and expressions of excluding any equivalents of the features shown and described (or portions), but it is recognized that various modifications are possible within the scope of the invention claimed. It should be understood that although the present invention has been specifically disclosed by preferred embodiments and optional features, modification and variation of the concepts herein disclosed may be resorted to by those skilled in the art, and that such modifications and variations are considered to be within the scope of this invention.

The invention has been described broadly and generically. Each of the narrower species and subgeneric groupings falling within the generic disclosure also form part of the invention. This includes the generic description of the invention with a proviso or negative limitation removing any subject matter from the genus, regardless of whether or not the excised material is specifically recited.

What is claimed:

1. An antibody-enzyme conjugate comprising:
   a. a scFv comprising heavy and light chains joined by a linker sequence, wherein said antibody-enzyme conjugate comprises a TAB 2.5 molecule comprising SEQ ID NO:20 or a TAB 2.8 molecule comprising SEQ ID NO:22, and wherein the scFv is capable of specifically binding to TAG-72 antigen, and
   b. an enzyme conjugated to the scFv which is capable of converting a prodrug to an active drug.

2. A composition comprising the antibody-enzyme conjugate of claim 1.

3. The antibody-enzyme conjugate of claim 1, wherein the enzyme is a beta-lactamase.

4. The antibody-enzyme conjugate of claim 3, wherein the beta-lactamase comprises the amino acid sequence set out in SEQ ID NO:4.

5. The antibody-enzyme conjugate of claim 1, wherein the prodrug is a melphalan derivative, an auristatin, a camptothecin, a phosphate-containing prodrug, a thiophosphate-containing prodrug, a sulfate-containing prodrug, a peptide-containing prodrug, a D-amino acid-modified pro-drug, a glycosylated prodrug, a beta-lactam-containing prodrug, an optionally substituted phenoxyacetamide-containing prodrug, an optionally substituted phenylacetamide containing prodrug, a 5-fluorocytosine prodrug, or a 5-fluorouridine prodrug.

6. The antibody-enzyme conjugate of claim 1, wherein the drug is an etoposide, a temposide, an adriamycin, a daunomycin, a caminomycin, an aminopterin, a dactinomycin, a mitomycins, a cis-platinum or cis-platinum analogue, a bleomycin, an esperamicin, 5-fluorouracil, melphalan, or a nitrogen mustard.

* * * * *

UNITED STATES PATENT AND TRADEMARK OFFICE
CERTIFICATE OF CORRECTION

PATENT NO.       : 8,101,728 B2
APPLICATION NO.  : 11/885492
DATED            : January 24, 2012
INVENTOR(S)      : Judith A. Fox et al.

Page 1 of 1

It is certified that error appears in the above-identified patent and that said Letters Patent is hereby corrected as shown below:

In Claim 6, column 120, line 57, delete "caminomycin" and insert -- carminomycin --.

Signed and Sealed this
First Day of May, 2012

David J. Kappos
*Director of the United States Patent and Trademark Office*

```
                            SEQUENCE LISTING

<160> NUMBER OF SEQ ID NOS: 119

<210> SEQ ID NO 1

<400> SEQUENCE: 1

000

<210> SEQ ID NO 2
<211> LENGTH: 619
<212> TYPE: PRT
<213> ORGANISM: Artificial Sequence
<220> FEATURE:
<223> OTHER INFORMATION: Synthetic Tab 2.4 protein

<400> SEQUENCE: 2

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Val Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Asp Ile Val Met Ser Gln Ser Pro Ser Ser Leu Pro Val Ser Val
145                 150                 155                 160

Gly Glu Lys Val Thr Leu Ser Cys Lys Ser Ser Gln Ser Leu Leu Tyr
                165                 170                 175
```

```
Ser Gly Asn Gln Lys Asn Tyr Leu Ala Trp Tyr Gln Gln Lys Pro Gly
            180                 185                 190

Gln Ser Pro Lys Leu Leu Ile Tyr Trp Ala Ser Ala Arg Glu Ser Gly
        195                 200                 205

Val Pro Asp Arg Phe Thr Gly Ser Gly Ser Gly Thr Asp Phe Thr Leu
    210                 215                 220

Ser Ile Ser Ser Val Lys Thr Glu Asp Leu Ala Val Tyr Tyr Cys Gln
225                 230                 235                 240

Gln Tyr Tyr Ser Tyr Pro Leu Thr Phe Gly Ala Gly Thr Lys Leu Val
                245                 250                 255

Leu Lys Thr Pro Val Ser Glu Lys Gln Leu Ala Glu Val Val Ala Asn
            260                 265                 270

Thr Ile Thr Pro Leu Met Lys Ala Gln Ser Val Pro Gly Met Ala Val
        275                 280                 285

Ala Val Ile Tyr Gln Gly Lys Pro His Tyr Tyr Thr Phe Gly Lys Ala
    290                 295                 300

Asp Ile Ala Ala Asn Lys Pro Val Thr Pro Gln Thr Leu Phe Glu Leu
305                 310                 315                 320

Gly Ser Ile Ser Lys Thr Phe Thr Gly Val Leu Gly Gly Asp Ala Ile
                325                 330                 335

Ala Arg Gly Glu Ile Ser Leu Asp Asp Ala Val Thr Arg Tyr Trp Pro
            340                 345                 350

Gln Leu Thr Gly Lys Gln Trp Gln Gly Ile Arg Met Leu Asp Leu Ala
        355                 360                 365

Thr Tyr Thr Ala Gly Gly Leu Pro Leu Gln Val Pro Asp Glu Val Thr
    370                 375                 380

Asp Asn Ala Ser Leu Leu Arg Phe Tyr Gln Asn Trp Gln Pro Gln Trp
385                 390                 395                 400

Lys Pro Gly Thr Thr Arg Leu Tyr Ala Asn Ala Ser Ile Gly Leu Phe
                405                 410                 415

Gly Ala Leu Ala Val Lys Pro Ser Gly Met Pro Tyr Glu Gln Ala Met
            420                 425                 430

Thr Thr Arg Val Leu Lys Pro Leu Lys Leu Asp His Thr Trp Ile Asn
        435                 440                 445

Val Pro Lys Ala Glu Glu Ala His Tyr Ala Trp Gly Tyr Arg Asp Gly
    450                 455                 460

Lys Ala Val Arg Val Ser Pro Gly Met Leu Asp Ala Gln Ala Tyr Gly
465                 470                 475                 480

Val Lys Thr Asn Val Gln Asp Met Ala Asn Trp Val Met Ala Asn Met
                485                 490                 495

Ala Pro Glu Asn Val Ala Asp Ala Ser Leu Lys Gln Gly Ile Ala Leu
            500                 505                 510

Ala Gln Ser Arg Tyr Trp Arg Ile Gly Ser Met Tyr Gln Gly Leu Gly
        515                 520                 525

Trp Glu Met Leu Asn Trp Pro Val Glu Ala Asn Thr Val Val Glu Thr
    530                 535                 540

Ser Phe Gly Asn Val Ala Leu Ala Pro Leu Pro Val Ala Glu Val Asn
545                 550                 555                 560

Pro Pro Ala Pro Pro Val Lys Ala Ser Trp Val His Lys Thr Gly Ser
                565                 570                 575

Thr Gly Gly Phe Gly Ser Tyr Val Ala Phe Ile Pro Glu Lys Gln Ile
            580                 585                 590

Gly Ile Val Met Leu Ala Asn Thr Ser Tyr Pro Asn Pro Ala Arg Val
        595                 600                 605
```

-continued

```
Glu Ala Ala Tyr His Ile Leu Glu Ala Leu Gln
    610             615

<210> SEQ ID NO 3
<211> LENGTH: 243
<212> TYPE: PRT
<213> ORGANISM: Artificial Sequence
<220> FEATURE:
<223> OTHER INFORMATION: synthetic CC49 protein

<400> SEQUENCE: 3

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Val Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Gly Gly Gly Ser Gly Gly Gly Gly
        115                 120                 125

Gly Ser Asp Ile Val Met Ser Gln Ser Pro Ser Ser Leu Pro Val Ser
    130                 135                 140

Val Gly Glu Lys Val Thr Leu Ser Cys Lys Ser Ser Gln Ser Leu Leu
145                 150                 155                 160

Tyr Ser Gly Asn Gln Lys Asn Tyr Leu Ala Trp Tyr Gln Gln Lys Pro
                165                 170                 175

Gly Gln Ser Pro Lys Leu Leu Ile Tyr Trp Ala Ser Ala Arg Glu Ser
            180                 185                 190

Gly Val Pro Asp Arg Phe Thr Gly Ser Gly Ser Gly Thr Asp Phe Thr
        195                 200                 205

Leu Ser Ile Ser Ser Val Lys Thr Glu Asp Leu Ala Val Tyr Tyr Cys
    210                 215                 220

Gln Gln Tyr Tyr Ser Tyr Pro Leu Thr Phe Gly Ala Gly Thr Lys Leu
225                 230                 235                 240

Val Leu Lys

<210> SEQ ID NO 4
<211> LENGTH: 266
<212> TYPE: PRT
<213> ORGANISM: Unknown
<220> FEATURE:
<223> OTHER INFORMATION: beta-lactamase protein

<400> SEQUENCE: 4

Thr Pro Val His Pro Glu Thr Leu Val Lys Val Lys Asp Ala Glu Asp
1               5                   10                  15

Gln Leu Gly Ala Arg Val Gly Tyr Ile Glu Leu Asp Leu Asn Ser Gly
            20                  25                  30

Lys Ile Leu Glu Ser Phe Arg Pro Glu Glu Arg Phe Pro Met Met Ser
        35                  40                  45
```

```
Thr Phe Lys Val Leu Leu Cys Gly Ala Val Leu Ser Arg Val Asp Ala
 50                  55                  60
Gly Gln Glu Gln Leu Gly Arg Arg Ile His Tyr Ser Gln Asn Asp Leu
 65                  70                  75                  80
Val Lys Tyr Ser Pro Val Thr Glu Lys His Leu Thr Asp Gly Met Thr
                 85                  90                  95
Val Arg Glu Leu Cys Ser Ala Ala Ile Thr Met Ser Asp Asn Thr Ala
                100                 105                 110
Ala Asn Leu Leu Leu Thr Thr Ile Gly Gly Pro Lys Glu Leu Thr Ala
                115                 120                 125
Phe Leu His Asn Met Gly Asp His Val Thr Arg Leu Asp Arg Trp Glu
            130                 135                 140
Pro Glu Leu Asn Glu Ala Ile Pro Asn Asp Glu Arg Asp Thr Thr Met
145                 150                 155                 160
Pro Val Ala Met Ala Thr Thr Leu Arg Lys Leu Leu Thr Gly Glu Leu
                165                 170                 175
Leu Thr Leu Ala Ser Arg Gln Gln Leu Ile Asp Trp Met Glu Ala Asp
                180                 185                 190
Lys Val Ala Gly Pro Leu Leu Arg Ser Ala Leu Pro Ala Gly Trp Phe
            195                 200                 205
Ile Ala Asp Lys Ser Gly Ala Gly Glu Arg Gly Ser Arg Gly Ile Ile
        210                 215                 220
Ala Ala Leu Gly Pro Asp Gly Lys Pro Ser Arg Ile Val Val Ile Tyr
225                 230                 235                 240
Thr Thr Gly Ser Gln Ala Thr Met Asp Glu Arg Asn Arg Gln Ile Ala
                245                 250                 255
Glu Ile Gly Ala Ser Leu Ile Lys His Trp
            260                 265
```

<210> SEQ ID NO 5
<211> LENGTH: 1815
<212> TYPE: DNA
<213> ORGANISM: Artificial Sequence
<220> FEATURE:
<223> OTHER INFORMATION: synthetic sequence encoding Tab 2.1 protein

<400> SEQUENCE: 5

```
caggtgcagt tacagcagtc agatgcggag ttggtgaaac cgggcgcgag cgtaaagatt      60
tcttgtaaag catccggcta cacctttacc gaccatgcca ttcactgggt aaaacagaac     120
ccggaacagg gcctggagtg gattgggtat tcagcccggg taatgatga ctttaagtat      180
aacgaacgct ttaaaggtaa agccacctg acggcggaca atcgtcgtc cactgcttac      240
gtccagctga cagtctcac gtcagaagat agcgcggtgt atttctgtac gcgtagcctt      300
aacatggcgt attggggtca agggaccagc gtgaccgtta gcagcggggg cggcggttcc      360
ggtggaggtg gaagtggcgg cggtggatct gatattgtca tgagtcaatc tccgtcatca      420
ctgcccgtga gtgttggaga aaaggtgacg ctgagttgca aaagctccca aagcctgcta      480
tacagcggca atcagaagaa ttatctggca tggtatcagc agaaaccagg ccagtctcct      540
aaattgctga tctattgggc ctctgcacgt gaatccggtg ttccagatcg tttcaccggc      600
agtggttcgg gcactgattt tacactgtcc atttcgtctg tgaaaacaga agacctggct      660
gtctactatt gccaacaata ctactcatat ccgcttacct ttggggcggg tactaaatta      720
gttctcaaaa caccggtgtc agaaaaacag ctggcgaggg tggtcgcgaa tacgattacc      780
ccgctgatga agcccagtc tgttccaggc atggcggtgg ccgttattta tcagggaaaa      840
```

-continued

```
ccgcactatt acacatttgg caaggccgat atcgcggcga ataaacccgt tacgcctcag     900
accctgttcg agctgggttc tataagtaaa accttcaccg gcgttttagg tggggatgcc     960
attgctcgcg gtgaaatttc gctggacgat gcggtgacca gatactggcc acagctgacg    1020
ggcaagcagt ggcagggtat tcgtatgctg gatctcgcca cctacaccgc tggcggcctg    1080
ccgctacagg taccggatga ggtcacggat aacgcctccc tgctgcgctt ttatcaaaac    1140
tggcagccgc agtggaagcc tggcacaacg cgtctttacg ccaacgccag catcggtctt    1200
tttggtgcgc tggcggtcaa accttctggc atgccctatg agcaggccat gacgacgcgg    1260
gtccttaagc cgctcaagct ggaccatacc tggattaacg tgccgaaagc ggaagaggcg    1320
cattacgcct gggctatcg tgacggtaaa gcggtgcgcg tttcgccggg tatgctggat     1380
gcacaagcct atggcgtgaa aaccaacgtg caggatatgg cgaactgggt catgcaaaac    1440
atggcgccgg agaacgttgc tgatgcctca cttaagcagg gcatcgcgct ggcgcagtcg    1500
cgctactggc gtatcgggtc aatgtatcag ggtctgggct gggagatgct caactggccc    1560
gtggaggcca acacggtggt cgagacgagt tttggtaatg tagcactggc gccgttgccc    1620
gtggcagaag tgaatccacc ggctcccccg gtcaaagcgt cctgggtcca taaaacgggc    1680
tctactggcg ggtttggcag ctacgtggcc tttattcctg aaaagcagat cggtattgtg    1740
atgctcgcga atacaagcta tccgaacccg gcacgcgttg aggcggcata ccatatcctc    1800
gaggcgctac agtag                                                     1815
```

<210> SEQ ID NO 6
<211> LENGTH: 604
<212> TYPE: PRT
<213> ORGANISM: Artificial Sequence
<220> FEATURE:
<223> OTHER INFORMATION: synthetic Tab 2.1 protein

<400> SEQUENCE: 6

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Val Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Ser Gly Gly Gly Ser Gly Gly Gly Gly Gly
        115                 120                 125

Gly Ser Asp Ile Val Met Ser Gln Ser Pro Ser Ser Leu Pro Val Ser
    130                 135                 140

Val Gly Glu Lys Val Thr Leu Ser Cys Lys Ser Ser Gln Ser Leu Leu
145                 150                 155                 160

Tyr Ser Gly Asn Gln Lys Asn Tyr Leu Ala Trp Tyr Gln Gln Lys Pro
                165                 170                 175

Gly Gln Ser Pro Lys Leu Leu Ile Tyr Trp Ala Ser Ala Arg Glu Ser
            180                 185                 190
```

-continued

Gly Val Pro Asp Arg Phe Thr Gly Ser Gly Ser Gly Thr Asp Phe Thr
             195                 200                 205

Leu Ser Ile Ser Ser Val Lys Thr Glu Asp Leu Ala Val Tyr Tyr Cys
         210                 215                 220

Gln Gln Tyr Tyr Ser Tyr Pro Leu Thr Phe Gly Ala Gly Thr Lys Leu
225                 230                 235                 240

Val Leu Lys Thr Pro Val Ser Glu Lys Gln Leu Ala Glu Val Val Ala
             245                 250                 255

Asn Thr Ile Thr Pro Leu Met Lys Ala Gln Ser Val Pro Gly Met Ala
             260                 265                 270

Val Ala Val Ile Tyr Gln Gly Lys Pro His Tyr Thr Phe Gly Lys
             275                 280                 285

Ala Asp Ile Ala Ala Asn Lys Pro Val Thr Pro Gln Thr Leu Phe Glu
         290                 295                 300

Leu Gly Ser Ile Ser Lys Thr Phe Thr Gly Val Leu Gly Gly Asp Ala
305                 310                 315                 320

Ile Ala Arg Gly Glu Ile Ser Leu Asp Asp Ala Val Thr Arg Tyr Trp
             325                 330                 335

Pro Gln Leu Thr Gly Lys Gln Trp Gln Gly Ile Arg Met Leu Asp Leu
             340                 345                 350

Ala Thr Tyr Thr Ala Gly Gly Leu Pro Leu Gln Val Pro Asp Glu Val
         355                 360                 365

Thr Asp Asn Ala Ser Leu Leu Arg Phe Tyr Gln Asn Trp Gln Pro Gln
370                 375                 380

Trp Lys Pro Gly Thr Thr Arg Leu Tyr Ala Asn Ala Ser Ile Gly Leu
385                 390                 395                 400

Phe Gly Ala Leu Ala Val Lys Pro Ser Gly Met Pro Tyr Glu Gln Ala
             405                 410                 415

Met Thr Thr Arg Val Leu Lys Pro Leu Lys Leu Asp His Thr Trp Ile
             420                 425                 430

Asn Val Pro Lys Ala Glu Glu Ala His Tyr Ala Trp Gly Tyr Arg Asp
         435                 440                 445

Gly Lys Ala Val Arg Val Ser Pro Gly Met Leu Asp Ala Gln Ala Tyr
450                 455                 460

Gly Val Lys Thr Asn Val Gln Asp Met Ala Asn Trp Val Met Ala Asn
465                 470                 475                 480

Met Ala Pro Glu Asn Val Ala Asp Ala Ser Leu Lys Gln Gly Ile Ala
             485                 490                 495

Leu Ala Gln Ser Arg Tyr Trp Arg Ile Gly Ser Met Tyr Gln Gly Leu
             500                 505                 510

Gly Trp Glu Met Leu Asn Trp Pro Val Glu Ala Asn Thr Val Val Glu
             515                 520                 525

Thr Ser Phe Gly Asn Val Ala Leu Ala Pro Leu Pro Val Ala Glu Val
530                 535                 540

Asn Pro Pro Ala Pro Pro Val Lys Ala Ser Trp Val His Lys Thr Gly
545                 550                 555                 560

Ser Thr Gly Gly Phe Gly Ser Tyr Val Ala Phe Ile Pro Glu Lys Gln
             565                 570                 575

Ile Gly Ile Val Met Leu Ala Asn Thr Ser Tyr Pro Asn Pro Ala Arg
         580                 585                 590

Val Glu Ala Ala Tyr His Ile Leu Glu Ala Leu Gln
             595                 600

<210> SEQ ID NO 7

<211> LENGTH: 1860
<212> TYPE: DNA
<213> ORGANISM: Artificial Sequence
<220> FEATURE:
<223> OTHER INFORMATION: synthetic sequence encoding Tab 2.4 protein

<400> SEQUENCE: 7

| | | | | | |
|---|---|---|---|---|---|
| caggtgcagt | tacagcagtc | agatgcggag | ttggtgaaac | cgggcgcgag | cgtaaagatt | 60 |
| tcttgtaaag | catccggcta | cacctttacc | gaccatgcca | ttcactgggt | aaaacagaac | 120 |
| ccggaacagg | gcctggagtg | gattgggtat | ttcagcccgg | gtaatgatga | ctttaagtat | 180 |
| aacgaacgct | ttaaaggtaa | agccaccctg | acggcggaca | atcgtcgtc | cactgcttac | 240 |
| gtccagctga | acagtctcac | gtcagaagat | agcgcggtgt | atttctgtac | gcgtagcctt | 300 |
| aacatggcgt | attgggtca | aggaccagc | gtgaccgtta | gcagcggtgg | tggcggttcg | 360 |
| ggtggcggag | gcagcggtgg | aggggctct | ggggcggcg | gttccggtgg | aggtggaagt | 420 |
| ggcggcggtg | gatctgatat | tgtcatgagt | caatctccgt | catcactgcc | cgtgagtgtt | 480 |
| ggagaaaagg | tgacgctgag | ttgcaaaagc | tcccaaagcc | tgctatacag | cggcaatcag | 540 |
| aagaattatc | tggcatggta | tcagcagaaa | ccaggccagt | ctcctaaatt | gctgatctat | 600 |
| tgggcctctg | cacgtgaatc | cggtgttcca | gatcgtttca | ccggcagtgg | ttcgggcact | 660 |
| gattttacac | tgtccatttc | gtctgtgaaa | acagaagacc | tggctgtcta | ctattgccaa | 720 |
| caatactact | catatccgct | tacctttggg | gcgggtacta | aattagttct | caaaacaccg | 780 |
| gtgtcagaaa | aacagctggc | ggaggtggtc | gcgaatacga | ttaccccgct | gatgaaagcc | 840 |
| cagtctgttc | caggcatggc | ggtggccgtt | atttatcagg | gaaaaccgca | ctattacaca | 900 |
| tttggcaagg | ccgatatcgc | ggcgaataaa | cccgttacgc | ctcagaccct | gttcgagctg | 960 |
| ggttctataa | gtaaaaccTT | caccggcgtt | ttaggtgggg | atgccattgc | tcgcggtgaa | 1020 |
| atttcgctgg | acgatgcggt | gaccagatac | tggccacagc | tgacgggcaa | gcagtggcag | 1080 |
| ggtattcgta | tgctggatct | cgccacctac | accgctggcg | gcctgccgct | acaggtaccg | 1140 |
| gatgaggtca | cggataacgc | ctccctgctg | cgcttttatc | aaaactggca | gccgcagtgg | 1200 |
| aagcctggca | caacgcgtct | ttacgccaac | gccagcatcg | gtcttttttgg | tgcgctggcg | 1260 |
| gtcaaaccTT | ctggcatgcc | ctatgagcag | gccatgacga | cgcgggtcct | taagccgctc | 1320 |
| aagctggacc | atacctggat | taacgtgccg | aaagcggaag | aggcgcatta | cgcctggggc | 1380 |
| tatcgtgacg | gtaaagcggt | gcgcgtttcg | ccgggtatgc | tggatgcaca | agcctatggc | 1440 |
| gtgaaaacca | acgtgcagga | tatggcgaac | tgggtcatgg | caaacatggc | gccggagaac | 1500 |
| gttgctgatg | cctcacttaa | gcagggcatc | gcgctggcgc | agtcgcgcta | ctggcgtatc | 1560 |
| gggtcaatgt | atcagggtct | gggctgggag | atgctcaact | ggcccgtgga | ggccaacacg | 1620 |
| gtggtcgaga | cgagttttgg | taatgtagca | ctggcgccgt | tgcccgtggc | agaagtgaat | 1680 |
| ccaccggctc | ccccggtcaa | agcgtcctgg | tccataaaa | cgggctctac | tggcgggttt | 1740 |
| ggcagctacg | tggcctttat | tcctgaaaag | cagatcggta | ttgtgatgct | cgcgaataca | 1800 |
| agctatccga | acccggcacg | cgttgaggcg | gcataccata | tcctcgaggc | gctacagtag | 1860 |

<210> SEQ ID NO 8
<211> LENGTH: 619
<212> TYPE: PRT
<213> ORGANISM: Artificial Sequence
<220> FEATURE:
<223> OTHER INFORMATION: Synthetic Tab 2.4 protein

<400> SEQUENCE: 8

-continued

```
Gln Val Gln Leu Gln Gln Ser Asp Ala Glu Leu Val Lys Pro Gly Ala
  1               5                  10                  15

Ser Val Lys Ile Ser Cys Lys Ala Ser Gly Tyr Thr Phe Thr Asp His
             20                  25                  30

Ala Ile His Trp Val Lys Gln Asn Pro Glu Gln Gly Leu Glu Trp Ile
         35                  40                  45

Gly Tyr Phe Ser Pro Gly Asn Asp Asp Phe Lys Tyr Asn Glu Arg Phe
     50                  55                  60

Lys Gly Lys Ala Thr Leu Thr Ala Asp Lys Ser Ser Thr Ala Tyr
 65                  70                  75                  80

Val Gln Leu Asn Ser Leu Thr Ser Glu Asp Ser Ala Val Tyr Phe Cys
                 85                  90                  95

Thr Arg Ser Leu Asn Met Ala Tyr Trp Gly Gln Gly Thr Ser Val Thr
            100                 105                 110

Val Ser Ser Gly Gly Gly Gly Ser Gly Gly Gly Gly Ser Gly Gly Gly
            115                 120                 125

Gly Ser Gly Gly Gly Gly Ser Gly Gly Gly Gly Ser Gly Gly Gly Gly
            130                 135                 140

Ser Asp Ile Val Met Ser Gln Ser Pro Ser Ser Leu Pro Val Ser Val
145                 150                 155                 160

Gly Glu Lys Val Thr Leu Ser Cys Lys Ser Ser Gln Ser Leu Leu Tyr
                165                 170                 175

Ser Gly Asn Gln Lys Asn Tyr Leu Ala Trp Tyr Gln Gln Lys Pro Gly
            180                 185                 190

Gln Ser Pro Lys Leu Leu Ile Tyr Trp Ala Ser Ala Arg Glu Ser Gly
        195                 200                 205

Val Pro Asp Arg Phe Thr Gly Ser Gly Ser Gly Thr Asp Phe Thr Leu
    210                 215                 220

Ser Ile Ser Ser Val Lys Thr Glu Asp Leu Ala Val Tyr Tyr Cys Gln
225                 230                 235                 240

Gln Tyr Tyr Ser Tyr Pro Leu Thr Phe Gly Ala Gly Thr Lys Leu Val
                245                 250                 255

Leu Lys Thr Pro Val Ser Glu Lys Gln Leu Ala Glu Val Val Ala Asn
            260                 265                 270

Thr Ile Thr Pro Leu Met Lys Ala Gln Ser Val Pro Gly Met Ala Val
        275                 280                 285

Ala Val Ile Tyr Gln Gly Lys Pro His Tyr Tyr Thr Phe Gly Lys Ala
    290                 295                 300

Asp Ile Ala Ala Asn Lys Pro Val Thr Pro Gln Thr Leu Phe Glu Leu
305                 310                 315                 320

Gly Ser Ile Ser Lys Thr Phe Thr Gly Val Leu Gly Gly Asp Ala Ile
                325                 330                 335

Ala Arg Gly Glu Ile Ser Leu Asp Asp Ala Val Thr Arg Tyr Trp Pro
            340                 345                 350

Gln Leu Thr Gly Lys Gln Trp Gln Gly Ile Arg Met Leu Asp Leu Ala
        355                 360                 365

Thr Tyr Thr Ala Gly Gly Leu Pro Leu Gln Val Pro Asp Glu Val Thr
    370                 375                 380

Asp Asn Ala Ser Leu Leu Arg Phe Tyr Gln Asn Trp Gln Pro Gln Trp
385                 390                 395                 400

Lys Pro Gly Thr Thr Arg Leu Tyr Ala Asn Ala Ser Ile Gly Leu Phe
                405                 410                 415

Gly Ala Leu Ala Val Lys Pro Ser Gly Met Pro Tyr Glu Gln Ala Met
            420                 425                 430
```

```
Thr Thr Arg Val Leu Lys Pro Leu Lys Leu Asp His Thr Trp Ile Asn
        435                 440                 445
Val Pro Lys Ala Glu Glu Ala His Tyr Ala Trp Gly Tyr Arg Asp Gly
    450                 455                 460
Lys Ala Val Arg Val Ser Pro Gly Met Leu Asp Ala Gln Ala Tyr Gly
465                 470                 475                 480
Val Lys Thr Asn Val Gln Asp Met Ala Asn Trp Val Met Ala Asn Met
            485                 490                 495
Ala Pro Glu Asn Val Ala Asp Ala Ser Leu Lys Gln Gly Ile Ala Leu
        500                 505                 510
Ala Gln Ser Arg Tyr Trp Arg Ile Gly Ser Met Tyr Gln Gly Leu Gly
        515                 520                 525
Trp Glu Met Leu Asn Trp Pro Val Glu Ala Asn Thr Val Val Glu Thr
    530                 535                 540
Ser Phe Gly Asn Val Ala Leu Ala Pro Leu Pro Val Ala Glu Val Asn
545                 550                 555                 560
Pro Pro Ala Pro Pro Val Lys Ala Ser Trp Val His Lys Thr Gly Ser
            565                 570                 575
Thr Gly Gly Phe Gly Ser Tyr Val Ala Phe Ile Pro Glu Lys Gln Ile
        580                 585                 590
Gly Ile Val Met Leu Ala Asn Thr Ser Tyr Pro Asn Pro Ala Arg Val
        595                 600                 605
Glu Ala Ala Tyr His Ile Leu Glu Ala Leu Gln
        610                 615

<210> SEQ ID NO 9
<211> LENGTH: 1860
<212> TYPE: DNA
<213> ORGANISM: Artificial Sequence
<220> FEATURE:
<223> OTHER INFORMATION: synthetic sequence encoding Tab 2.5 protein

<400> SEQUENCE: 9
caggtgcagt tacagcagtc agatgcggag ttggtgaaac cgggcgcgag cgtaaagatt      60
tcttgtaaag catccggcta cacctttacc gaccatgcca ttcactgggt aaaacagaac     120
ccggaacagg gcctggagtg gattgggtat ttcagcccgg gtaatgatga ctttaagtat     180
aacgaacgct ttaaaggtaa agccaccctg acggcggaca atcgtcgtc cactgcttac     240 ctgcagctga acagtctcac gtcagaagat agcgcggtgt atttctgtac gcgtagcctt     300
aacatggcgt attggggtca aggaccagc gtgaccgtta gcagcggtgg tgcggttcg       360 ggtggcggag gcagcggtgg aggggctct ggggcggcg gttccggtgg aggtggaagt       420
ggcggcggtg gatctgatat tgtcatgacc caatctccgt catcactgcc cgtgagtgtt     480
ggagaaaagg tgacgctgag ttgcaaaagc tcccaaagcc tgctatacag cggcaatcag     540
aagaattatc tggcatggta tcagcagaaa ccaggccagt ctcctaaatt gctgatctat     600
tgggcctcta cccgtgaatc cggtgttcca gatcgtttca ccggcagtgg ttcgggcact     660
gattttacac tgtccatttc gtctgtgaaa acagaagacc tggctgtcta ctattgccaa     720
caatactact catatccgct tacctttggg gcgggtacta aattagttct caaaacgccg     780
gtgtcagaaa acagctggc ggaggtggtc gcgaatacga ttccccgct gatgaaagcc      840 cagtctgttc aggcatggc ggtggccgtt atttatcagg gaaaccgca ctattacaca     900 tttggcaagg ccgatatcgc ggcgaataaa cccgttacgc ctcagaccct gttcgagctg     960
ggttctataa gtaaaacctt caccggcgtt ttaggtgggg atgccattgc tcgcggtgaa    1020
```

```
atttcgctgg acgatgcggt gaccagatac tggccacagc tgacgggcaa gcagtggcag    1080
ggtattcgta tgctggatct cgccacctac accgctggcg gcctgccgct acaggtaccg    1140
gatgaggtca cggataacgc ctccctgctg cgcttttatc aaaactggca gccgcagtgg    1200
aagcctggca caacgcgtct ttacgccaac gccagcatcg gtcttttttgg tgcgctggcg    1260 gtcaaacctt ctggcatgcc ctatgagcag gccatgacga cgcgggtcct taagccgctc    1320
aagctggacc atacctggat taacgtgccg aaagcggaag aggcgcatta cgcctggggc    1380
tatcgtgacg gtaaagcggt gcgcgtttcg ccgggtatgc tggatgcaca agcctatggc    1440
gtgaaaacca acgtgcagga tatggcgaac tgggtcatgg caaacatggc gccggagaac    1500
gttgctgatg cctcacttaa gcagggcatc gcgctggcgc agtcgcgcta ctggcgtatc    1560
gggtcaatgt atcagggtct gggctgggag atgctcaact ggcccgtgga ggccaacacg    1620
gtggtcgaga cgagttttgg taatgtagca ctggcgccgt tgcccgtggc agaagtgaat    1680
ccaccggctc ccccggtcaa agcgtcctgg gtccataaaa cgggctctac tggcgggttt    1740
ggcagctacg tggcctttat tcctgaaaag cagatcggta ttgtgatgct cgcgaataca    1800
agctatccga acccggcacg cgttgaggcg gcataccata tcctcgaggc gctacagtag    1860
```

<210> SEQ ID NO 10
<211> LENGTH: 619
<212> TYPE: PRT
<213> ORGANISM: Artificial Sequence
<220> FEATURE:
<223> OTHER INFORMATION: synthetic Tab 2.5 protein

<400> SEQUENCE: 10

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Asp Ile Val Met Thr Gln Ser Pro Ser Ser Leu Pro Val Ser Val
145                 150                 155                 160

Gly Glu Lys Val Thr Leu Ser Cys Lys Ser Ser Gln Ser Leu Leu Tyr
                165                 170                 175

Ser Gly Asn Gln Lys Asn Tyr Leu Ala Trp Tyr Gln Gln Lys Pro Gly
            180                 185                 190

Gln Ser Pro Lys Leu Leu Ile Tyr Trp Ala Ser Thr Arg Glu Ser Gly
        195                 200                 205

Val Pro Asp Arg Phe Thr Gly Ser Gly Ser Gly Thr Asp Phe Thr Leu
    210                 215                 220
```

Ser Ile Ser Ser Val Glu Thr Glu Asp Leu Ala Val Tyr Tyr Cys Gln
225                 230                 235                 240

Gln Tyr Tyr Ser Tyr Pro Leu Thr Phe Gly Ala Gly Thr Lys Leu Val
                245                 250                 255

Leu Lys Thr Pro Val Ser Glu Lys Gln Leu Ala Glu Val Val Ala Asn
            260                 265                 270

Thr Ile Thr Pro Leu Met Lys Ala Gln Ser Val Pro Gly Met Ala Val
        275                 280                 285

Ala Val Ile Tyr Gln Gly Lys Pro His Tyr Tyr Thr Phe Gly Lys Ala
    290                 295                 300

Asp Ile Ala Ala Asn Lys Pro Val Thr Pro Gln Thr Leu Phe Glu Leu
305                 310                 315                 320

Gly Ser Ile Ser Lys Thr Phe Thr Gly Val Leu Gly Gly Asp Ala Ile
                325                 330                 335

Ala Arg Gly Glu Ile Ser Leu Asp Asp Ala Val Thr Arg Tyr Trp Pro
            340                 345                 350

Gln Leu Thr Gly Lys Gln Trp Gln Gly Ile Arg Met Leu Asp Leu Ala
        355                 360                 365

Thr Tyr Thr Ala Gly Gly Leu Pro Leu Gln Val Pro Asp Glu Val Thr
    370                 375                 380

Asp Asn Ala Ser Leu Leu Arg Phe Tyr Gln Asn Trp Gln Pro Gln Trp
385                 390                 395                 400

Lys Pro Gly Thr Thr Arg Leu Tyr Ala Asn Ala Ser Ile Gly Leu Phe
                405                 410                 415

Gly Ala Leu Ala Val Lys Pro Ser Gly Met Pro Tyr Glu Gln Ala Met
            420                 425                 430

Thr Thr Arg Val Leu Lys Pro Leu Lys Leu Asp His Thr Trp Ile Asn
        435                 440                 445

Val Pro Lys Ala Glu Ala His Tyr Ala Trp Gly Tyr Arg Asp Gly
    450                 455                 460

Lys Ala Val Arg Val Ser Pro Gly Met Leu Asp Ala Gln Ala Tyr Gly
465                 470                 475                 480

Val Lys Thr Asn Val Gln Asp Met Ala Asn Trp Val Met Ala Asn Met
                485                 490                 495

Ala Pro Glu Asn Val Ala Asp Ala Ser Leu Lys Gln Gly Ile Ala Leu
            500                 505                 510

Ala Gln Ser Arg Tyr Trp Arg Ile Gly Ser Met Tyr Gln Gly Leu Gly
        515                 520                 525

Trp Glu Met Leu Asn Trp Pro Val Glu Ala Asn Thr Val Val Glu Thr
    530                 535                 540

Ser Phe Gly Asn Val Ala Leu Ala Pro Leu Pro Val Ala Glu Val Asn
545                 550                 555                 560

Pro Pro Ala Pro Pro Val Lys Ala Ser Trp Val His Lys Thr Gly Ser
                565                 570                 575

Thr Gly Gly Phe Gly Ser Tyr Val Ala Phe Ile Pro Glu Lys Gln Ile
            580                 585                 590

Gly Ile Val Met Leu Ala Asn Thr Ser Tyr Pro Asn Pro Ala Arg Val
        595                 600                 605

Glu Ala Ala Tyr His Ile Leu Glu Ala Leu Gln
    610                 615

<210> SEQ ID NO 11
<211> LENGTH: 1575
<212> TYPE: DNA

<213> ORGANISM: Artificial Sequence
<220> FEATURE:
<223> OTHER INFORMATION: synthetic sequence encoding Tab 2.6 protein

<400> SEQUENCE: 11

```
caggtgcagt tacagcagtc agatgcggag ttggtgaaac cgggcgcgag cgtaaagatt     60
tcttgtaaag catccggcta cacctttacc gaccatgcca ttcactgggt aaaacagaac    120
ccggaacagg gcctggagtg gattgggtat ttcagcccgg taatgatga ctttaagtat    180
aacgaacgct ttaaaggtaa agccaccctg acggcggaca atcgtcgtc cactgcttac    240
ctgcagctga acagtctcac gtcagaagat agcgcggtgt atttctgtac gcgtagcctt    300
aacatggcgt attggggtca aggaccagc gtgaccgtta gcagcggtgg tggcggttcg    360
ggtggcggag gcagcggtgg aggggctct ggggcggcg gttccggtgg aggtggaagt    420
ggcggcggtg gatctgatat tgtcatgacc caatctccgt catcactgcc cgtgagtgtt    480
ggagaaaagg tgacgctgag ttgcaaaagc tcccaaagcc tgctatacag cggcaatcag    540
aagaattatc tggcatggta tcagcagaaa ccaggccagt ctcctaaatt gctgatctat    600
tgggcctcta cccgtgaatc cggtgttcca gatcgtttca ccggcagtgg ttcgggcact    660
gattttacac tgtccatttc gtctgtggaa acagaagacc tggctgtcta ctattgccaa    720
caatactact catatccgct taccctttggg gcgggtacta aattagttct caaaacaccg    780
gtgcacccag aaacgctggt gaaagtaaaa gatgctgaag atcagttggg tgcacgagtg    840
ggttacatcg aactggatct caacagcggt aagatccttg agagttttcg ccccgaagaa    900
cgtttcccaa tgatgagcac tttaaagtt ctgctatgtg gcgcggtatt atcccgtgtt    960
gacgccgggc aagagcaact cggtcgccgc atacactatt ctcagaatga cttggttaag   1020
tactcaccag tcacagaaaa agcatcttacg gatggcatga cagtaagaga attatgcagt   1080
gctgccataa ccatgagtga taacactgcg gccaacttac ttctgacaac gatcggagga   1140
ccgaaggagc taaccgcttt tttgcacaac atgggggatc atgtaactcg ccttgatcgt   1200
tgggaaccgg agctgaatga agccataca aacgacgagc gtgacaccac gatgcctgta   1260
gcaatggcaa caacgttgcg caaactatta actggcgaac tacttactct agcttcccgg   1320
caacaattaa tagactggat ggaggcggat aaagttgcag gaccacttct gcgctcggcc   1380
cttccggctg ctggtttat tgctgataaa tctggagccg tgagcgtgg gtctcgcggt   1440
atcattgcag cactggggcc agatggtaag ccctcccgta tcgtagttat ctacacgacg   1500
gggagtcagg caactatgga tgaacgaaat agacagatcg ctgagatagg tgcctcactg   1560
attaagcatt ggtaa                                                   1575
```

<210> SEQ ID NO 12
<211> LENGTH: 524
<212> TYPE: PRT
<213> ORGANISM: Artificial Sequence
<220> FEATURE:
<223> OTHER INFORMATION: synthetic Tab 2.6 protein

<400> SEQUENCE: 12

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
```

```
                    50                  55                  60
Lys Gly Lys Ala Thr Leu Thr Ala Asp Lys Ser Ser Thr Ala Tyr
 65                  70                  75                  80

Leu Gln Leu Asn Ser Leu Thr Ser Glu Asp Ser Ala Val Tyr Phe Cys
                     85                  90                  95

Thr Arg Ser Leu Asn Met Ala Tyr Trp Gly Gln Gly Thr Ser Val Thr
                    100                 105                 110

Val Ser Ser Gly Gly Gly Gly Ser Gly Gly Gly Gly Ser Gly Gly Gly
                115                 120                 125

Gly Ser Gly Gly Gly Gly Ser Gly Gly Gly Gly Ser Gly Gly Gly Gly
            130                 135                 140

Ser Asp Ile Val Met Thr Gln Ser Pro Ser Ser Leu Pro Val Ser Val
145                 150                 155                 160

Gly Glu Lys Val Thr Leu Ser Cys Lys Ser Ser Gln Ser Leu Leu Tyr
                    165                 170                 175

Ser Gly Asn Gln Lys Asn Tyr Leu Ala Trp Tyr Gln Gln Lys Pro Gly
                180                 185                 190

Gln Ser Pro Lys Leu Leu Ile Tyr Trp Ala Ser Thr Arg Glu Ser Gly
                195                 200                 205

Val Pro Asp Arg Phe Thr Gly Ser Gly Ser Gly Thr Asp Phe Thr Leu
210                 215                 220

Ser Ile Ser Ser Val Glu Thr Glu Asp Leu Ala Val Tyr Tyr Cys Gln
225                 230                 235                 240

Gln Tyr Tyr Ser Tyr Pro Leu Thr Phe Gly Ala Gly Thr Lys Leu Val
                    245                 250                 255

Leu Lys Thr Pro Val His Pro Glu Thr Leu Val Lys Val Lys Asp Ala
                260                 265                 270

Glu Asp Gln Leu Gly Ala Arg Val Gly Tyr Ile Glu Leu Asp Leu Asn
                275                 280                 285

Ser Gly Lys Ile Leu Glu Ser Phe Arg Pro Glu Glu Arg Phe Pro Met
290                 295                 300

Met Ser Thr Phe Lys Val Leu Leu Cys Gly Ala Val Leu Ser Arg Val
305                 310                 315                 320

Asp Ala Gly Gln Glu Gln Leu Gly Arg Arg Ile His Tyr Ser Gln Asn
                    325                 330                 335

Asp Leu Val Lys Tyr Ser Pro Val Thr Glu Lys His Leu Thr Asp Gly
                340                 345                 350

Met Thr Val Arg Glu Leu Cys Ser Ala Ala Ile Thr Met Ser Asp Asn
                355                 360                 365

Thr Ala Ala Asn Leu Leu Leu Thr Thr Ile Gly Gly Pro Lys Glu Leu
370                 375                 380

Thr Ala Phe Leu His Asn Met Gly Asp His Val Thr Arg Leu Asp Arg
385                 390                 395                 400

Trp Glu Pro Glu Leu Asn Glu Ala Ile Pro Asn Asp Glu Arg Asp Thr
                    405                 410                 415

Thr Met Pro Val Ala Met Ala Thr Thr Leu Arg Lys Leu Leu Thr Gly
                420                 425                 430

Glu Leu Leu Thr Leu Ala Ser Arg Gln Gln Leu Ile Asp Trp Met Glu
                435                 440                 445

Ala Asp Lys Val Ala Gly Pro Leu Leu Arg Ser Ala Leu Pro Ala Gly
                450                 455                 460

Trp Phe Ile Ala Asp Lys Ser Gly Ala Gly Glu Arg Gly Ser Arg Gly
465                 470                 475                 480
```

```
Ile Ile Ala Ala Leu Gly Pro Asp Gly Lys Pro Ser Arg Ile Val Val
            485                 490                 495
Ile Tyr Thr Thr Gly Ser Gln Ala Thr Met Asp Glu Arg Asn Arg Gln
        500                 505                 510
Ile Ala Glu Ile Gly Ala Ser Leu Ile Lys His Trp
        515                 520

<210> SEQ ID NO 13
<211> LENGTH: 1860
<212> TYPE: DNA
<213> ORGANISM: Artificial Sequence
<220> FEATURE:
<223> OTHER INFORMATION: synthetic sequence encoding Tab 2.7 protein

<400> SEQUENCE: 13
caggtgcagt tacagcagtc agatgcggag ttggtgaaaac cgggcgcgag cgtaaagatt    60
tcttgtaaag catccggcta caccttttacc gaccatgcca ttcactgggt aaaacagaac   120
ccggaacagg gcctggagtg gattgggtat ttcagcccgg taatgatga ctttaagtat    180 aacgaacgct ttaaaggtaa agccacctg acggcggaca atcgtcgtc cactgcttac    240 ctgcagctga cagtctcac gtcagaagat agcgcggtgt atttctgtac gcgtagcctt    300
aacatggcgt attggggtca agggaccagc gtgaccgtta gcagcggtgg tggcggttcg    360
ggtggcggag gcagcggtgg aggggggctct ggggcggcg ttccggtgg aggtggaagt    420 ggcggcggtg gatctgatat tgtcatgacc caatctccgt catcactgcc cgtgagtgtt    480
ggagaaaagg tgacgctgag ttgcaaaagc tcccaaagcc tgctatacag cggcaatcag    540
aagaattatc tggcatggta tcagcagaaa ccaggccagt ctcctaaatt gctgatctat    600
tgggcctcta cccgtgaatc cggtgttcca gatcgttttca ccggcagtgg ttcgggcact    660 gatttttacac tgtccatttc gtctgtggaa acagaagacc tggctgtcta ctattgccaa    720
caatactact catatccgct tacctttggg gcgggtacta aattagttct caaaacaccg    780
gtgtcagaaa acagctggc ggaggtggtc gcgaatacga ttaccccgct gatgaaagca    840
cagagtattc caggcatggc ggtggccgtt atttatcagg gaaaaccgca ctattacaca    900
tttggcaagg ccgatatcgc ggcgaataaa cccgttacgc ctcagaccct gttcgagctg    960
ggttctataa gtaaaacctt caccggcgtt ttaggtgggg atgccattgc tcgcggtgaa   1020
atttcgctgg acgatgcggt gaccaaatac tggccagagc tgacgggcaa gcagtggcag   1080
ggtattcgta tgctggatct cgccacctac accgctggcg gcctgccgct acaggtaccg   1140
gatgaggtca cggataacgc ctccctgctg cgcttttatc aaaactggca gccgcagtgg   1200
aagcctggca acgcgtctc ttacgccaac tccagcatcg gtctttttgg tgcgctggcg   1260
gtcaaaccct tctggcatgcc ctatgagcag gccatgacga cgcgggtcct taagccgctc   1320
aagctggacc ataccctggat taacgtgccg aaagcggaag aggcgcatta cgcctggggc   1380
tatcgtgacg gtaaagcggt gcgcgttcg ccgggtatgc tggatgcaca agcctatggc   1440
gtgaaaacca acgtgcagga tatgcgcgc tgggtcatgg ccaacatggc cccggagaac   1500
gttgctgatg cctcacttaa gcagggcatc gcgctggcg agtcgcgcta ctggcgtgtc   1560
gggtcaatgt atcagggtct cggctgggag atgctcaact ggcccgtgga ggcaaacacg   1620
gtgatcgagg caagcgacag taaggtagcg ctagcgccgt tgcccgtggc agaagtgaat   1680
ccaccggctc ccccggtcaa agcgtcctgg gtccataaaa ctggctctac tggcgggttt   1740
ggatcctacg tggcctttat tcctgaaaag cagctcggta ttgtgatgct cgcgaatacaa   1800 agctatccga acccggctcg agttgaggcg gcataccata tcctagaggc gctacagtaa   1860
```

<210> SEQ ID NO 14
<211> LENGTH: 619
<212> TYPE: PRT
<213> ORGANISM: Artificial Sequence
<220> FEATURE:
<223> OTHER INFORMATION: synthetic Tab 2.7 protein

<400> SEQUENCE: 14

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Asp Ile Val Met Thr Gln Ser Pro Ser Ser Leu Pro Val Ser Val
145                 150                 155                 160

Gly Glu Lys Val Thr Leu Ser Cys Lys Ser Ser Gln Ser Leu Leu Tyr
                165                 170                 175

Ser Gly Asn Gln Lys Asn Tyr Leu Ala Trp Tyr Gln Gln Lys Pro Gly
            180                 185                 190

Gln Ser Pro Lys Leu Leu Ile Tyr Trp Ala Ser Thr Arg Glu Ser Gly
        195                 200                 205

Val Pro Asp Arg Phe Thr Gly Ser Gly Ser Gly Thr Asp Phe Thr Leu
    210                 215                 220

Ser Ile Ser Ser Val Glu Thr Glu Asp Leu Ala Val Tyr Tyr Cys Gln
225                 230                 235                 240

Gln Tyr Tyr Ser Tyr Pro Leu Thr Phe Gly Ala Gly Thr Lys Leu Val
                245                 250                 255

Leu Lys Thr Pro Val Ser Glu Lys Gln Leu Ala Glu Val Val Ala Asn
            260                 265                 270

Thr Ile Thr Pro Leu Met Lys Ala Gln Ser Ile Pro Gly Met Ala Val
        275                 280                 285

Ala Val Ile Tyr Gln Gly Lys Pro His Tyr Tyr Thr Phe Gly Lys Ala
    290                 295                 300

Asp Ile Ala Ala Asn Lys Pro Val Thr Pro Gln Thr Leu Phe Glu Leu
305                 310                 315                 320

Gly Ser Ile Ser Lys Thr Phe Thr Gly Val Leu Gly Gly Asp Ala Ile
                325                 330                 335

Ala Arg Gly Glu Ile Ser Leu Asp Asp Ala Val Thr Lys Tyr Trp Pro
            340                 345                 350

Glu Leu Thr Gly Lys Gln Trp Gln Gly Ile Arg Met Leu Asp Leu Ala
        355                 360                 365
```

```
Thr Tyr Thr Ala Gly Gly Leu Pro Leu Gln Val Pro Asp Glu Val Thr
    370                 375                 380

Asp Asn Ala Ser Leu Leu Arg Phe Tyr Gln Asn Trp Gln Pro Gln Trp
385                 390                 395                 400

Lys Pro Gly Thr Thr Arg Leu Tyr Ala Asn Ser Ser Ile Gly Leu Phe
                405                 410                 415

Gly Ala Leu Ala Val Lys Pro Ser Gly Met Pro Tyr Glu Gln Ala Met
            420                 425                 430

Thr Thr Arg Val Leu Lys Pro Leu Lys Leu Asp His Thr Trp Ile Asn
        435                 440                 445

Val Pro Lys Ala Glu Glu Ala His Tyr Ala Trp Gly Tyr Arg Asp Gly
    450                 455                 460

Lys Ala Val Arg Val Ser Pro Gly Met Leu Asp Ala Gln Ala Tyr Gly
465                 470                 475                 480

Val Lys Thr Asn Val Gln Asp Met Ala Arg Trp Val Met Ala Asn Met
                485                 490                 495

Ala Pro Glu Asn Val Ala Asp Ala Ser Leu Lys Gln Gly Ile Ala Leu
            500                 505                 510

Ala Gln Ser Arg Tyr Trp Arg Val Gly Ser Met Tyr Gln Gly Leu Gly
        515                 520                 525

Trp Glu Met Leu Asn Trp Pro Val Glu Ala Asn Thr Val Ile Glu Gly
    530                 535                 540

Ser Asp Ser Lys Val Ala Leu Ala Pro Leu Pro Val Ala Glu Val Asn
545                 550                 555                 560

Pro Pro Ala Pro Pro Val Lys Ala Ser Trp Val His Lys Thr Gly Ser
                565                 570                 575

Thr Gly Gly Phe Gly Ser Tyr Val Ala Phe Ile Pro Glu Lys Gln Leu
            580                 585                 590

Gly Ile Val Met Leu Ala Asn Thr Ser Tyr Pro Asn Pro Ala Arg Val
        595                 600                 605

Glu Ala Ala Tyr His Ile Leu Glu Ala Leu Gln
    610                 615

<210> SEQ ID NO 15
<211> LENGTH: 1860
<212> TYPE: DNA
<213> ORGANISM: Artificial Sequence
<220> FEATURE:
<223> OTHER INFORMATION: synthetic sequence encoding pME403.3 protein

<400> SEQUENCE: 15
gatattgtca tgacgcaatc tccgagctcc ctgccagtta gcgtcggcga gaaagtgacg     60
ctgagctgta atccagcca atctctgctg tatagcggca atcagaagaa ctacctggcg    120
tggtaccagc agaaaccggg tcagtccccg aagctgctga tttattgggc ttctacccgc    180
gaaagcggtg tcccagaccg cttcacgggt agcggtagcg gcactgactt caccctgtcc    240
atttcttctg ttgaaacgga agatctggcg gtgtattact gccaacagta ttactcctat    300
ccactgactt tcggtgccgg cactaaactg gttctgaagg gtggcggcgg ttccggcggt    360
ggtggttccg gtggcggtgg ctctggcggc ggtggctccg gcggcggcgg ttctggcggt    420
ggcggatccc aggtgcagct gcaacaaagc gatgcagagc tggttaaacc tggtgcgagc    480
gttaaaatta gctgcaaggc gtccggttat acttttaccg atcacgccat tcactgggtc    540
aagcagaacc cggaacaagg cctggagtgg atcggctatt tctctccggg caacgatgac    600
ttcaaataca tgaacgcttt taaggcaaa gccactctga ccgctgataa atctagctcc    660
```

-continued

```
acggcctacc tgcaactgaa cagcctgacc tccgaagata gcgccgtgta tttctgcacc    720
cgcagcctga atatggcgta ctggggccag ggcacttccg tgacggtgag cagcacaccg    780
gtgtcagaaa aacagctggc ggaggtggtc gcgaatacga ttaccccgct gatgaaagcc    840
cagtctgttc caggcatggc ggtggccgtt atttatcagg aaaaccgca  ctattacaca    900
tttggcaagg ccgatatcgc ggcgaataaa cccgttacgc ctcagaccct gttcgagctg    960
ggttctataa gtaaaacctt caccggcgtt ttaggtgggg atgccattgc tcgcggtgaa   1020
atttcgctgg acgatgcggt gaccagatac tggccacagc tgacgggcaa gcagtggcag   1080
ggtattcgta tgctggatct cgccacctac accgctggcg gcctgccgct acaggtaccg   1140
gatgaggtca cggataacgc ctccctgctg cgcttttatc aaaactggca gccgcagtgg   1200
aagcctggca aacgcgtct  ttacgccaac gccagcatcg gtcttttgg  tgcgctggcg   1260
gtcaaacctt ctggcatgcc ctatgagcag gccatgacga cgcgggtcct taagccgctc   1320
aagctggacc atacctggat taacgtgccg aaagcggaag aggcgcatta cgcctggggc   1380
tatcgtgacg gtaaagcggt gcgcgtttcg ccgggtatgc tggatgcaca agcctatggc   1440
gtgaaaacca acgtgcagga tatggcgaac tgggtcatgg caaacatggc gccggagaac   1500
gttgctgatg cctcacttaa gcagggcatc gcgctggcgc agtcgcgcta ctggcgtatc   1560
gggtcaatgt atcagggtct gggctgggag atgctcaact ggcccgtgga ggccaacacg   1620
gtggtcgaga cgagttttgg taatgtagca ctggcgccgt tgcccgtggc agaagtgaat   1680
ccaccggctc ccccggtcaa agcgtcctgg gtccataaaa cgggctctac tggcgggttt   1740
ggcagctacg tggcctttat tcctgaaaag cagatcggta ttgtgatgct cgcgaataca   1800
agctatccga acccggcacg cgttgaggcg cataccata  tcctcgaggc gctacagtag   1860
```

<210> SEQ ID NO 16
<211> LENGTH: 619
<212> TYPE: PRT
<213> ORGANISM: Artificial Sequence
<220> FEATURE:
<223> OTHER INFORMATION: synthetic Tab 2.8 protein

<400> SEQUENCE: 16

```
Asp Ile Val Met Thr Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Glu Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys Gly Gly Gly Gly Ser Gly Gly Gly Gly Ser Gly Gly Gly Gly Ser
        115                 120                 125

Gly Gly Gly Gly Ser Gly Gly Gly Ser Gly Gly Gly Gly Ser Gln
    130                 135                 140

Val Gln Leu Gln Gln Ser Asp Ala Glu Leu Val Lys Pro Gly Ala Ser
145                 150                 155                 160
```

-continued

```
Val Lys Ile Ser Cys Lys Ala Ser Gly Tyr Thr Phe Thr Asp His Ala
                165                 170                 175
Ile His Trp Val Lys Gln Asn Pro Glu Gln Gly Leu Glu Trp Ile Gly
            180                 185                 190
Tyr Phe Ser Pro Gly Asn Asp Asp Phe Lys Tyr Asn Glu Arg Phe Lys
        195                 200                 205
Gly Lys Ala Thr Leu Thr Ala Asp Lys Ser Ser Thr Ala Tyr Leu
    210                 215                 220
Gln Leu Asn Ser Leu Thr Ser Glu Asp Ser Ala Val Tyr Phe Cys Thr
225                 230                 235                 240
Arg Ser Leu Asn Met Ala Tyr Trp Gly Gln Gly Thr Ser Val Thr Val
                245                 250                 255
Ser Ser Thr Pro Val Ser Glu Lys Gln Leu Ala Glu Val Ala Asn
            260                 265                 270
Thr Ile Thr Pro Leu Met Lys Ala Gln Ser Val Pro Gly Met Ala Val
        275                 280                 285
Ala Val Ile Tyr Gln Gly Lys Pro His Tyr Tyr Thr Phe Gly Lys Ala
    290                 295                 300
Asp Ile Ala Ala Asn Lys Pro Val Thr Pro Gln Thr Leu Phe Glu Leu
305                 310                 315                 320
Gly Ser Ile Ser Lys Thr Phe Thr Gly Val Leu Gly Gly Asp Ala Ile
                325                 330                 335
Ala Arg Gly Glu Ile Ser Leu Asp Asp Ala Val Thr Arg Tyr Trp Pro
            340                 345                 350
Gln Leu Thr Gly Lys Gln Trp Gln Gly Ile Arg Met Leu Asp Leu Ala
        355                 360                 365
Thr Tyr Thr Ala Gly Gly Leu Pro Leu Gln Val Pro Asp Glu Val Thr
    370                 375                 380
Asp Asn Ala Ser Leu Leu Arg Phe Tyr Gln Asn Trp Gln Pro Gln Trp
385                 390                 395                 400
Lys Pro Gly Thr Thr Arg Leu Tyr Ala Asn Ala Ser Ile Gly Leu Phe
                405                 410                 415
Gly Ala Leu Ala Val Lys Pro Ser Gly Met Pro Tyr Glu Gln Ala Met
            420                 425                 430
Thr Thr Arg Val Leu Lys Pro Leu Lys Leu Asp His Thr Trp Ile Asn
        435                 440                 445
Val Pro Lys Ala Glu Glu Ala His Tyr Ala Trp Gly Tyr Arg Asp Gly
    450                 455                 460
Lys Ala Val Arg Val Ser Pro Gly Met Leu Asp Ala Gln Ala Tyr Gly
465                 470                 475                 480
Val Lys Thr Asn Val Gln Asp Met Ala Asn Trp Val Met Ala Asn Met
                485                 490                 495
Ala Pro Glu Asn Val Ala Asp Ala Ser Leu Lys Gln Gly Ile Ala Leu
            500                 505                 510
Ala Gln Ser Arg Tyr Trp Arg Ile Gly Ser Met Tyr Gln Gly Leu Gly
        515                 520                 525
Trp Glu Met Leu Asn Trp Pro Val Glu Ala Asn Thr Val Val Glu Thr
    530                 535                 540
Ser Phe Gly Asn Val Ala Leu Ala Pro Leu Pro Val Ala Glu Val Asn
545                 550                 555                 560
Pro Pro Ala Pro Pro Val Lys Ala Ser Trp Val His Lys Thr Gly Ser
                565                 570                 575
Thr Gly Gly Phe Gly Ser Tyr Val Ala Phe Ile Pro Glu Lys Gln Ile
            580                 585                 590
```

```
Gly Ile Val Met Leu Ala Asn Thr Ser Tyr Pro Asn Pro Ala Arg Val
    595                 600                 605

Glu Ala Ala Tyr His Ile Leu Glu Ala Leu Gln
    610                 615

<210> SEQ ID NO 17
<211> LENGTH: 1860
<212> TYPE: DNA
<213> ORGANISM: Artificial Sequence
<220> FEATURE:
<223> OTHER INFORMATION: synthetic sequence encoding pME403.3 protein

<400> SEQUENCE: 17
caggtgcagt tacagcagtc agatgcggag ttggtgaaac cgggcgcgag cgtaaagatt    60
tcttgtaaag catccggcta caccttttacc gaccatgcca ttcactgggt aaaacagaac   120
ccggaacagg gcctggagtg gattgggtat ttcagcccgg gtaatgatga ctttaagtat   180
aacgaacgct ttaaaggtaa agccacccctg acggcggaca aatcgtcgtc cactgcttac   240
ctgcagctga cagtctcac gtcagaagat agcgcggtgt atttctgtac gcgtagcctt    300
aacatgtgct attgggtca agggaccagc gtgaccgtta gcagcggtgg tggcggttcg   360
ggtggcggag gcagcggtgg agggggctct ggggcggcg gttccggtgg aggtggaagt   420
ggcggcggtg gatctgatat tgtcatgacc caatctccgt catcactgcc cgtgagtgtt   480
ggagaaaagg tgacgctgag ttgcaaaagc tcccaaagcc tgctatacag cggcaatcag   540
aagaattatc tggcatggta tcagcagaaa ccaggccagt ctcctaaatg cctgatctat   600
tgggcctcta cccgtgaatc cggtgttcca gatcgtttca ccggcagtgg ttcgggcact   660
gattttacac tgtccatttc gtctgtggaa acagaagacc tggctgtcta ctattgccaa   720
caatactact catatccgct taccttttggg gcgggtacta aattagttct caaaacaccg   780
gtgtcagaaa aacagctggc ggaggtggtc gcgaatacga ttaccccgct gatgaaagca   840
cagagtattc caggcatggc ggtggccgtt atttatcagg aaaaccgca ctattacaca   900 tttggcaagg ccgatatcgc ggcgaataaa cccgttacgc ctcagaccct gttcgagctg   960
ggttctataa gtaaaacctt caccggcgtt ttaggtgggg atgccattgc tcgcggtgaa  1020
atttcgctgg acgatgcggt gaccaaatac tggccagagc tgacgggcaa gcagtggcag  1080
ggtattcgta tgctggatct cgccacctac accgctggcg gcctgccgct acaggtaccg  1140
gatgaggtca cggataacgc ctcctctgctg cgctttatc aaaactggca gccgcagtgg  1200
aagcctggca caacgcgtct ttacgccaac tccagcatcg gtctttttgg tgcgctggcg  1260
gtcaaacctt ctggcatgcc ctatgagcag gccatgacga cgcgggtcct taagccgctc  1320
aagctggacc ataccttggat taacgtgccg aaagcggaag aggcgcatta cgcctggggc  1380
tatcgtgacg gtaaagcggt gcgcgtttcg ccgggtatgc tggatgcaca agcctatggc  1440
gtgaaaacca acgtgcagga tatggcgcgc tgggtcatgg ccaacatggc cccggagaac  1500
gttgctgatg cctcacttaa gcagggcatc gcgctggcgc agtcgcgcta ctggcgtgtc  1560
gggtcaatgt atcagggtct cggctgggag atgctcaact ggcccgtgga ggcaaacacg  1620
gtgatcgagg gcagcgacag taaggtagcg ctagcgccgt tgcccgtggc agaagtgaat  1680
ccaccggctc cccggtcaa agcgtcctgg gtccataaaa ctggctctac tggcgggttt  1740
ggatcctacg tggcctttat tcctgaaaag cagctcggta ttgtgatgct cgcgaataca  1800
agctatccga acccggctcg agttgaggcg gcataccata tcctagaggc gctacagtaa  1860
```

-continued

```
<210> SEQ ID NO 18
<211> LENGTH: 619
<212> TYPE: PRT
<213> ORGANISM: Artificial Sequence
<220> FEATURE:
<223> OTHER INFORMATION: synthetic pME403.3 protein

<400> SEQUENCE: 18
```

| Gln | Val | Gln | Leu | Gln | Gln | Ser | Asp | Ala | Glu | Leu | Val | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Ile | Ser | Cys | Lys | Ala | Ser | Gly | Tyr | Thr | Phe | Thr | Asp | His |
|---|---|---|---|---|---|---|---|---|---|---|---|---|---|---|---|
| | | | 20 | | | | | 25 | | | | | 30 | | |

| Ala | Ile | His | Trp | Val | Lys | Gln | Asn | Pro | Glu | Gln | Gly | Leu | Glu | Trp | Ile |
|---|---|---|---|---|---|---|---|---|---|---|---|---|---|---|---|
| | | 35 | | | | | 40 | | | | | 45 | | | |

| Gly | Tyr | Phe | Ser | Pro | Gly | Asn | Asp | Asp | Phe | Lys | Tyr | Asn | Glu | Arg | Phe |
|---|---|---|---|---|---|---|---|---|---|---|---|---|---|---|---|
| | 50 | | | | | 55 | | | | | 60 | | | | |

| Lys | Gly | Lys | Ala | Thr | Leu | Thr | Ala | Asp | Lys | Ser | Ser | Thr | Ala | Tyr |
|---|---|---|---|---|---|---|---|---|---|---|---|---|---|---|
| 65 | | | | | 70 | | | | | 75 | | | | 80 |

| Leu | Gln | Leu | Asn | Ser | Leu | Thr | Ser | Glu | Asp | Ser | Ala | Val | Tyr | Phe | Cys |
|---|---|---|---|---|---|---|---|---|---|---|---|---|---|---|---|
| | | | | 85 | | | | | 90 | | | | | 95 | |

| Thr | Arg | Ser | Leu | Asn | Met | Cys | Tyr | Trp | Gly | Gln | Gly | Thr | Ser | Val | Thr |
|---|---|---|---|---|---|---|---|---|---|---|---|---|---|---|---|
| | | | 100 | | | | | 105 | | | | | 110 | | |

| Val | Ser | Ser | Gly | Gly | Gly | Gly | Ser | Gly | Gly | Gly | Ser | Gly | Gly | Gly |
|---|---|---|---|---|---|---|---|---|---|---|---|---|---|---|
| | | 115 | | | | | 120 | | | | | 125 | | |

| Gly | Ser | Gly | Gly | Gly | Gly | Ser | Gly | Gly | Gly | Ser | Gly | Gly | Gly | Gly |
|---|---|---|---|---|---|---|---|---|---|---|---|---|---|---|
| | 130 | | | | | 135 | | | | | 140 | | | |

| Ser | Asp | Ile | Val | Met | Thr | Gln | Ser | Pro | Ser | Ser | Leu | Pro | Val | Ser | Val |
|---|---|---|---|---|---|---|---|---|---|---|---|---|---|---|---|
| 145 | | | | | 150 | | | | | 155 | | | | | 160 |

| Gly | Glu | Lys | Val | Thr | Leu | Ser | Cys | Lys | Ser | Ser | Gln | Ser | Leu | Leu | Tyr |
|---|---|---|---|---|---|---|---|---|---|---|---|---|---|---|---|
| | | | | 165 | | | | | 170 | | | | | 175 | |

| Ser | Gly | Asn | Gln | Lys | Asn | Tyr | Leu | Ala | Trp | Tyr | Gln | Gln | Lys | Pro | Gly |
|---|---|---|---|---|---|---|---|---|---|---|---|---|---|---|---|
| | | | 180 | | | | | 185 | | | | | 190 | | |

| Gln | Ser | Pro | Lys | Cys | Leu | Ile | Tyr | Trp | Ala | Ser | Thr | Arg | Glu | Ser | Gly |
|---|---|---|---|---|---|---|---|---|---|---|---|---|---|---|---|
| | | 195 | | | | | 200 | | | | | 205 | | | |

| Val | Pro | Asp | Arg | Phe | Thr | Gly | Ser | Gly | Ser | Gly | Thr | Asp | Phe | Thr | Leu |
|---|---|---|---|---|---|---|---|---|---|---|---|---|---|---|---|
| | 210 | | | | | 215 | | | | | 220 | | | | |

| Ser | Ile | Ser | Ser | Val | Glu | Thr | Glu | Asp | Leu | Ala | Val | Tyr | Tyr | Cys | Gln |
|---|---|---|---|---|---|---|---|---|---|---|---|---|---|---|---|
| 225 | | | | | 230 | | | | | 235 | | | | | 240 |

| Gln | Tyr | Tyr | Ser | Tyr | Pro | Leu | Thr | Phe | Gly | Ala | Gly | Thr | Lys | Leu | Val |
|---|---|---|---|---|---|---|---|---|---|---|---|---|---|---|---|
| | | | 245 | | | | | 250 | | | | | 255 | | |

| Leu | Lys | Thr | Pro | Val | Ser | Glu | Lys | Gln | Leu | Ala | Glu | Val | Val | Ala | Asn |
|---|---|---|---|---|---|---|---|---|---|---|---|---|---|---|---|
| | | | 260 | | | | | 265 | | | | | 270 | | |

| Thr | Ile | Thr | Pro | Leu | Met | Lys | Ala | Gln | Ser | Ile | Pro | Gly | Met | Ala | Val |
|---|---|---|---|---|---|---|---|---|---|---|---|---|---|---|---|
| | | 275 | | | | | 280 | | | | | 285 | | | |

| Ala | Val | Ile | Tyr | Gln | Gly | Lys | Pro | His | Tyr | Tyr | Thr | Phe | Gly | Lys | Ala |
|---|---|---|---|---|---|---|---|---|---|---|---|---|---|---|---|
| | 290 | | | | | 295 | | | | | 300 | | | | |

| Asp | Ile | Ala | Ala | Asn | Lys | Pro | Val | Thr | Pro | Gln | Thr | Leu | Phe | Glu | Leu |
|---|---|---|---|---|---|---|---|---|---|---|---|---|---|---|---|
| 305 | | | | | 310 | | | | | 315 | | | | | 320 |

| Gly | Ser | Ile | Ser | Lys | Thr | Phe | Thr | Gly | Val | Leu | Gly | Gly | Asp | Ala | Ile |
|---|---|---|---|---|---|---|---|---|---|---|---|---|---|---|---|
| | | | | 325 | | | | | 330 | | | | | 335 | |

| Ala | Arg | Gly | Glu | Ile | Ser | Leu | Asp | Asp | Ala | Val | Thr | Lys | Tyr | Trp | Pro |
|---|---|---|---|---|---|---|---|---|---|---|---|---|---|---|---|
| | | | 340 | | | | | 345 | | | | | 350 | | |

| Glu | Leu | Thr | Gly | Lys | Gln | Trp | Gln | Gly | Ile | Arg | Met | Leu | Asp | Leu | Ala |
|---|---|---|---|---|---|---|---|---|---|---|---|---|---|---|---|
| | | | 355 | | | | | 360 | | | | | 365 | | |

| Thr | Tyr | Thr | Ala | Gly | Gly | Leu | Pro | Leu | Gln | Val | Pro | Asp | Glu | Val | Thr |
|---|---|---|---|---|---|---|---|---|---|---|---|---|---|---|---|
| | 370 | | | | | 375 | | | | | 380 | | | | |

```
Asp Asn Ala Ser Leu Leu Arg Phe Tyr Gln Asn Trp Gln Pro Gln Trp
385                 390                 395                 400

Lys Pro Gly Thr Thr Arg Leu Tyr Ala Asn Ser Ser Ile Gly Leu Phe
            405                 410                 415

Gly Ala Leu Ala Val Lys Pro Ser Gly Met Pro Tyr Glu Gln Ala Met
                420                 425                 430

Thr Thr Arg Val Leu Lys Pro Leu Lys Leu Asp His Thr Trp Ile Asn
            435                 440                 445

Val Pro Lys Ala Glu Glu Ala His Tyr Ala Trp Gly Tyr Arg Asp Gly
        450                 455                 460

Lys Ala Val Arg Val Ser Pro Gly Met Leu Asp Ala Gln Ala Tyr Gly
465                 470                 475                 480

Val Lys Thr Asn Val Gln Asp Met Ala Arg Trp Val Met Ala Asn Met
                485                 490                 495

Ala Pro Glu Asn Val Ala Asp Ala Ser Leu Lys Gln Gly Ile Ala Leu
                500                 505                 510

Ala Gln Ser Arg Tyr Trp Arg Val Gly Ser Met Tyr Gln Gly Leu Gly
            515                 520                 525

Trp Glu Met Leu Asn Trp Pro Val Glu Ala Asn Thr Val Ile Glu Gly
        530                 535                 540

Ser Asp Ser Lys Val Ala Leu Ala Pro Leu Pro Val Ala Glu Val Asn
545                 550                 555                 560

Pro Pro Ala Pro Pro Val Lys Ala Ser Trp Val His Lys Thr Gly Ser
                565                 570                 575

Thr Gly Gly Phe Gly Ser Tyr Val Ala Phe Ile Pro Glu Lys Gln Leu
            580                 585                 590

Gly Ile Val Met Leu Ala Asn Thr Ser Tyr Pro Asn Pro Ala Arg Val
            595                 600                 605

Glu Ala Ala Tyr His Ile Leu Glu Ala Leu Gln
        610                 615

<210> SEQ ID NO 19

<400> SEQUENCE: 19

000

<210> SEQ ID NO 20
<211> LENGTH: 619
<212> TYPE: PRT
<213> ORGANISM: Artificial Sequence
<220> FEATURE:
<223> OTHER INFORMATION: synthetic Tab 2.5 fusion protein

<400> SEQUENCE: 20

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Lys Gln Asn Pro Glu Gln Gly Leu Glu Trp Ile
            35                  40                  45

Gly Tyr Phe Ser Pro Gly Asn Asp Asp Phe Lys Tyr Asn Glu Arg Phe
        50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95
```

-continued

```
Thr Arg Ser Leu Asn Met Ala Tyr Trp Gly Gln Gly Thr Ser Val Thr
            100                 105                 110
Val Ser Ser Gly Gly Gly Gly Ser Gly Gly Gly Gly Ser Gly Gly Gly
        115                 120                 125
Gly Ser Gly Gly Gly Gly Ser Gly Gly Gly Gly Ser Gly Gly Gly Gly
        130                 135                 140
Ser Asp Ile Val Met Thr Gln Ser Pro Ser Ser Leu Pro Val Ser Val
145                 150                 155                 160
Gly Glu Lys Val Thr Leu Ser Cys Lys Ser Ser Gln Ser Leu Leu Tyr
                165                 170                 175
Ser Gly Asn Gln Lys Asn Tyr Leu Ala Trp Tyr Gln Lys Pro Gly
            180                 185                 190
Gln Ser Pro Lys Leu Leu Ile Tyr Trp Ala Ser Thr Arg Glu Ser Gly
        195                 200                 205
Val Pro Asp Arg Phe Thr Gly Ser Gly Ser Gly Thr Asp Phe Thr Leu
    210                 215                 220
Ser Ile Ser Ser Val Glu Thr Glu Asp Leu Ala Val Tyr Tyr Cys Gln
225                 230                 235                 240
Gln Tyr Tyr Ser Tyr Pro Leu Thr Phe Gly Ala Gly Thr Lys Leu Val
                245                 250                 255
Leu Lys Thr Pro Val Ser Glu Lys Gln Leu Ala Glu Val Val Ala Asn
            260                 265                 270
Thr Ile Thr Pro Leu Met Lys Ala Gln Ser Val Pro Gly Met Ala Val
        275                 280                 285
Ala Val Ile Tyr Gln Gly Lys Pro His Tyr Tyr Thr Phe Gly Lys Ala
    290                 295                 300
Asp Ile Ala Ala Asn Lys Pro Val Thr Pro Gln Thr Leu Phe Glu Leu
305                 310                 315                 320
Gly Ser Ile Ser Lys Thr Phe Thr Gly Val Leu Gly Gly Asp Ala Ile
                325                 330                 335
Ala Arg Gly Glu Ile Ser Leu Asp Asp Ala Val Thr Arg Tyr Trp Pro
            340                 345                 350
Gln Leu Thr Gly Lys Gln Trp Gln Gly Ile Arg Met Leu Asp Leu Ala
        355                 360                 365
Thr Tyr Thr Ala Gly Gly Leu Pro Leu Gln Val Pro Asp Glu Val Thr
    370                 375                 380
Asp Asn Ala Ser Leu Leu Arg Phe Tyr Gln Asn Trp Gln Pro Gln Trp
385                 390                 395                 400
Lys Pro Gly Thr Thr Arg Leu Tyr Ala Asn Ala Ser Ile Gly Leu Phe
                405                 410                 415
Gly Ala Leu Ala Val Lys Pro Ser Gly Met Pro Tyr Glu Gln Ala Met
            420                 425                 430
Thr Thr Arg Val Leu Lys Pro Leu Lys Leu Asp His Thr Trp Ile Asn
        435                 440                 445
Val Pro Lys Ala Glu Glu Ala His Tyr Ala Trp Gly Tyr Arg Asp Gly
    450                 455                 460
Lys Ala Val Arg Val Ser Pro Gly Met Leu Asp Ala Gln Ala Tyr Gly
465                 470                 475                 480
Val Lys Thr Asn Val Gln Asp Met Ala Asn Trp Val Met Ala Asn Met
                485                 490                 495
Ala Pro Glu Asn Val Ala Asp Ala Ser Leu Lys Gln Gly Ile Ala Leu
            500                 505                 510
Ala Gln Ser Arg Tyr Trp Arg Ile Gly Ser Met Tyr Gln Gly Leu Gly
```

```
                515                 520                 525
Trp Glu Met Leu Asn Trp Pro Val Ala Asn Thr Val Val Glu Thr
    530                 535                 540

Ser Phe Gly Asn Val Ala Leu Ala Pro Leu Pro Val Ala Glu Val Asn
545                 550                 555                 560

Pro Pro Ala Pro Val Lys Ala Ser Trp Val His Lys Thr Gly Ser
                565                 570                 575

Thr Gly Gly Phe Gly Ser Tyr Val Ala Phe Ile Pro Glu Lys Gln Ile
                580                 585                 590

Gly Ile Val Met Leu Ala Asn Thr Ser Tyr Pro Asn Pro Ala Arg Val
            595                 600                 605

Glu Ala Ala Tyr His Ile Leu Glu Ala Leu Gln
        610                 615

<210> SEQ ID NO 21

<400> SEQUENCE: 21

000

<210> SEQ ID NO 22
<211> LENGTH: 619
<212> TYPE: PRT
<213> ORGANISM: Artificial Sequence
<220> FEATURE:
<223> OTHER INFORMATION: synthetic Tab 2.8 protein

<400> SEQUENCE: 22

Asp Ile Val Met Thr Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Glu Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys Gly Gly Gly Gly Ser Gly Gly Gly Gly Ser Gly Gly Gly Gly Ser
        115                 120                 125

Gly Gly Gly Gly Ser Gly Gly Gly Ser Gly Gly Gly Gly Ser Gln
    130                 135                 140

Val Gln Leu Gln Gln Ser Asp Ala Glu Leu Val Lys Pro Gly Ala Ser
145                 150                 155                 160

Val Lys Ile Ser Cys Lys Ala Ser Gly Tyr Thr Phe Thr Asp His Ala
                165                 170                 175

Ile His Trp Val Lys Gln Asn Pro Glu Gln Gly Leu Glu Trp Ile Gly
            180                 185                 190

Tyr Phe Ser Pro Gly Asn Asp Asp Phe Lys Tyr Asn Glu Arg Phe Lys
        195                 200                 205

Gly Lys Ala Thr Leu Thr Ala Asp Lys Ser Ser Thr Ala Tyr Leu
    210                 215                 220

Gln Leu Asn Ser Leu Thr Ser Glu Asp Ser Ala Val Tyr Phe Cys Thr
```

```
              225                 230                 235                 240

Arg Ser Leu Asn Met Ala Tyr Trp Gly Gln Gly Thr Ser Val Thr Val
                        245                 250                 255

Ser Ser Thr Pro Val Ser Glu Lys Gln Leu Ala Glu Val Val Ala Asn
                        260                 265                 270

Thr Ile Thr Pro Leu Met Lys Ala Gln Ser Val Pro Gly Met Ala Val
                    275                 280                 285

Ala Val Ile Tyr Gln Gly Lys Pro His Tyr Tyr Thr Phe Gly Lys Ala
                290                 295                 300

Asp Ile Ala Ala Asn Lys Pro Val Thr Pro Gln Thr Leu Phe Glu Leu
        305                 310                 315                 320

Gly Ser Ile Ser Lys Thr Phe Thr Gly Val Leu Gly Gly Asp Ala Ile
                        325                 330                 335

Ala Arg Gly Glu Ile Ser Leu Asp Asp Ala Val Thr Arg Tyr Trp Pro
                        340                 345                 350

Gln Leu Thr Gly Lys Gln Trp Gln Gly Ile Arg Met Leu Asp Leu Ala
                        355                 360                 365

Thr Tyr Thr Ala Gly Gly Leu Pro Leu Gln Val Pro Asp Glu Val Thr
                    370                 375                 380

Asp Asn Ala Ser Leu Leu Arg Phe Tyr Gln Asn Trp Gln Pro Gln Trp
        385                 390                 395                 400

Lys Pro Gly Thr Thr Arg Leu Tyr Ala Asn Ala Ser Ile Gly Leu Phe
                        405                 410                 415

Gly Ala Leu Ala Val Lys Pro Ser Gly Met Pro Tyr Glu Gln Ala Met
                        420                 425                 430

Thr Thr Arg Val Leu Lys Pro Leu Lys Leu Asp His Thr Trp Ile Asn
                        435                 440                 445

Val Pro Lys Ala Glu Ala His Tyr Ala Trp Gly Tyr Arg Asp Gly
                    450                 455                 460

Lys Ala Val Arg Val Ser Pro Gly Met Leu Asp Ala Gln Ala Tyr Gly
        465                 470                 475                 480

Val Lys Thr Asn Val Gln Asp Met Ala Asn Trp Val Met Ala Asn Met
                        485                 490                 495

Ala Pro Glu Asn Val Ala Asp Ala Ser Leu Lys Gln Gly Ile Ala Leu
                    500                 505                 510

Ala Gln Ser Arg Tyr Trp Arg Ile Gly Ser Met Tyr Gln Gly Leu Gly
                    515                 520                 525

Trp Glu Met Leu Asn Trp Pro Val Glu Ala Asn Thr Val Val Glu Thr
                530                 535                 540

Ser Phe Gly Asn Val Ala Leu Ala Pro Leu Pro Val Ala Glu Val Asn
        545                 550                 555                 560

Pro Pro Ala Pro Pro Val Lys Ala Ser Trp Val His Lys Thr Gly Ser
                        565                 570                 575

Thr Gly Gly Phe Gly Ser Tyr Val Ala Phe Ile Pro Glu Lys Gln Ile
                    580                 585                 590

Gly Ile Val Met Leu Ala Asn Thr Ser Tyr Pro Asn Pro Ala Arg Val
                    595                 600                 605

Glu Ala Ala Tyr His Ile Leu Glu Ala Leu Gln
            610                 615

<210> SEQ ID NO 23
<211> LENGTH: 30
<212> TYPE: PRT
<213> ORGANISM: Artificial Sequence
<220> FEATURE:
```

<223> OTHER INFORMATION: synthetic linker

<400> SEQUENCE: 23

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 24
<211> LENGTH: 15
<212> TYPE: PRT
<213> ORGANISM: Artificial Sequence
<220> FEATURE:
<223> OTHER INFORMATION: synthetic linker

<400> SEQUENCE: 24

Gly Gly Gly Gly Ser Gly Gly Gly Gly Ser Gly Gly Gly Gly Ser
1               5                   10                  15

<210> SEQ ID NO 25
<211> LENGTH: 90
<212> TYPE: DNA
<213> ORGANISM: Artificial Sequence
<220> FEATURE:
<223> OTHER INFORMATION: Synthetic primer

<400> SEQUENCE: 25
accgttagca gcggtggtgg cggttcgggt ggcggaggca gcggtggagg gggctctggg      60
ggcggcggtt ccggtggagg tggaagtggc                                      90

<210> SEQ ID NO 26
<211> LENGTH: 87
<212> TYPE: DNA
<213> ORGANISM: Artificial Sequence
<220> FEATURE:
<223> OTHER INFORMATION: Synthetic primer

<400> SEQUENCE: 26
accgccgccc ccagagcccc ctccaccgct gcctccgcca cccgaaccgc caccaccgct      60
gctaacggtc acgctggtcc cttgacc                                         87

<210> SEQ ID NO 27
<211> LENGTH: 37
<212> TYPE: DNA
<213> ORGANISM: Artificial Sequence
<220> FEATURE:
<223> OTHER INFORMATION: Synthetic primer

<400> SEQUENCE: 27
gttacagcag tcaggcgcgg agttggtgaa accgggc                              37

<210> SEQ ID NO 28
<211> LENGTH: 37
<212> TYPE: DNA
<213> ORGANISM: Artificial Sequence
<220> FEATURE:
<223> OTHER INFORMATION: Synthetic primer

<400> SEQUENCE: 28
cacctttacc gacatggcca ttcactgggt aaaacag                              37

<210> SEQ ID NO 29
<211> LENGTH: 37
<212> TYPE: DNA
<213> ORGANISM: Artificial Sequence

```
<220> FEATURE:
<223> OTHER INFORMATION: Synthetic primer

<400> SEQUENCE: 29
cacctttacc gacattgcca ttcactgggt aaaacag                              37

<210> SEQ ID NO 30
<211> LENGTH: 37
<212> TYPE: DNA
<213> ORGANISM: Artificial Sequence
<220> FEATURE:
<223> OTHER INFORMATION: Synthetic primer

<400> SEQUENCE: 30
ctttaccgac catggcattc actgggtaaa acagaac                              37

<210> SEQ ID NO 31
<211> LENGTH: 37
<212> TYPE: DNA
<213> ORGANISM: Artificial Sequence
<220> FEATURE:
<223> OTHER INFORMATION: Synthetic primer

<400> SEQUENCE: 31
ctttaccgac cattggattc actgggtaaa acagaac                              37

<210> SEQ ID NO 32
<211> LENGTH: 37
<212> TYPE: DNA
<213> ORGANISM: Artificial Sequence
<220> FEATURE:
<223> OTHER INFORMATION: Synthetic primer

<400> SEQUENCE: 32
ctttaccgac cattatattc actgggtaaa acagaac                              37

<210> SEQ ID NO 33
<211> LENGTH: 37
<212> TYPE: DNA
<213> ORGANISM: Artificial Sequence
<220> FEATURE:
<223> OTHER INFORMATION: Synthetic primer

<400> SEQUENCE: 33
ctgggtaaaa cagcgcccgg aacagggcct ggagtgg                              37

<210> SEQ ID NO 34
<211> LENGTH: 37
<212> TYPE: DNA
<213> ORGANISM: Artificial Sequence
<220> FEATURE:
<223> OTHER INFORMATION: Synthetic primer

<400> SEQUENCE: 34
gattgggtat attagcccgg gtaatgatga ctttaag                              37

<210> SEQ ID NO 35
<211> LENGTH: 36
<212> TYPE: DNA
<213> ORGANISM: Artificial Sequence
<220> FEATURE:
<223> OTHER INFORMATION: Synthetic primer

<400> SEQUENCE: 35
gtaatgatga caccaagtat aacgaacgct ttaaag                               36
```

```
<210> SEQ ID NO 36
<211> LENGTH: 36
<212> TYPE: DNA
<213> ORGANISM: Artificial Sequence
<220> FEATURE:
<223> OTHER INFORMATION: Synthetic primer

<400> SEQUENCE: 36
gtataacgaa aaatttaaag gtaaagccac cctgac                            36

<210> SEQ ID NO 37
<211> LENGTH: 36
<212> TYPE: DNA
<213> ORGANISM: Artificial Sequence
<220> FEATURE:
<223> OTHER INFORMATION: Synthetic primer

<400> SEQUENCE: 37
gtataacgaa agctttaaag gtaaagccac cctgac                            36

<210> SEQ ID NO 38
<211> LENGTH: 38
<212> TYPE: DNA
<213> ORGANISM: Artificial Sequence
<220> FEATURE:
<223> OTHER INFORMATION: Synthetic primer

<400> SEQUENCE: 38
gtccactgct tacctgcagc tgaacagtct cacgtcag                          38

<210> SEQ ID NO 39
<211> LENGTH: 38
<212> TYPE: DNA
<213> ORGANISM: Artificial Sequence
<220> FEATURE:
<223> OTHER INFORMATION: Synthetic primer

<400> SEQUENCE: 39
gtccactgct tacatgcagc tgaacagtct cacgtcag                          38

<210> SEQ ID NO 40
<211> LENGTH: 36
<212> TYPE: DNA
<213> ORGANISM: Artificial Sequence
<220> FEATURE:
<223> OTHER INFORMATION: Synthetic primer

<400> SEQUENCE: 40
gatattgtca tgacccaatc tccgtcatca ctgccc                            36

<210> SEQ ID NO 41
<211> LENGTH: 38
<212> TYPE: DNA
<213> ORGANISM: Artificial Sequence
<220> FEATURE:
<223> OTHER INFORMATION: Synthetic primer

<400> SEQUENCE: 41
ctattgggcc tctaaccgtg aatccggtgt tccagatc                          38

<210> SEQ ID NO 42
<211> LENGTH: 38
<212> TYPE: DNA
<213> ORGANISM: Artificial Sequence
<220> FEATURE:
<223> OTHER INFORMATION: Synthetic primer

<400> SEQUENCE: 42
```

```
ctattgggcc tctacccgtg aatccggtgt tccagatc                             38
```

<210> SEQ ID NO 43
<211> LENGTH: 37
<212> TYPE: DNA
<213> ORGANISM: Artificial Sequence
<220> FEATURE:
<223> OTHER INFORMATION: Synthetic primer

<400> SEQUENCE: 43

```
catttcgtct gtggaaacag aagacctggc tgtctac                              37
```

<210> SEQ ID NO 44
<211> LENGTH: 37
<212> TYPE: DNA
<213> ORGANISM: Artificial Sequence
<220> FEATURE:
<223> OTHER INFORMATION: Synthetic primer

<400> SEQUENCE: 44

```
catttcgtct gtgcagacag aagacctggc tgtctac                              37
```

<210> SEQ ID NO 45
<211> LENGTH: 39
<212> TYPE: DNA
<213> ORGANISM: Artificial Sequence
<220> FEATURE:
<223> OTHER INFORMATION: Synthetic primer

<400> SEQUENCE: 45

```
gtactaaatt agaactcaaa acaccggtgt cagaaaaac                            39
```

<210> SEQ ID NO 46
<211> LENGTH: 38
<212> TYPE: DNA
<213> ORGANISM: Artificial Sequence
<220> FEATURE:
<223> OTHER INFORMATION: Synthetic primer

<400> SEQUENCE: 46

```
aacaccggtg tcacgcaaac agctggcgga ggtggtcg                             38
```

<210> SEQ ID NO 47
<211> LENGTH: 36
<212> TYPE: DNA
<213> ORGANISM: Artificial Sequence
<220> FEATURE:
<223> OTHER INFORMATION: Synthetic primer

<400> SEQUENCE: 47

```
aaacagctgg cgaaagtggt cgcgaatacg attacc                               36
```

<210> SEQ ID NO 48
<211> LENGTH: 37
<212> TYPE: DNA
<213> ORGANISM: Artificial Sequence
<220> FEATURE:
<223> OTHER INFORMATION: Synthetic primer

<400> SEQUENCE: 48

```
ttttaggtgg gcgcgccatt gctcgcggtg aaatttc                              37
```

<210> SEQ ID NO 49
<211> LENGTH: 36
<212> TYPE: DNA
<213> ORGANISM: Artificial Sequence

```
<220> FEATURE:
<223> OTHER INFORMATION: Synthetic primer

<400> SEQUENCE: 49
gaaatttcgc tgcgcgatgc ggtgaccaga tactgg                              36

<210> SEQ ID NO 50
<211> LENGTH: 37
<212> TYPE: DNA
<213> ORGANISM: Artificial Sequence
<220> FEATURE:
<223> OTHER INFORMATION: Synthetic primer

<400> SEQUENCE: 50
acaggtaccg gatcgcgtca cggataacgc ctccctg                             37

<210> SEQ ID NO 51
<211> LENGTH: 33
<212> TYPE: DNA
<213> ORGANISM: Artificial Sequence
<220> FEATURE:
<223> OTHER INFORMATION: Synthetic primer

<400> SEQUENCE: 51
gatgaggtca cgcgcaacgc ctccctgctg cgc                                 33

<210> SEQ ID NO 52
<211> LENGTH: 37
<212> TYPE: DNA
<213> ORGANISM: Artificial Sequence
<220> FEATURE:
<223> OTHER INFORMATION: Synthetic primer

<400> SEQUENCE: 52
tggcatgccc tatcgccagg ccatgacgac gcgggtc                             37

<210> SEQ ID NO 53
<211> LENGTH: 36
<212> TYPE: DNA
<213> ORGANISM: Artificial Sequence
<220> FEATURE:
<223> OTHER INFORMATION: Synthetic primer

<400> SEQUENCE: 53
ccgctcaagc tgaaacatac ctggattaac gtgccg                              36

<210> SEQ ID NO 54
<211> LENGTH: 37
<212> TYPE: DNA
<213> ORGANISM: Artificial Sequence
<220> FEATURE:
<223> OTHER INFORMATION: Synthetic primer

<400> SEQUENCE: 54
ccgaaagcgg aacgcgcgca ttacgcctgg ggctatc                             37

<210> SEQ ID NO 55
<211> LENGTH: 38
<212> TYPE: DNA
<213> ORGANISM: Artificial Sequence
<220> FEATURE:
<223> OTHER INFORMATION: Synthetic primer

<400> SEQUENCE: 55
ccgggtatgc tgcgcgcaca agcctatggc gtgaaaac                            38
```

<210> SEQ ID NO 56
<211> LENGTH: 35
<212> TYPE: DNA
<213> ORGANISM: Artificial Sequence
<220> FEATURE:
<223> OTHER INFORMATION: Synthetic primer

<400> SEQUENCE: 56
aaacatggcg ccgcgcaacg ttgctgatgc ctcac                              35

<210> SEQ ID NO 57
<211> LENGTH: 37
<212> TYPE: DNA
<213> ORGANISM: Artificial Sequence
<220> FEATURE:
<223> OTHER INFORMATION: Synthetic primer

<400> SEQUENCE: 57
ggagaacgtt gctcgcgcct cacttaagca gggcatc                            37

<210> SEQ ID NO 58
<211> LENGTH: 36
<212> TYPE: DNA
<213> ORGANISM: Artificial Sequence
<220> FEATURE:
<223> OTHER INFORMATION: Synthetic primer

<400> SEQUENCE: 58
caactggccc gtgaaagcca acacggtggt cgagac                             36

<210> SEQ ID NO 59
<211> LENGTH: 36
<212> TYPE: DNA
<213> ORGANISM: Artificial Sequence
<220> FEATURE:
<223> OTHER INFORMATION: Synthetic primer

<400> SEQUENCE: 59
caacacggtg gtccgcacga gttttggtaa tgtagc                             36

<210> SEQ ID NO 60
<211> LENGTH: 37
<212> TYPE: DNA
<213> ORGANISM: Artificial Sequence
<220> FEATURE:
<223> OTHER INFORMATION: Synthetic primer

<400> SEQUENCE: 60
ggcctttatt cctcgcaagc agatcggtat tgtgatg                            37

<210> SEQ ID NO 61
<211> LENGTH: 36
<212> TYPE: DNA
<213> ORGANISM: Artificial Sequence
<220> FEATURE:
<223> OTHER INFORMATION: Synthetic primer

<400> SEQUENCE: 61
ccggcacgcg ttaaagcggc ataccatatc ctcgag                             36

<210> SEQ ID NO 62
<211> LENGTH: 37
<212> TYPE: DNA
<213> ORGANISM: Artificial Sequence
<220> FEATURE:
<223> OTHER INFORMATION: Synthetic primer

<400> SEQUENCE: 62

| ataccatatc ctcaaagcgc tacagtagga attcgag | 37 |

<210> SEQ ID NO 63
<211> LENGTH: 37
<212> TYPE: DNA
<213> ORGANISM: Artificial Sequence
<220> FEATURE:
<223> OTHER INFORMATION: Synthetic primer

<400> SEQUENCE: 63

| accggtgtca gaagaacagc tggcggaggt ggtcgcg | 37 |

<210> SEQ ID NO 64
<211> LENGTH: 37
<212> TYPE: DNA
<213> ORGANISM: Artificial Sequence
<220> FEATURE:
<223> OTHER INFORMATION: Synthetic primer

<400> SEQUENCE: 64

| taccccgctg atggaagccc agtctgttcc aggcatg | 37 |

<210> SEQ ID NO 65
<211> LENGTH: 36
<212> TYPE: DNA
<213> ORGANISM: Artificial Sequence
<220> FEATURE:
<223> OTHER INFORMATION: Synthetic primer

<400> SEQUENCE: 65

| tatttatcag ggagaaccgc actattacac atttgg | 36 |

<210> SEQ ID NO 66
<211> LENGTH: 37
<212> TYPE: DNA
<213> ORGANISM: Artificial Sequence
<220> FEATURE:
<223> OTHER INFORMATION: Synthetic primer

<400> SEQUENCE: 66

| tacacatttg gcgaagccga tatcgcggcg aataaac | 37 |

<210> SEQ ID NO 67
<211> LENGTH: 36
<212> TYPE: DNA
<213> ORGANISM: Artificial Sequence
<220> FEATURE:
<223> OTHER INFORMATION: Synthetic primer

<400> SEQUENCE: 67

| atcgcggcga atgaacccgt tacgcctcag accctg | 36 |

<210> SEQ ID NO 68
<211> LENGTH: 37
<212> TYPE: DNA
<213> ORGANISM: Artificial Sequence
<220> FEATURE:
<223> OTHER INFORMATION: Synthetic primer

<400> SEQUENCE: 68

| gatgccattg ctgaaggtga aatttcgctg gacgatg | 37 |

<210> SEQ ID NO 69
<211> LENGTH: 35
<212> TYPE: DNA
<213> ORGANISM: Artificial Sequence
<220> FEATURE:
<223> OTHER INFORMATION: Synthetic primer

<400> SEQUENCE: 69
gatgcggtga ccgaatactg gccacagctg acggg					35

<210> SEQ ID NO 70
<211> LENGTH: 35
<212> TYPE: DNA
<213> ORGANISM: Artificial Sequence
<220> FEATURE:
<223> OTHER INFORMATION: Synthetic primer

<400> SEQUENCE: 70
agctgacggg cgaacagtgg cagggtattc gtatg					35

<210> SEQ ID NO 71
<211> LENGTH: 36
<212> TYPE: DNA
<213> ORGANISM: Artificial Sequence
<220> FEATURE:
<223> OTHER INFORMATION: Synthetic primer

<400> SEQUENCE: 71
tggcagggta ttgatatgct ggatctcgcc acctac					36

<210> SEQ ID NO 72
<211> LENGTH: 37
<212> TYPE: DNA
<213> ORGANISM: Artificial Sequence
<220> FEATURE:
<223> OTHER INFORMATION: Synthetic primer

<400> SEQUENCE: 72
acgcctccct gctggatttt tatcaaaact ggcagcc					37

<210> SEQ ID NO 73
<211> LENGTH: 36
<212> TYPE: DNA
<213> ORGANISM: Artificial Sequence
<220> FEATURE:
<223> OTHER INFORMATION: Synthetic primer

<400> SEQUENCE: 73
cagccgcagt gggatcctgg cacaacgcgt ctttac					36

<210> SEQ ID NO 74
<211> LENGTH: 36
<212> TYPE: DNA
<213> ORGANISM: Artificial Sequence
<220> FEATURE:
<223> OTHER INFORMATION: Synthetic primer

<400> SEQUENCE: 74
gcgctggcgg tcgatccttc tggcatgccc tatgag					36

<210> SEQ ID NO 75
<211> LENGTH: 36
<212> TYPE: DNA
<213> ORGANISM: Artificial Sequence
<220> FEATURE:
<223> OTHER INFORMATION: Synthetic primer

<400> SEQUENCE: 75
gacgcgggtc cttgatccgc tcaagctgga ccatac					36

```
<210> SEQ ID NO 76
<211> LENGTH: 36
<212> TYPE: DNA
<213> ORGANISM: Artificial Sequence
<220> FEATURE:
<223> OTHER INFORMATION: Synthetic primer

<400> SEQUENCE: 76
cttaagccgc tcgatctgga ccatacctgg attaac                              36

<210> SEQ ID NO 77
<211> LENGTH: 36
<212> TYPE: DNA
<213> ORGANISM: Artificial Sequence
<220> FEATURE:
<223> OTHER INFORMATION: Synthetic primer

<400> SEQUENCE: 77
gattaacgtg ccggaagcgg aagaggcgca ttacgc                              36

<210> SEQ ID NO 78
<211> LENGTH: 37
<212> TYPE: DNA
<213> ORGANISM: Artificial Sequence
<220> FEATURE:
<223> OTHER INFORMATION: Synthetic primer

<400> SEQUENCE: 78
tgatgcctca cttgaacagg gcatcgcgct ggcgcag                             37

<210> SEQ ID NO 79
<211> LENGTH: 37
<212> TYPE: DNA
<213> ORGANISM: Artificial Sequence
<220> FEATURE:
<223> OTHER INFORMATION: Synthetic primer

<400> SEQUENCE: 79
agtcgcgcta ctgggaaatc gggtcaatgt atcaggg                             37

<210> SEQ ID NO 80
<211> LENGTH: 36
<212> TYPE: DNA
<213> ORGANISM: Artificial Sequence
<220> FEATURE:
<223> OTHER INFORMATION: Synthetic primer

<400> SEQUENCE: 80
ggctcccccg gtcgaagcgt cctgggtcca taaaac                              36

<210> SEQ ID NO 81
<211> LENGTH: 36
<212> TYPE: DNA
<213> ORGANISM: Artificial Sequence
<220> FEATURE:
<223> OTHER INFORMATION: Synthetic primer

<400> SEQUENCE: 81
tttattcctg aagaacagat cggtattgtg atgctc                              36

<210> SEQ ID NO 82
<211> LENGTH: 37
<212> TYPE: DNA
<213> ORGANISM: Artificial Sequence
<220> FEATURE:
<223> OTHER INFORMATION: Synthetic primer

<400> SEQUENCE: 82
```

```
tccgaacccg gcagaagttg aggcggcata ccatatc                              37

<210> SEQ ID NO 83
<211> LENGTH: 36
<212> TYPE: DNA
<213> ORGANISM: Artificial Sequence
<220> FEATURE:
<223> OTHER INFORMATION: Synthetic primer

<400> SEQUENCE: 83
gttacagcag tcacgcgcgg agttggtgaa accggg                               36

<210> SEQ ID NO 84
<211> LENGTH: 35
<212> TYPE: DNA
<213> ORGANISM: Artificial Sequence
<220> FEATURE:
<223> OTHER INFORMATION: Synthetic primer

<400> SEQUENCE: 84
cagtcagatg cgcgcttggt gaaaccgggc gcgag                                35

<210> SEQ ID NO 85
<211> LENGTH: 37
<212> TYPE: DNA
<213> ORGANISM: Artificial Sequence
<220> FEATURE:
<223> OTHER INFORMATION: Synthetic primer

<400> SEQUENCE: 85
taaaacagaa cccgcgccag ggcctggagt ggattgg                              37

<210> SEQ ID NO 86
<211> LENGTH: 36
<212> TYPE: DNA
<213> ORGANISM: Artificial Sequence
<220> FEATURE:
<223> OTHER INFORMATION: Synthetic primer

<400> SEQUENCE: 86
ggaacagggc ctgaaatgga ttgggtattt cagccc                               36

<210> SEQ ID NO 87
<211> LENGTH: 36
<212> TYPE: DNA
<213> ORGANISM: Artificial Sequence
<220> FEATURE:
<223> OTHER INFORMATION: Synthetic primer

<400> SEQUENCE: 87
ctttaagtat aaccgccgct ttaaaggtaa agccac                               36

<210> SEQ ID NO 88
<211> LENGTH: 36
<212> TYPE: DNA
<213> ORGANISM: Artificial Sequence
<220> FEATURE:
<223> OTHER INFORMATION: Synthetic primer

<400> SEQUENCE: 88
accctgacgg cgaaaaaatc gtcgtccact gcttac                               36

<210> SEQ ID NO 89
<211> LENGTH: 36
<212> TYPE: DNA
<213> ORGANISM: Artificial Sequence
```

```
<220> FEATURE:
<223> OTHER INFORMATION: Synthetic primer

<400> SEQUENCE: 89
cagtctcacg tcacgcgata gcgcggtgta tttctg                              36

<210> SEQ ID NO 90
<211> LENGTH: 35
<212> TYPE: DNA
<213> ORGANISM: Artificial Sequence
<220> FEATURE:
<223> OTHER INFORMATION: Synthetic primer

<400> SEQUENCE: 90
ggcggtggat ctcgcattgt catgacccaa tctcc                               35

<210> SEQ ID NO 91
<211> LENGTH: 38
<212> TYPE: DNA
<213> ORGANISM: Artificial Sequence
<220> FEATURE:
<223> OTHER INFORMATION: Synthetic primer

<400> SEQUENCE: 91
gtgagtgttg gaaaaaaggt gacgctgagt tgcaaaag                            38

<210> SEQ ID NO 92
<211> LENGTH: 36
<212> TYPE: DNA
<213> ORGANISM: Artificial Sequence
<220> FEATURE:
<223> OTHER INFORMATION: Synthetic primer

<400> SEQUENCE: 92
gcctctaccc gtaaatccgg tgttccagat cgtttc                              36

<210> SEQ ID NO 93
<211> LENGTH: 35
<212> TYPE: DNA
<213> ORGANISM: Artificial Sequence
<220> FEATURE:
<223> OTHER INFORMATION: Synthetic primer

<400> SEQUENCE: 93
tccggtgttc caaaacgttt caccggcagt ggttc                               35

<210> SEQ ID NO 94
<211> LENGTH: 35
<212> TYPE: DNA
<213> ORGANISM: Artificial Sequence
<220> FEATURE:
<223> OTHER INFORMATION: Synthetic primer

<400> SEQUENCE: 94
ggttcgggca ctaaatttac actgtccatt tcgtc                               35

<210> SEQ ID NO 95
<211> LENGTH: 36
<212> TYPE: DNA
<213> ORGANISM: Artificial Sequence
<220> FEATURE:
<223> OTHER INFORMATION: Synthetic primer

<400> SEQUENCE: 95
atttcgtctg tgaaaacaga agacctggct gtctac                              36
```

```
<210> SEQ ID NO 96
<211> LENGTH: 36
<212> TYPE: DNA
<213> ORGANISM: Artificial Sequence
<220> FEATURE:
<223> OTHER INFORMATION: Synthetic primer

<400> SEQUENCE: 96
gtctgtggaa acaaaagacc tggctgtcta ctattg                               36

<210> SEQ ID NO 97
<211> LENGTH: 39
<212> TYPE: DNA
<213> ORGANISM: Artificial Sequence
<220> FEATURE:
<223> OTHER INFORMATION: Synthetic primer

<400> SEQUENCE: 97
tgcggagttg gtggaaccgg gcgcgagcgt aaagatttc                            39

<210> SEQ ID NO 98
<211> LENGTH: 35
<212> TYPE: DNA
<213> ORGANISM: Artificial Sequence
<220> FEATURE:
<223> OTHER INFORMATION: Synthetic primer

<400> SEQUENCE: 98
ggcgcgagcg tagaaatttc ttgtaaagca tccgg                                35

<210> SEQ ID NO 99
<211> LENGTH: 36
<212> TYPE: DNA
<213> ORGANISM: Artificial Sequence
<220> FEATURE:
<223> OTHER INFORMATION: Synthetic primer

<400> SEQUENCE: 99
aaagatttct tgtgaagcat ccggctacac ctttac                               36

<210> SEQ ID NO 100
<211> LENGTH: 37
<212> TYPE: DNA
<213> ORGANISM: Artificial Sequence
<220> FEATURE:
<223> OTHER INFORMATION: Synthetic primer

<400> SEQUENCE: 100
cattcactgg gtagaacaga acccggaaca gggcctg                              37

<210> SEQ ID NO 101
<211> LENGTH: 36
<212> TYPE: DNA
<213> ORGANISM: Artificial Sequence
<220> FEATURE:
<223> OTHER INFORMATION: Synthetic primer

<400> SEQUENCE: 101
taatgatgac tttgaatata acgaacgctt taaagg                               36

<210> SEQ ID NO 102
<211> LENGTH: 37
<212> TYPE: DNA
<213> ORGANISM: Artificial Sequence
<220> FEATURE:
<223> OTHER INFORMATION: Synthetic primer

<400> SEQUENCE: 102
```

```
taagtataac gaagatttta aaggtaaagc caccctg                                   37

<210> SEQ ID NO 103
<211> LENGTH: 37
<212> TYPE: DNA
<213> ORGANISM: Artificial Sequence
<220> FEATURE:
<223> OTHER INFORMATION: Synthetic primer

<400> SEQUENCE: 103
ataacgaacg ctttgaaggt aaagccaccc tgacggc                                   37

<210> SEQ ID NO 104
<211> LENGTH: 36
<212> TYPE: DNA
<213> ORGANISM: Artificial Sequence
<220> FEATURE:
<223> OTHER INFORMATION: Synthetic primer

<400> SEQUENCE: 104
ctgacggcgg acgattcgtc gtccactgct tacctg                                    36

<210> SEQ ID NO 105
<211> LENGTH: 36
<212> TYPE: DNA
<213> ORGANISM: Artificial Sequence
<220> FEATURE:
<223> OTHER INFORMATION: Synthetic primer

<400> SEQUENCE: 105
gagtgttgga gaagatgtga cgctgagttg caaaag                                    36

<210> SEQ ID NO 106
<211> LENGTH: 37
<212> TYPE: DNA
<213> ORGANISM: Artificial Sequence
<220> FEATURE:
<223> OTHER INFORMATION: Synthetic primer

<400> SEQUENCE: 106
gacgctgagt tgcgaaagct cccaaagcct gctatac                                   37

<210> SEQ ID NO 107
<211> LENGTH: 36
<212> TYPE: DNA
<213> ORGANISM: Artificial Sequence
<220> FEATURE:
<223> OTHER INFORMATION: Synthetic primer

<400> SEQUENCE: 107
tggtatcagc aggaaccagg ccagtctcct aaattg                                    36

<210> SEQ ID NO 108
<211> LENGTH: 36
<212> TYPE: DNA
<213> ORGANISM: Artificial Sequence
<220> FEATURE:
<223> OTHER INFORMATION: Synthetic primer

<400> SEQUENCE: 108
aggccagtct cctgaattgc tgatctattg ggcctc                                    36

<210> SEQ ID NO 109
<211> LENGTH: 36
<212> TYPE: DNA
<213> ORGANISM: Artificial Sequence
```

```
<220> FEATURE:
<223> OTHER INFORMATION: Synthetic primer

<400> SEQUENCE: 109
ttgggcctct accgaagaat ccggtgttcc agatcg                                36

<210> SEQ ID NO 110
<211> LENGTH: 35
<212> TYPE: DNA
<213> ORGANISM: Artificial Sequence
<220> FEATURE:
<223> OTHER INFORMATION: Synthetic primer

<400> SEQUENCE: 110
gggcgggtac tgaattagtt ctcaaaacac cggtg                                 35

<210> SEQ ID NO 111
<211> LENGTH: 37
<212> TYPE: DNA
<213> ORGANISM: Artificial Sequence
<220> FEATURE:
<223> OTHER INFORMATION: Synthetic primer

<400> SEQUENCE: 111
taaattagtt ctcgaaacac cggtgtcaga aaaacag                               37

<210> SEQ ID NO 112
<211> LENGTH: 49
<212> TYPE: DNA
<213> ORGANISM: Artificial Sequence
<220> FEATURE:
<223> OTHER INFORMATION: Synthetic primer

<400> SEQUENCE: 112
actaaattag ttctcaaaac accggtgcac ccagaaacgc tggtgaaag                  49

<210> SEQ ID NO 113
<211> LENGTH: 66
<212> TYPE: DNA
<213> ORGANISM: Artificial Sequence
<220> FEATURE:
<223> OTHER INFORMATION: Synthetic primer

<400> SEQUENCE: 113
cgtttgatct cgagtgcggc cgcaagcttg tcgacggagc tcgttaccaa tgcttaatca     60
gtgagg                                                                66

<210> SEQ ID NO 114
<211> LENGTH: 41
<212> TYPE: DNA
<213> ORGANISM: Artificial Sequence
<220> FEATURE:
<223> OTHER INFORMATION: Synthetic primer

<400> SEQUENCE: 114
actaaattag ttctcaaaca ccggtgtcag aaaaacagct g                          41

<210> SEQ ID NO 115
<211> LENGTH: 68
<212> TYPE: DNA
<213> ORGANISM: Artificial Sequence
<220> FEATURE:
<223> OTHER INFORMATION: Synthetic primer

<400> SEQUENCE: 115
cgtttgatct cgagtgcggc cgcaagcttg tcgacggagc tcgttactgt agcgcctcta     60
```

-continued

```
<210> SEQ ID NO 116
<211> LENGTH: 35
<212> TYPE: DNA
<213> ORGANISM: Artificial Sequence
<220> FEATURE:
<223> OTHER INFORMATION: Synthetic primer

<400> SEQUENCE: 116
cagtctccta aatgcctgat ctattgggcc tctac                          35

<210> SEQ ID NO 117
<211> LENGTH: 36
<212> TYPE: DNA
<213> ORGANISM: Artificial Sequence
<220> FEATURE:
<223> OTHER INFORMATION: Synthetic primer

<400> SEQUENCE: 117
agccttaaca tgtgctattg gggtcaaggg accagc                         36

<210> SEQ ID NO 118
<211> LENGTH: 37
<212> TYPE: DNA
<213> ORGANISM: Artificial Sequence
<220> FEATURE:
<223> OTHER INFORMATION: Synthetic primer

<400> SEQUENCE: 118
ctgggtaaaa caggcgccgg aacagggcct ggagtgg                        37

<210> SEQ ID NO 119
<211> LENGTH: 37
<212> TYPE: DNA
<213> ORGANISM: Artificial Sequence
<220> FEATURE:
<223> OTHER INFORMATION: Synthetic primer

<400> SEQUENCE: 119
ctgggtaaaa cagccgccgg aacagggcct ggagtgg                        37
```